United States Patent
Tadano et al.

(10) Patent No.: US 11,629,154 B2
(45) Date of Patent: Apr. 18, 2023

(54) TETRAHYDROPYRANOOXAZINE DERIVATIVES HAVING SELECTIVE BACE1 INHIBITORY ACTIVITY

(71) Applicant: SHIONOGI & CO., LTD., Osaka (JP)

(72) Inventors: Genta Tadano, Osaka (JP); Shinji Suzuki, Osaka (JP); Ken-ichi Kusakabe, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 141 days.

(21) Appl. No.: 17/050,663

(22) PCT Filed: Apr. 25, 2019

(86) PCT No.: PCT/JP2019/017619
§ 371 (c)(1),
(2) Date: Oct. 26, 2020

(87) PCT Pub. No.: WO2019/208693
PCT Pub. Date: Oct. 31, 2019

(65) Prior Publication Data
US 2021/0238194 A1    Aug. 5, 2021

(30) Foreign Application Priority Data
Apr. 27, 2018    (JP) .............. JP2018-086206

(51) Int. Cl.
| | | |
|---|---|---|
| C07D 498/04 | (2006.01) | |
| A61P 25/28 | (2006.01) | |
| A61K 9/00 | (2006.01) | |
| A61K 9/20 | (2006.01) | |
| A61K 9/48 | (2006.01) | |

(52) U.S. Cl.
CPC .......... *C07D 498/04* (2013.01); *A61K 9/0019* (2013.01); *A61K 9/0053* (2013.01); *A61K 9/2018* (2013.01); *A61K 9/4858* (2013.01); *A61P 25/28* (2018.01)

(58) Field of Classification Search
None
See application file for complete search history.

(56) References Cited

U.S. PATENT DOCUMENTS

| | | |
|---|---|---|
| 9,273,042 B2 | 3/2016 | Hilpert et al. |
| 2006/0287294 A1 | 12/2006 | Zhu et al. |
| 2008/0200445 A1 | 8/2008 | Zhu et al. |
| 2012/0202803 A1 | 8/2012 | Hilpert et al. |
| 2012/0245157 A1* | 9/2012 | Masui .......... C07D 498/04 544/91 |
| 2013/0072478 A1 | 3/2013 | Hilpert et al. |
| 2014/0107109 A1 | 4/2014 | Lewis et al. |
| 2014/0235626 A1 | 8/2014 | Tada et al. |
| 2014/0271911 A1 | 9/2014 | Wallace |
| 2015/0038497 A1 | 2/2015 | Lewis et al. |
| 2015/0344500 A1 | 12/2015 | Cumming et al. |
| 2016/0213645 A1 | 7/2016 | Wallace |

FOREIGN PATENT DOCUMENTS

| | | |
|---|---|---|
| EP | 1942105 | 7/2008 |
| EP | 2147914 | 1/2010 |
| EP | 2151435 | 2/2010 |
| EP | 2305672 | 4/2011 |
| EP | 2360155 | 8/2011 |
| EP | 2415756 | 2/2012 |
| EP | 2500344 | 9/2012 |
| EP | 2511268 | 10/2012 |
| EP | 2511269 | 10/2012 |

(Continued)

OTHER PUBLICATIONS

Williams et al (Foye's Principles of Medicinal Chemistry, 5th Edition, pp. 59-63, 2002) (Year: 2002).*
Patani et al (Chem Rev 96:3147-3176, 1996) (Year: 1996).*
International Search Report and Written Opinion of PCT/JP2019/017619, dated Jul. 3, 2019, 8 pages.
Kouki Fuchino et al., "Rational Design of Novel 1,3-Oxazine Based β-Secretase (BACE1) Inhibitors: Incorporation of a Double Bond To Reduce P-gp Efflux Leading to Robust Aβ Reduction in the Brain", Journal of Medicinal Chemistry, 2018, 61, 5122-5137.

(Continued)

*Primary Examiner* — Craig D Ricci
(74) *Attorney, Agent, or Firm* — Hamre, Schumann, Mueller & Larson, P.C.

(57) ABSTRACT

The present invention provides a compound which has an effect of inhibiting amyloid ßproduction, especially an effect of inhibiting BACE1, and which is useful as a therapeutic or prophylactic agent for diseases induced by production, secretion and/or deposition of amyloid ßproteins.

A compound of Formula (I) wherein $R^3$ is each independently alkyl optionally substituted with halogen, cyano, alkyloxy, haloalkyloxy or non-aromatic carbocyclyl, or the like;

t is integer from 0 to 3;

$R^5$ is a hydrogen atom or halogen;

$R^6$ is selected from the group consisting of a hydrogen atom, halogen, and substituted or unsubstituted alkyl; ring B is a substituted or unsubstituted pyrazine or the like;

or a pharmaceutically acceptable salt thereof.

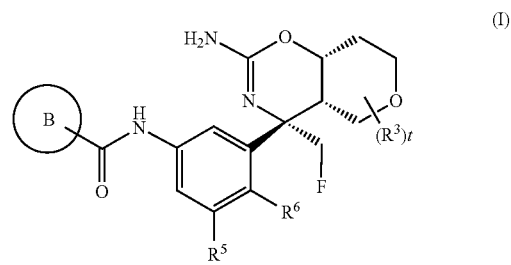

4 Claims, No Drawings

(56) References Cited

FOREIGN PATENT DOCUMENTS

| | | | | |
|---|---|---|---|---|
| EP | 2514747 | 10/2012 | | |
| EP | 2518059 | 10/2012 | | |
| EP | 2597087 | 5/2013 | | |
| EP | 2612854 | 7/2013 | | |
| EP | 2634186 | 9/2013 | | |
| EP | 2634188 | 9/2013 | | |
| EP | 2689780 | 1/2014 | | |
| EP | 2703399 | 3/2014 | | |
| EP | 2703401 | 3/2014 | | |
| JP | 2012-250933 | 12/2012 | | |
| JP | 2014-101353 | 6/2014 | | |
| JP | 2014-101354 | 6/2014 | | |
| JP | 2017-071603 | 4/2017 | | |
| WO | 2007/049532 | 5/2007 | | |
| WO | 2008/103351 | 8/2008 | | |
| WO | 2008/133273 | 11/2008 | | |
| WO | 2008/133274 | 11/2008 | | |
| WO | 2009/134617 | 11/2009 | | |
| WO | 2009/151098 | 12/2009 | | |
| WO | 2010/047372 | 4/2010 | | |
| WO | 2010/113848 | 10/2010 | | |
| WO | 2011/044181 | 4/2011 | | |
| WO | 2011/058763 | 5/2011 | | |
| WO | 2011/069934 | 6/2011 | | |
| WO | 2011/070029 | 6/2011 | | |
| WO | 2011/070781 | 6/2011 | | |
| WO | 2011/071057 | 6/2011 | | |
| WO | 2011/071109 | 6/2011 | | |
| WO | 2011/071135 | 6/2011 | | |
| WO | 2011/077726 | 6/2011 | | |
| WO | 2012/057247 | 5/2012 | | |
| WO | 2012/057248 | 5/2012 | | |
| WO | 2012/107371 | 8/2012 | | |
| WO | WO 2012/107371 | * 8/2012 | ........... | C07D 498/04 |
| WO | 2012/139425 | 10/2012 | | |
| WO | 2012/139993 | 10/2012 | | |
| WO | 2012/147762 | 11/2012 | | |
| WO | 2012/147763 | 11/2012 | | |
| WO | 2012/156284 | 11/2012 | | |
| WO | 2012/168164 | 12/2012 | | |
| WO | 2012/168175 | 12/2012 | | |
| WO | 2013/027188 | 2/2013 | | |
| WO | 2013/028670 | 2/2013 | | |
| WO | 2013/041499 | 3/2013 | | |
| WO | 2013/110622 | 8/2013 | | |
| WO | 2013/174781 | 11/2013 | | |
| WO | 2014/001228 | 1/2014 | | |
| WO | 2014/010748 | 1/2014 | | |
| WO | WO 2014/001228 | * 3/2014 | ........... | C07D 413/12 |
| WO | 2014/059185 | 4/2014 | | |
| WO | 2014/065434 | 5/2014 | | |
| WO | 2014/089149 | 6/2014 | | |
| WO | 2014/093190 | 6/2014 | | |
| WO | 2014/096377 | 6/2014 | | |
| WO | 2014/098831 | 6/2014 | | |
| WO | 2014/099794 | 6/2014 | | |
| WO | 2014/114532 | 7/2014 | | |
| WO | 2014/120658 | 8/2014 | | |
| WO | 2014/134341 | 9/2014 | | |
| WO | 2014/138484 | 9/2014 | | |
| WO | 2014/150344 | 9/2014 | | |
| WO | 2014/166906 | 10/2014 | | |
| WO | 2015/017407 | 2/2015 | | |
| WO | 2015/038446 | 3/2015 | | |
| WO | 2015/051239 | 4/2015 | | |
| WO | 2015/120364 | 8/2015 | | |
| WO | 2015/156421 | 10/2015 | | |
| WO | 2016/025364 | 2/2016 | | |
| WO | 2016/040903 | 3/2016 | | |
| WO | 2017/050978 | 3/2017 | | |
| WO | 2017/061534 | 4/2017 | | |
| WO | 2017/112901 | 6/2017 | | |
| WO | 2017/148878 | 9/2017 | | |
| WO | 2018/112081 | 6/2018 | | |
| WO | 2019/208509 | 10/2019 | | |
| WO | 2020/009179 | 1/2020 | | |

OTHER PUBLICATIONS

Kenji Nakahara et al., "Discovery of Potent and Centrally Active 6-Substituted 5-Fluoro-1,3-dihydro-oxazine 3-Secretase (BACE1) Inhibitors via Active Conformation Stabilization", Journal of Medicinal Chemistry, 2018, 61, 5525-5546.

Kazuki Fujimoto et al., "Structure-Based Design of Selective β-Site Amyloid Precursor Protein Cleaving Enzyme 1 (BACE1) Inhibitors: Targeting the Flap to Gain Selectivity over BACE2", Journal of Medicinal Chemistry, 2019, 62, 5080-5095.

Takuya Oguma et al., "Synthesis of a 6-CF3-Substituted 2-Amino-dihydro-1,3-thiazine β-Secretase Inhibitor by N, N-Diethylaminosulfur Trifluoride-Mediated Chemoselective Cyclization", Journal of Organic Chemistry, 2019, 84, 4893-4897.

Kosuke Anan et al., "Trifluoromethyl Dihydrothiazine-Based β-Secretase (BACE1) Inhibitors with Robust Central β-Amyloid Reduction and Minimal Covalent Binding Burden", ChemMedChem 2019, 14, 1887-1903; available at: https://chemistry-europe.onlinelibrary.wiley.com/doi/full/10.1002/cmdc.201900478, indicating ChemMedChem, 2019, 14, 22, pp. 1894-1910.

Genta Tadano et al., "Discovery of an Extremely Potent Thiazine-Based β-Secretase Inhibitor with Reduced Cardiovascular and Liver Toxicity at a Low Projected Human Dose", Journal of Medicinal Chemistry, 2019, 62, 9331-9337.

Kenji Nakahara et al., "Design and Stereoselective Synthesis of Potent and Centrally Active 1,3-Dihydro-oxazine BACE1 (β-Secretase) Inhibitors: Stabilization of a Bioactive Conformation and Lowering of pKa to Improve In Vivo Efficacy and Mitigate hERG Potential", Poster and Abstract for the 34 th Medicinal Chemistry Symposium in 2016.

Hans Hilpert et al., "β-Secretase (RACE1) Inhibitors with High in Vivo Efficacy Suitable for Clinical Evaluation in Alzheimer's Disease", Journal of Medicinal Chemistry, 2013, vol. 56, Issue:10, pp. 3980-3995.

CAS Registry No. 1630974-41-2, SCIFINDERn, A CAS Solution, 1 page.

CAS Registry No. 1630974-34-3, SCIFINDERn, A CAS Solution, 1 page.

CAS Registry No. 1630974-27-4, SCIFINDERn, A CAS Solution, 1 page.

CAS Registry No. 1630974-23-0, SCIFINDERn, A CAS Solution, 1 page.

Daniel F. Wyss et al., "BACE Inhibitors", Methods and Principles in Medicinal Chemistry, vol. 67, Issue: Fragment-Based Drug Discovery; Lessons and Outlook, 1st Edition, 2016, pp. 329-353.

Jack D. Scott et al., "Discovery of the 3-lmino-1,2,4-thiadiazinane 1,1-Dioxide Derivative Verubecestat (MK-8931)—A 3-Site Amyloid Precursor Protein Cleaving Enzyme 1 Inhibitor for the Treatment of Alzheimer's Disease", Journal of Medicinal Chemistry, vol. 59, Issue: 23, 2016, pp. 10435-10450.

Justyna Godyn et al., "Therapeutic strategies for Alzheimer's disease in clinical trials", Pharmacological Reports, vol. 68, Issue: 1, 2016, pp. 127-138.

Genevieve Evin, "Future Therapeutics in Alzheimer's Disease: Development Status of BACE Inhibitors", BioDrugs, vol. 30, Issue: 3, 2016, pp. 173-194, (MK-8931).

Asher Mullard, Nature Reviews Drug Discovery, vol. 15, Issue: 3, Mar. 2016, p. 151.

Prajakti A. Kothare et al., "An Integrated Strategy for Implementation of Dried Blood Spots in Clinical Development Programs", AAPS Journal, vol. 18, Issue: 2, Mar. 2016, pp. 519-527.

Kelly Willemijn Menting et al., "β-secretase inhibitor; a promising novel therapeutic drug in Alzheimer's disease", Frontiers in Aging Neuroscience, vol. 6, Jul. 2014, 165/1-165/9, 9 pages.

* cited by examiner

TETRAHYDROPYRANOOXAZINE DERIVATIVES HAVING SELECTIVE BACE1 INHIBITORY ACTIVITY

TECHNICAL FIELD

The present invention relates to a compound which has amyloid ß production inhibitory activity, and is useful as an agent for treating or preventing disease induced by production, secretion and/or deposition of amyloid ß proteins.

BACKGROUND ART

In the brain of Alzheimer's patient, the peptide composed of about 40 amino acids residue as is called amyloid ß protein, that accumulates to form insoluble specks (senile specks) outside nerve cells is widely observed. It is concerned that these senile specks kill nerve cells to cause Alzheimer's disease, so the therapeutic agents for Alzheimer's disease, such as decomposition agents of amyloid ß protein and amyloid vaccine, are under investigation.

Secretase is an enzyme which cleaves a protein called amyloid ß precursor protein (APP) in cell and produces amyloid ß protein. The enzyme which controls the production of N terminus of amyloid ß protein is called as ß-secretase (beta-site APP-cleaving enzyme 1, BACE1). It is thought that inhibition of this enzyme leads to reduction of producing amyloid ß protein and that the therapeutic or prophylactic agent for Alzheimer's disease will be created due to the inhibition.

Patent Documents 1 to 10 disclose compounds having a structure similar to those of the compounds of the present invention. Each of these documents discloses each compound is useful as therapeutic agent for Alzheimer's disease, Alzheimer's relating symptoms, diabetes or the like, but each of substantially disclosed compounds has a structure different from the compounds of the present invention.

CITATION LIST

Patent Literature

[PTL 1]
JP2017/071603
[PTL 2]
WO2015/156421
[PTL 3]
JP2014/101354
[PTL 4]
WO2014/065434
[PTL 5]
WO2014/001228
[PTL 6]
WO2013/041499
[PTL 7]
US2013/0072478
[PTL 8]
JP2012/250933
[PTL 9]
WO2012/107371
[PTL 10]
WO2011/071135

SUMMARY OF INVENTION

Technical Problem

The present invention provides compounds which have reducing effects to produce amyloid ß protein, especially selective BACE1 inhibitory activity, and are useful as an agent for treating disease induced by production, secretion and/or deposition of amyloid ß protein.

Advantageous Effects of Invention

The compound of the present invention has selective BACE1 inhibitory activity and is useful as an agent for treating and/or preventing disease induced by production, secretion or deposition of amyloid ß proteins such as Alzheimer dementia.

Solution to Problem

The present invention, for example, provides the inventions described in the following items.

(1) A compound of Formula (I):

[Chem. 1]

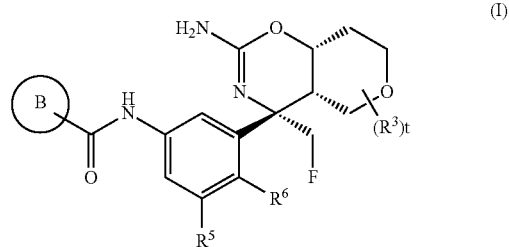

wherein
$R^3$ is each independently alkyl optionally substituted with one or more group(s) selected from halogen, cyano, alkyloxy, haloalkyloxy and non-aromatic carbocyclyl; or heterocyclyl optionally substituted with alkyl;
two $R^3$s attached to a same carbon atom may be taken together with the carbon atom to which they are attached to form a 3- to 5-membered non-aromatic carbocycle optionally substituted with one or more group(s) selected from halogen, alkyl and haloalkyl;
t is an integer from 0 to 3;
$R^5$ is a hydrogen atom or halogen;
$R^6$ is a hydrogen atom, halogen, or substituted or unsubstituted alkyl;

[Chem. 2]

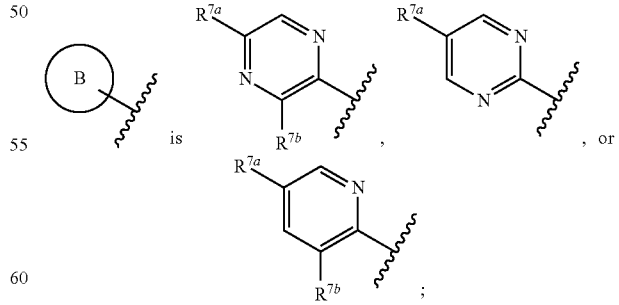

wherein $R^{7a}$ is halogen; cyano; alkyloxy optionally substituted with one or more group(s) selected from cyano, halogen, hydroxy, non-aromatic carbocyclyl and aromatic heterocyclyl; alkyl optionally substituted with one or more halogen; non-aromatic carbocyclyl optionally substituted with one or more group(s) selected from cyano and halogen; non-aromatic heterocyclyl optionally substituted with one or more group(s) selected from cyano and aromatic heterocyclyl; alkenyloxy optionally substituted with one or more group(s) selected from cyano, halogen, and hydroxy; alkynyloxy optionally substituted with one or more group(s) selected from cyano, halogen, and hydroxy; or aromatic heterocyclyl optionally substituted with one or more alkyl; and $R^{7b}$ is a hydrogen atom, halogen, alkyl, haloalkyl or amino;

or a pharmaceutically acceptable salt thereof.

(1)' A compound of Formula (I)

[Chem. 3]

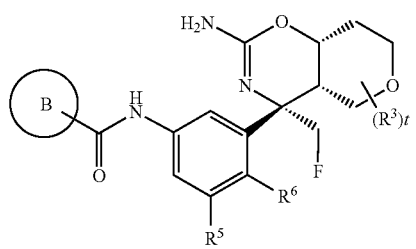

wherein $R^3$ is each independently selected from the group consisting of alkyl optionally substituted with halogen, cyano, alkyloxy, haloalkyloxy or non-aromatic carbocyclyl; and aromatic heterocyclyl optionally substituted with alkyl;

t is an integer from 0 to 3;

$R^5$ is a hydrogen atom or halogen;

$R^6$ is a hydrogen atom, halogen, or substituted or unsubstituted alkyl;

[Chem. 4]

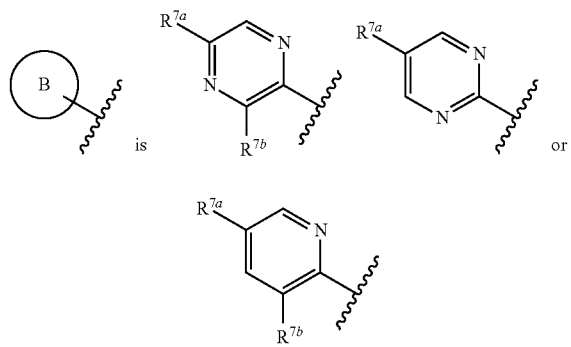

wherein $R^{7a}$ is halogen; cyano; alkyloxy optionally substituted with cyano, halogen, hydroxy or aromatic heterocyclyl; alkyl optionally substituted with halogen; non-aromatic carbocyclyl optionally substituted with cyano or halogen; non-aromatic heterocyclyl optionally substituted with cyano or aromatic heterocyclyl; aromatic heterocyclyl; and $R^{7b}$ is a hydrogen atom, halogen, alkyl, haloalkyl or amino;

or a pharmaceutically acceptable salt thereof.

(2) The compound according to the item (1) or (1)', wherein

[Chem. 5]

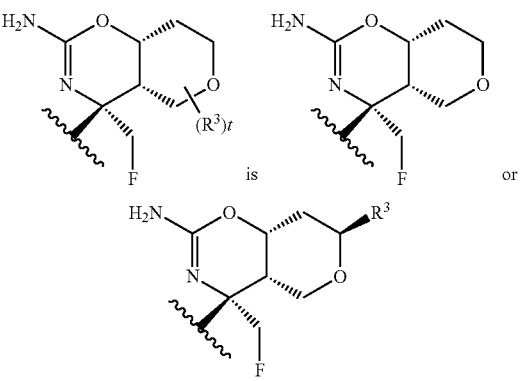

or a pharmaceutically acceptable salt thereof.

(2)' The compound according to the item (1) or (1)', wherein

[Chem. 6]

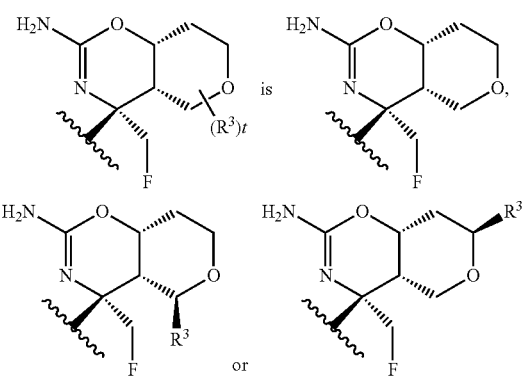

or a pharmaceutically acceptable salt thereof.

(3) The compound according to the any one of the items (1), (2), (2)', and (1)', wherein $R^6$ is fluoro or chloro, or a pharmaceutically acceptable salt thereof.

(3-2) The compound according to any one of the items (1), (2), (2)', and (1)', wherein $R^6$ is fluoro, or a pharmaceutically acceptable salt thereof.

(4) The compound according to any one of the items (1) to (3), (1)', (2)', and (3-2), wherein $R^5$ is a hydrogen atom or fluoro, or a pharmaceutically acceptable salt thereof.

(4-2) The compound according to item (4), wherein $R^5$ is a hydrogen atom, or a pharmaceutically acceptable salt thereof.

(5) The compound according to any one of the items (1) to (4), (1)', (2)', (3-2) and (4-2), wherein $R^3$ is each independently alkyl optionally substituted with one or more halogen, or a pharmaceutically acceptable salt thereof.

(5-2) The compound according to the item (5), wherein $R^3$ is methyl, or a pharmaceutically acceptable salt thereof.

(5-3) The compound according to the item (5), wherein $R^3$ is halomethyl, or a pharmaceutically acceptable salt thereof.

(6) The compound according to any one of the items (1) to (5), (1)', (2)', (3-2), (4-2), (5-2) and (5-3), wherein

[Chem. 7]

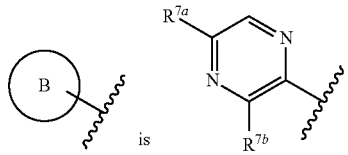

or a pharmaceutically acceptable salt thereof.

(7) The compound according to any one of the item to (1) to (6), (1)', (2)', (3-2), (4-2), (5-2) and (5-3), wherein $R^{7a}$ is cyano or alkyloxy optionally substituted with one or more halogen and $R^{7b}$ is a hydrogen atom, halogen, or amino, or a pharmaceutically acceptable salt thereof.

(7-2) The compound according to the item (7), wherein $R^{7a}$ is methyloxy optionally substituted with one or more halogen, or a pharmaceutically acceptable salt thereof.

(7-3) The compound according to the item (7), wherein $R^{7a}$ is C1-C2 alkyloxy, or a pharmaceutically acceptable salt thereof.

(7-4) The compound according to the item (7), wherein $R^{7a}$ is C1-C2 alkyloxy substituted with one or more halogen, or a pharmaceutically acceptable salt thereof.

(8) The compound according to any one of the items (1) to (5), (1)', (2)', (3-2), (4-2), (5-2) and (5-3), wherein

[Chem. 8]

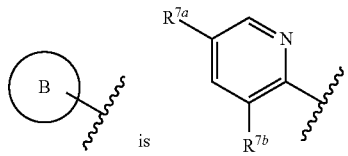

or a pharmaceutically acceptable salt thereof.

(8-2) The compound according to any one of the items (1) to (5), (1)', (2)', (3-2), (4-2), (5-2), (5-3) and (8), wherein $R^{7a}$ is alkyl optionally substituted with one or more halogen and $R^{7b}$ is a hydrogen atom or alkyl, or a pharmaceutically acceptable salt thereof.

(9) The compound according to the any one of the items (1) to (8), (1)', (2)', (3-2), (4-2), (5-2), (5-3), (7-2), (7-3), (7-4), and (8-2), wherein

[Chem. 9]

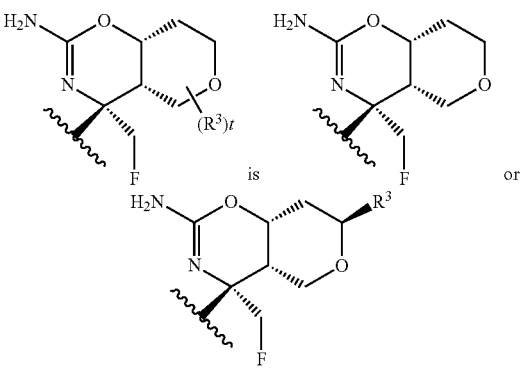

wherein $R^3$ is alkyl optionally substituted with one or more halogen, $R^5$ is a hydrogen atom, $R^6$ is halogen,

[Chem. 10]

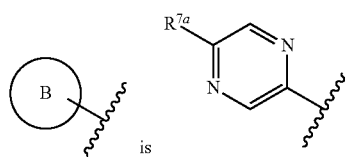

and $R^{7a}$ is alkyloxy optionally substituted with one or more halogen, or a pharmaceutically acceptable salt thereof.

(9-2) The compound according to any one of the item (1) to (9), (1)', (2)', (3-2), (4-2), (5-2), (5-3), (7-2), (7-3), (7-4), and (8-2), wherein the compound is represented by the formula (IA):

[Chem. 11]

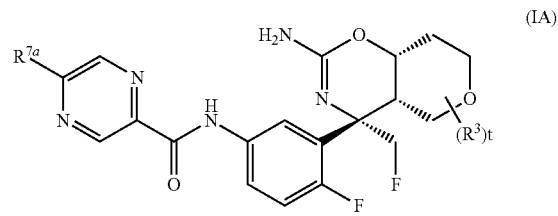

wherein each symbol is the same as defined in the above item (1), or a pharmaceutically acceptable salt thereof.

(9-2)' The compound represented by the formula (IB):

[Chem. 12]

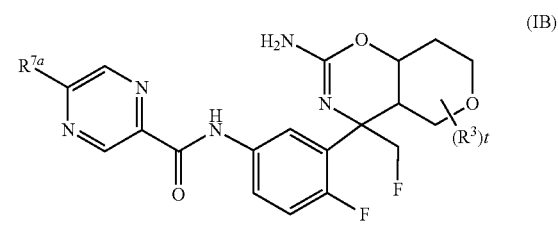

wherein each symbol is the same as defined in any one of the above item (1) to (9), (1)', (2)', (3-2), (4-2), (5-2), (5-3), (7-2), (7-3), (7-4), and (8-2), or a pharmaceutically acceptable salt thereof.

(9-3) The compound according to any one of the item (1) to (9), (1)', (2)', (3-2), (4-2), (5-2), (5-3), (7-2), (7-3), (7-4), (9-2)', and (8-2), wherein the compound is represented by the formula (IA):

[Chem. 13]

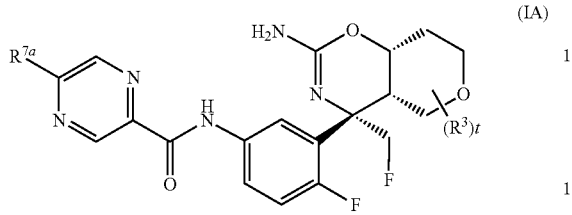

(IA)

wherein $R^{7a}$ is C1-C3 alkyloxy optionally substituted with one or more halogen; $R^3$ is C1-C3 alkyl optionally substituted with one or more halogen; and t is 0 or 1, or a pharmaceutically acceptable salt thereof.

(9-4) The compound according to any one of the item (9), (9-2), (9-2)', and (9-3), wherein $R^{7a}$ is C1-C2 alkyloxy, or a pharmaceutically acceptable salt thereof.

(9-5) The compound according to any one of the item (9), (9-2), (9-2)', and (9-3), wherein $R^{7a}$ is C1-C2 alkyloxy substituted with one or more halogen, or a pharmaceutically acceptable salt thereof.

(10) The compound according to any one of the item (1) to (9), (9-2)', (1)', (2)', (3-2), (4-2), (5-2), (5-3), (7-2), (7-3), (7-4), (8-2), (9-2), (9-3), (9-4) and (9-5) selected from the group consisting of

[Chem. 14]

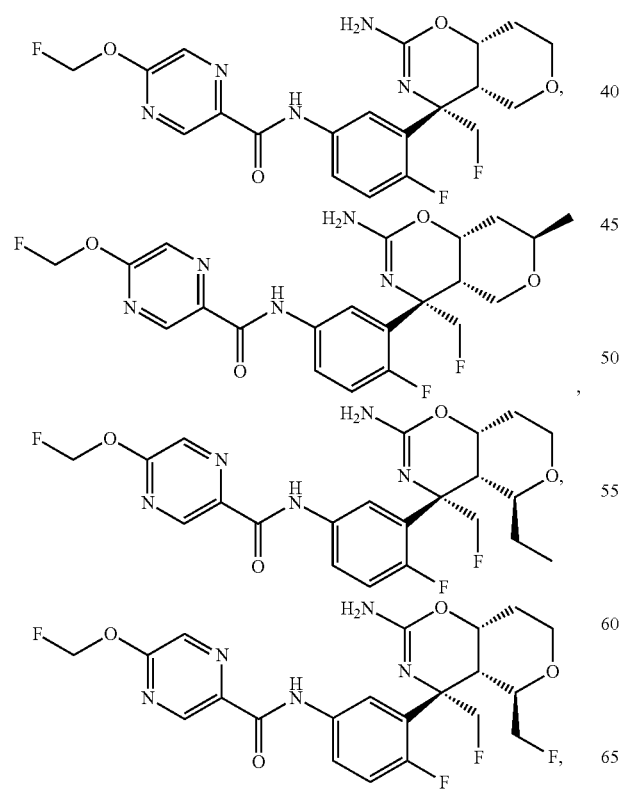

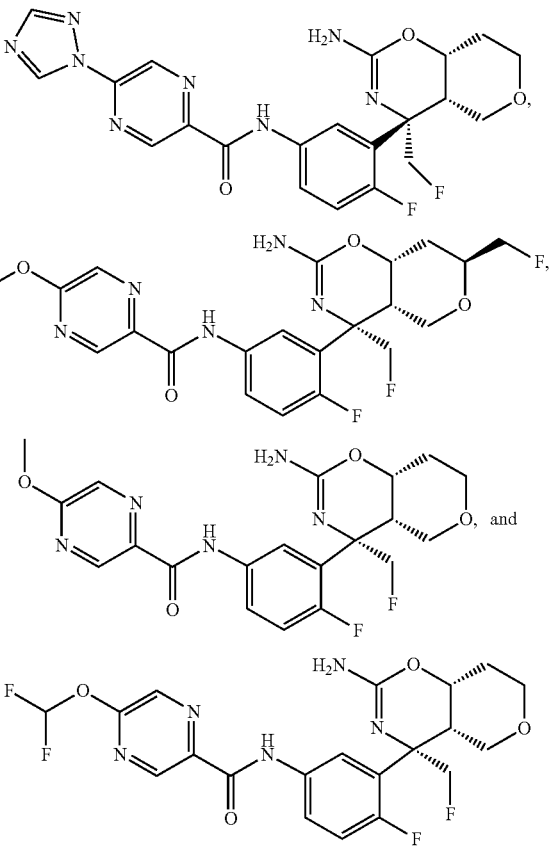

or a pharmaceutically acceptable salt thereof.

(10)' The compound according to above (9-2)' selected from the group consisting of:

[Chem. 15]

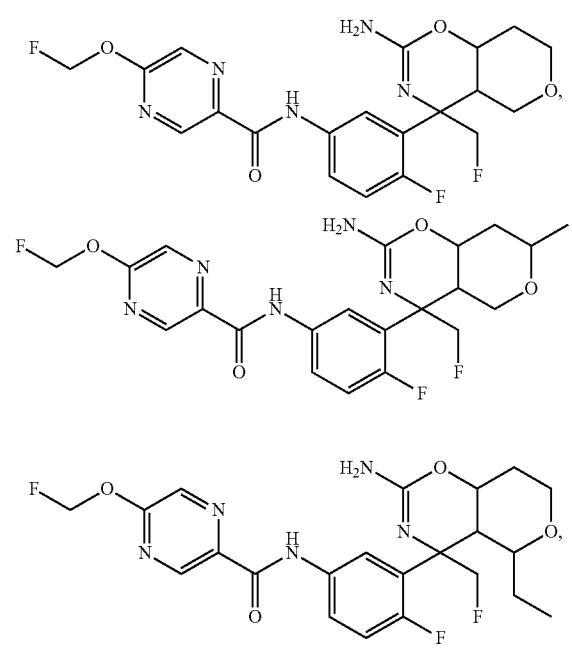

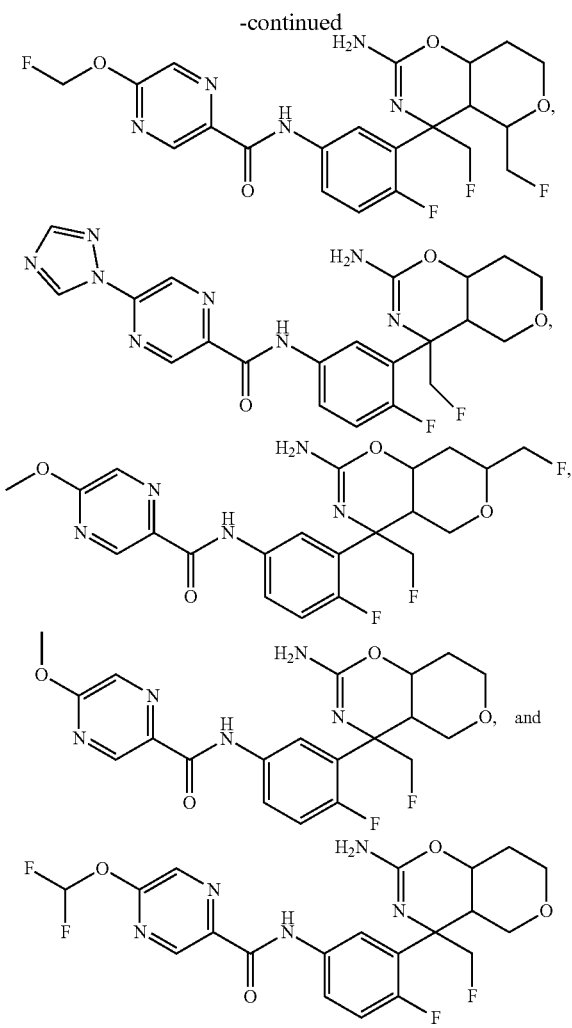

or a pharmaceutically acceptable salt thereof.

(10)'' The compound according to any one of the item (1) to (9), (1)', (2)', (3-2), (4-2), (5-2), (5-3), (7-2), (7-3), (7-4), (8-2), (9-2), (9-2)', (9-3), (9-4), and (9-5), selected from the group consisting of I-007, I-008, I-009, I-010, I-047, I-059, I-067, and I-076, or a pharmaceutically acceptable salt thereof.

(10)''' The compound according to above item (10)', selected from the optical isomers of any one of the compounds described in the above "Chem. 15", or a pharmaceutically acceptable salt thereof.

(1) A pharmaceutical composition comprising the compound according to any one of the items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof.

(12) The pharmaceutical composition having BACE1 inhibitory activity comprising the compound according to the item (1), or a pharmaceutically acceptable salt thereof.

(13) The pharmaceutical composition according to the items (1) or (12), for treating or preventing Alzheimer dementia, mild cognitive impairment or prodromal Alzheimer's disease, for preventing the progression of Alzheimer dementia, mild cognitive impairment, or prodromal Alzheimer's disease, or for preventing the progression in a patient asymptomatic at risk for Alzheimer dementia.

(14) A compound according to any one of the items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4) and (9-5), or a pharmaceutically acceptable salt thereof for use in a method for inhibiting BACE1 activity.

(15) A compound according to any one of the items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof for use in treating or preventing Alzheimer dementia, mild cognitive impairment or prodromal Alzheimer's disease, for use in preventing the progression of Alzheimer dementia, mild cognitive impairment or prodromal Alzheimer's disease, or for use in preventing the progression in a patient asymptomatic at risk for Alzheimer dementia.

(16) A method for inhibiting BACE1 activity comprising administering the compound according to any one of items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5) or a pharmaceutically acceptable salt thereof.

(17) A method for treating or preventing Alzheimer dementia, mild cognitive impairment or prodromal Alzheimer's disease, for preventing the progression of Alzheimer dementia, mild cognitive impairment, or prodromal Alzheimer's disease, or for preventing the progression in a patient asymptomatic at risk for Alzheimer dementia comprising administering the compound according to any one of items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof.

(18) A BACE 1 inhibitor comprising the compound according to any one of items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof.

(19) Use of the compound according to any one of items (1) to (10), (1)', (2)' (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof for manufacturing a medicament for inhibiting BACE1 activity.

(20) The pharmaceutical composition according to the item (11) or (12) for treating or preventing a disease induced by production, secretion or deposition of amyloid ß proteins.

(21) A method for treating or preventing diseases induced by production, secretion or deposition of amyloid ß proteins comprising administering the compound according to any one of items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof.

(22) A compound according to any one of items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof for use in treating or preventing diseases induced by production, secretion or deposition of amyloid ß proteins.

(23) Use of the compound according to any one of items (1) to (10), (1)', (2)', (10)', (10)'', (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof for manufacturing a medicament for treating or preventing diseases induced by production, secretion or deposition of amyloid ß proteins.

(24) The pharmaceutical composition according to the item (1) or (12), for treating or preventing Alzheimer dementia.

(25) A method for treating or preventing Alzheimer dementia comprising administering the compound according to any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof.

(26) A compound according to any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof for use in treating or preventing Alzheimer dementia.

(27) Use of the compound according to any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof for manufacturing a medicament for treating or preventing Alzheimer dementia.

(28) A pharmaceutical composition comprising the compound of any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof, for oral administration.

(29) The pharmaceutical composition of (28), which is a tablet, powder, granule, capsule, pill, film, suspension, emulsion, elixir, syrup, lemonade, spirit, aromatic water, extract, decoction or tincture.

(30) The pharmaceutical composition of (29), which is a sugar-coated tablet, film-coated tablet, enteric-coated tablet, sustained-release tablet, troche tablet, sublingual tablet, buccal tablet, chewable tablet, orally disintegrated tablet, dry syrup, soft capsule, micro capsule or sustained-release capsule.

(31) A pharmaceutical composition comprising the compound of any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof, for parenteral administration.

(32) The pharmaceutical composition of (31), for dermal, subcutaneous, intravenous, intraarterial, intramuscular, intraperitoneal, transmucosal, inhalation, transnasal, ophthalmic, inner ear or vaginal administration.

(33) The pharmaceutical composition of (31) or (32), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(34) A pharmaceutical composition comprising the compound of any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof, for a pediatric or geriatric patient.

(35) A pharmaceutical composition consisting of a combination of the compound of any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof and acetylcholinesterase inhibitor, NMDA antagonist, or other medicament for Alzheimer dementia.

(36) A pharmaceutical composition comprising the compound of any one of items (1) to (10), (1)', (2)', (10)', (10)", (10)''', (3-2), (4-2), (5-2), (5-3), (7-2), (7-3), (7-4), (8-2), (9-2), (9-2)', (9-3), (9-4), and (9-5), or a pharmaceutically acceptable salt thereof, for a combination therapy with acetylcholinesterase inhibitor, NMDA antagonist, or other medicament for Alzheimer dementia.

DESCRIPTION OF EMBODIMENTS

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," "the," and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Each meaning of terms used herein is described below. Both when used alone and in combination unless otherwise noted, each term is used in the same meaning.

In the specification, the term of "consisting of" means having only components.

In the specification, the term of "comprising" means not restricting with components and not excluding undescribed factors.

In the specification, the "halogen" includes fluorine, chlorine, bromine, and iodine. Fluorine and chlorine are preferable. Fluorine is more preferable.

In the specification, the "alkyl" includes linear or branched alkyl of a carbon number of 1 to 15, for example, a carbon number of 1 to 10, for example, a carbon number of 1 to 6, and for example, a carbon number of 1 to 4, preferably a carbon number 1 to 3, and more preferably a carbon number 1 or 2. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. Examples are methyl, ethyl, n-propyl, isopropyl, n-butyl, isobutyl, sec-butyl, tert-butyl and n-pentyl.

In one embodiment, "alkyl" is methyl, ethyl, n-propyl, isopropyl or tert-butyl. Methyl is preferable.

The term of "haloalkyl" includes a group wherein one or more hydrogen atoms attached to one or more carbon atoms of the above "alkyl" are replaced with one or more above "halogen". Examples are monofluoromethyl, monofluoroethyl, monofluoropropyl, difluoromethyl, difluoroethyl, difluoropropyl, trifluoromethyl, trifluoroethyl, trifluoropropyl, pentafluoropropyl, monochloromethyl, monochloroethyl, monochloropropyl, dichloromethyl, dichloroethyl, dichloropropyl, trichloromethyl, trichloroethyl, trichloropropyl, pentachloropropyl, 1-fluoroethyl, 2-fluoroethyl, 1,1-difluoroethyl, 2,2-difluoroethyl, 2,2,2-trifluoroethyl, 1-chloroethyl, 2-chloroethyl, 1,1-dichloroethyl, 2,2-dichloroethyl, 2,2,2-trichloroethyl, 1,2-dibromoethyl, 1,1,1-trifluoropropan-2-yl and 2,2,3,3,3-pentafluoropropyl. Examples are monofluoromethyl, difluoromethyl, trifluoromethyl, 1-fluoroethyl, 1,1-difluoroethyl, and 2,2-difluoroethyl. Examples are monofluoromethyl, difluoromethyl, 1-fluoroethyl, 1,1-difluoroethyl and 2,2-difluoroethyl. Difluoromethyl, trifluoromethyl and 2,2-difluoroethyl are preferable.

The term "alkenyl" includes linear or branched alkenyl of a carbon number or 2 to 15, for example, a carbon number of 2 to 10, for example, a carbon number of 2 to 6, and for example, a carbon number of 2 to 4, having one or more double bonds at any available positions. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl. Examples are vinyl, allyl, propenyl, isopropenyl and butenyl.

The term "alkynyl" includes a linear or branched alkynyl of a carbon number of 2 to 15, for example, a carbon number of 2 to 10, for example, a carbon number of 2 to 8, for example, a carbon number of 2 to 6, and for example, a carbon number of 2 to 4 having one or more triple bonds at optionally positions. Specific examples are ethynyl, propynyl, butynyl, pentynyl, hexynyl, heptynyl, octynyl, nonynyl and decynyl. These may have further a double bond at any available position. Examples are ethynyl, propynyl, butynyl and pentynyl.

The term "alkylene" include a linear or branched divalent carbon chain of a carbon number of 1 to 15, for example, a carbon number of 1 to 10, for example, a carbon number of 1 to 6, and for example a carbon number of 1 to 3. Examples are methylene, dimethylene, and trimethylene.

One or more hydrogens of the alkylene in a compound of formula (I), (IA), or (IB) can be replaced with an isotope of hydrogen $^2$H (deuterium).

The term of "alkyloxy" includes a group wherein an oxygen atom is substituted with the above "alkyl". Examples are methyloxy, ethyloxy, n-propyloxy, isopropyloxy, n-butyloxy, tert-butyloxy, isobutyloxy, sec-butyloxy, pentyloxy, isopentyloxy and hexyloxy.

In one embodiment, "alkyloxy" is methyloxy, ethyloxy, n-propyloxy, isopropyloxy or tert-butyloxy.

The term of "alkenyloxy" includes a group wherein an oxygen atom is substituted with the above "alkenyl". Examples are vinyloxy, allyloxy, 1-propenyloxy, 2-butenyloxy, 2-pentenyloxy, 2-hexenyloxy, 2-heptenyloxy and 2-octenyloxy.

The term of "alkynyloxy" includes a group wherein an oxygen atom is substituted with the above "alkynyl". Examples are ethynyloxy, 1-propynyloxy, 2-propynyloxy, 2-butynyloxy, 2-pentynyloxy, 2-hexynyloxy, 2-heptynyloxy and 2-octynyloxy.

In one embodiment, "alkynyloxy" is ethynyloxy, 1-propynyloxy, and 2-propynyloxy.

The term of "carbocycle" includes non-aromatic carbocycle and aromatic carbocycle.

The term of "non-aromatic carbocycle" includes saturated carbocycle or unsaturated non-aromatic carbocycle which is monocyclic or which consists of two or more rings. A "non-aromatic carbocycle" of two or more rings includes a fused cyclic group wherein a non-aromatic monocyclic carbocycle or a non-aromatic carbocycle of two or more rings is fused with a ring of the above "aromatic carbocycle".

In addition, the "non-aromatic carbocycle" also includes a cyclic group having a bridge or a cyclic group to form a spiro ring as follows:

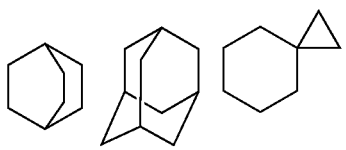

[Chem. 16]

The term "non-aromatic monocyclic carbocycle" includes a group having 3 to 16 carbon atoms, for example, 3 to 12 carbon atoms, for example, 3 to 8 carbon atoms, and for example, 3 to 5 carbon atoms. Examples are cyclopropane, cyclobutane, cyclopentane, cyclohexane, cycloheptane, cyclooctane, cyclononane, cyclodecane, cyclopropene, cyclobutene, cyclopentene, cyclohexene, cycloheptene and cyclohexadiene.

Examples of non-aromatic carbocycle consisting of two or more rings include a group having 6 to 14 carbon atoms, and examples are indane, indenane, acenaphthalene, tetrahydronaphthale and fluorenane.

The term of "aromatic carbocycle" includes an aromatic hydrocarbon ring which is monocyclic or which consists of two or more rings. Examples are an aromatic hydrocarbon group of a carbon number of 6 to 14, and specific examples are benzene, naphthalene, anthracene and phenanthrene.

In one embodiment, "aromatic carbocycle" is benzene.

In one embodiment, "carbocycle" is cyclopropane, cyclobutane and cyclopentane.

The term of "heterocycle" includes non-aromatic heterocycle and aromatic heterocycle.

The term of "non-aromatic heterocycle" includes a non-aromatic group which is monocyclic, or which consists of two or more rings, containing one or more of heteroatoms selected independently from oxygen, sulfur and nitrogen atoms.

A "non-aromatic heterocycle" of two or more rings includes a fused cyclic group wherein non-aromatic monocyclic heterocycle or non-aromatic heterocycle of two or more rings is fused with a ring of the above "aromatic carbocycle", "non-aromatic carbocycle" and/or "aromatic heterocycle".

In addition, the "non-aromatic heterocycle" also includes a cyclic ring having a bridge or a cyclic group to form a spiro ring as follows:

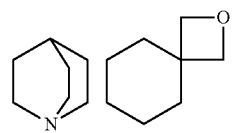

[Chem. 17]

The term "non-aromatic monocyclic heterocycle" includes a 3- to 8-membered ring, and for example, 4-, 5- or 6-membered ring. Examples are dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholinyl, morpholine, thiomorpholine, dihydropyridine, tetrahydropyridine, tetrahydrofurane, tetrahydropyrane, dihydrothiazoline, tetrahydrothiazoline, tetrahydroisothiazoline, dihydrooxazine, hexahydroazepine, tetrahydrodiazepine, tetrahydropyridazine, hexahydropyrimidine, dioxolane, dioxazine, aziridine, dioxoline, oxepane, thiolane, thiine and thiazine.

Examples of non-aromatic heterocycle of two or more rings includes a 9 to 14-membered group, and examples are indoline, isoindoline, chromane and isochromane.

The term of "aromatic heterocycle" includes an aromatic ring which is monocyclic, or which consists of two or more rings, containing one or more of heteroatoms selected independently from oxygen, sulfur and nitrogen atoms.

An "aromatic heterocycle" of two or more rings includes a fused cyclic group wherein aromatic monocyclic heterocyclyl or non-aromatic heterocycle consisting of two or more rings is fused with a ring of the above "aromatic carbocycle".

The term "aromatic monocyclic heterocycle" includes a 5- to 8-membered group, and for example, 5- to 6-membered ring. Examples are pyrrole, imidazole, pyrazole, pyridine, pyridazine, pyrimidine, pyrazine, triazole, triazine, tetrazole, furane, thiophene, isoxazole, oxazole, oxadiazole, isothiazole, thiazole and thiadiazole.

Examples of aromatic bicyclic heterocycle includes a 9- to 10-membered ring, and examples are indoline, isoindoline, indazoline, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofurane, isobenzofurane, benzothiophene, benzotriazole, imidazopyridine, triazolopyridine, imidazothiazole, pyrazinopyridazine, oxazolopyridine and thiazolopyridine.

Examples of aromatic heterocycle of three or more rings includes a 13 to 14-membered group, and examples are carbazole, acridine, xanthene, phenothiazine, phenoxathiine phenoxazine and dibenzofurane.

In one embodiment, "heterocycle" is 1,4-oxathiane.

Examples of substituents of "substituted or unsubstituted alkyl" are one or more groups selected from the following substituent group α.

The substituent group α is a group consisting of halogen, hydroxy, cyano, alkyloxy, The substituents of "substituted or unsubstituted alkyl" are, for example, halogen and the like.

The substituents of "substituted or unsubstituted alkyl" in $R^2$ are for example, halogen and the like.

The substituents of "substituted or unsubstituted alkyl" in $R^3$ are for example, halogen, alkyloxy and the like.

Examples of substituents of "substituted or unsubstituted alkyloxy" are one or more groups selected from the following substituent group B. The substituent group β is a group consisting of halogen, hydroxy, cyano, optionally substituted alkyl (substituents: hydroxy, non-aromatic carbocyclyl, cyano non-aromatic carbocyclyl, halo non-aromatic carbocyclyl, non-aromatic heterocyclyl, alkyl non-aromatic heterocyclyl, halo non-aromatic heterocyclyl, aromatic heterocyclyl).

The substituents of "substituted or unsubstituted alkyl" in $R^2$ are for example, halogen and the like.

The substituents of "substituted or unsubstituted alkyl" in $R^3$ are for example, halogen, alkyloxy and the like.

The substituents of "substituted or unsubstituted alkyloxy" in Ra are, for example, optionally substituted alkyl (substituents: hydroxy, non-aromatic carbocyclyl, cyano non-aromatic carbocyclyl, halo non-aromatic carbocyclyl, non-aromatic heterocyclyl, alkyl non-aromatic heterocyclyl, halo non-aromatic heterocyclyl, aromatic heterocycly), and the like.

A "substituted or unsubstituted non-aromatic carbocyclyl" and "substituted or unsubstituted non-aromatic heterocyclyl" can be substituted with "oxo". A group wherein two hydrogen atoms attached to the same carbon atom are replaced with oxo as follows is included:

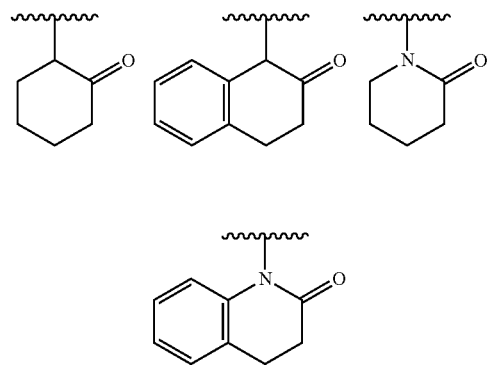

[Chem. 18]

Examples of the substituent of "substituted or unsubstituted carbocycle" or "substituted or unsubstituted heterocycle" include a group selected from the substituent group α.

The compound of formula (I), (IA) or (IB) is not limited to a specific isomer, and includes all possible isomers such as keto-enol isomers, imine-enamine isomers, diastereoisomers, optical isomers and rotation isomers, racemate and the mixture thereof. For example, the compound of formula (I) includes the following tautomers.

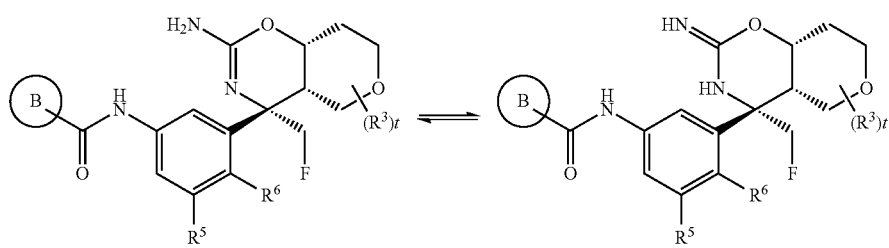

[Chem. 19]

In this description, the group represented by the following formula:

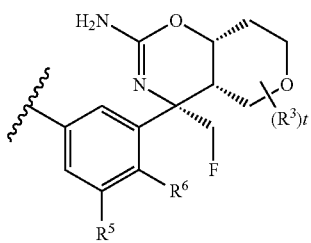

[Chem. 20]

means the group represented by the following formula:

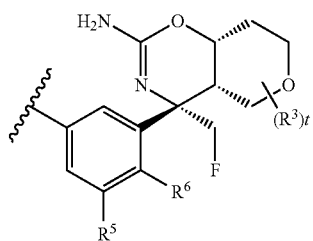

[Chem. 21]

One or more hydrogen, carbon and/or other atoms of a compound of formula (I), (IA) or (IB) can be replaced with an isotope of hydrogen, carbon and/or other atoms, respectively. Examples of isotopes include isotopes of hydrogen, carbon, nitrogen, oxygen, phosphorous, sulfur, fluorine, iodine and chlorine, such as $^2$H (D), $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl, respectively. The compound of formula (I), (IA) or (IB) also includes the compound replaced with such isotopes. The compound replaced with such isotopes is useful also as a medicament, and includes all the radiolabeled compounds of the compound of formula (I), (IA) or (IB). The invention includes "radiolabelling method" for manufacturing the "radiolabeled compound" and the method is useful as a tool of metabolic pharmacokinetic research, the research in binding assay and/or diagnosis. A radiolabeled compound of the compound of formula (I), (IA) or (IB) can be prepared by methods known in the art. For example, tritiated compounds of formula (I), (IA) or (IB) can be prepared by introducing tritium into the particular compound of formula (I), (IA) or (IB) such as by catalytic dehalogenation with tritium. This method may include reacting a suitably halogenated precursor of a compound of formula (I), (IA) or (IB) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). A $^{14}$C-labeled compound can be prepared by employing starting materials having $^{14}$C carbon.

As pharmaceutically acceptable salt of the compound of formula (I), (IA) or (IB), examples include salts with alkaline metals (e.g. lithium, sodium and potassium), alkaline earth metals (e.g. calcium and barium), magnesium, transition metal (e.g. zinc and iron), ammonia, organic bases (e.g. trimethylamine, triethylamine, dicyclohexylamine, ethanolamine, diethanolamine, triethanolamine, meglumine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroiodic acid) and organic acids (e.g. formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid and ethanesulfonic acid). Specific Examples are salts with hydrochloric acid, sulfuric acid, phosphoric acid, tartaric acid, succinic acid, or methanesulfonic acid. These salts can be formed by the usual method.

The compounds of the present invention represented by formula (I), (IA) or (IB) or pharmaceutically acceptable salts thereof may form solvates (e.g., hydrates etc.) and/or crystal polymorphs. The present invention encompasses those various solvates and crystal polymorphs. "Solvates" may be those wherein any number of solvent molecules (e.g., water molecules etc.) are coordinated with the compounds represented by formula (I), (IA) or (IB). When the compounds represented by formula (I) or pharmaceutically acceptable salts are allowed to stand in the atmosphere, the compounds may absorb water, resulting in attachment of adsorbed water or formation of hydrates. Recrystallization of the compounds represented by formula (I) or pharmaceutically acceptable salts may produce crystal polymorphs.

The compounds of the present invention represented by formula (I), (IA) or (IB) or pharmaceutically acceptable salts thereof may form prodrugs. The present invention also encompasses such various prodrugs. Prodrugs are derivatives of the compounds of the present invention that have chemically or metabolically degradable groups and are compounds that are converted to the pharmaceutically active compounds of the present invention through solvolysis or under physiological conditions in vivo. Prodrugs include compounds that are converted to the compounds represented by formula (I), (IA) or (IB) through enzymatic oxidation, reduction, hydrolysis and the like under physiological conditions in vivo and compounds that are converted to the compounds represented by formula (I), (IA) or (IB) through hydrolysis by gastric acid and the like. Methods for selecting and preparing suitable prodrug derivatives are described, for example, in the Design of Prodrugs, Elsevier, Amsterdam 1985. Prodrugs themselves may be active compounds.

When the compounds of formula (I), (IA) or (IB) or pharmaceutically acceptable salts thereof have a hydroxy group, prodrugs include acyloxy derivatives and sulfonyloxy derivatives which can be prepared by reacting a compound having a hydroxy group with a suitable acid halide, suitable acid anhydride, suitable sulfonyl chloride, suitable sulfonylanhydride and mixed anhydride or with a condensing agent. Examples are $CH_3COO^-$, $C_2H_5COO^-$, t-Bu-COO$^-$, $C_{15}H_{31}COO^-$, PhCOO$^-$, (m-NaOOCPh)COO$^-$, NaOOCCH$_2$CH$_2$COO$^-$, CH$_3$CH(NH$_2$)COO$^-$, CH$_2$N(CH$_3$)$_2$COO$^-$, CH$_3$SO$_3^-$, CH$_3$CH$_2$SO$_3^-$, CF$_3$SO$_3^-$, CH$_2$FSO$_3^-$, CF$_3$CH$_2$SO$_3^-$, p-CH—O-PhSO$^-$, PhSO$_3^-$ and p-CH$_3$PhSO$_3^-$.

The compounds of formula (I), (IA) or (IB) may be prepared by the methods described below, together with synthetic methods known to a person skilled in the art.

The starting materials are commercially available or may be prepared in accordance with known methods.

During any of the following synthesis, it may be necessary or preferable to protect sensitive or reactive groups on any of molecules. In such case, these protections can be achieved by means of conventional protective groups such as those described in Greene's Protective Group in Organic Synthesis, John Wily & Sons, 2007.

It will be understood by a person skilled in the art that the compounds described below will be generated as a mixture of diastereomers and/or enantiomers, which may be separated at relevant stages of the following procedures using conventional techniques such as crystallization, silica gel chromatography, chiral or achiral high performance liquid chromatography (HPLC), and chiral supercritical fluid (SFC) chromatography to provide the single enantiomers of the invention.

During all the following steps, the order of the steps to be performed may be appropriately changed. In each step, an intermediate may be isolated and then used in the next step. All of reaction time, reaction temperature, solvents, reagents, and protecting groups, etc. are mere exemplification and not limited as long as they do not cause an adverse effect on a reaction.

General Procedure A

[Chem. 22]

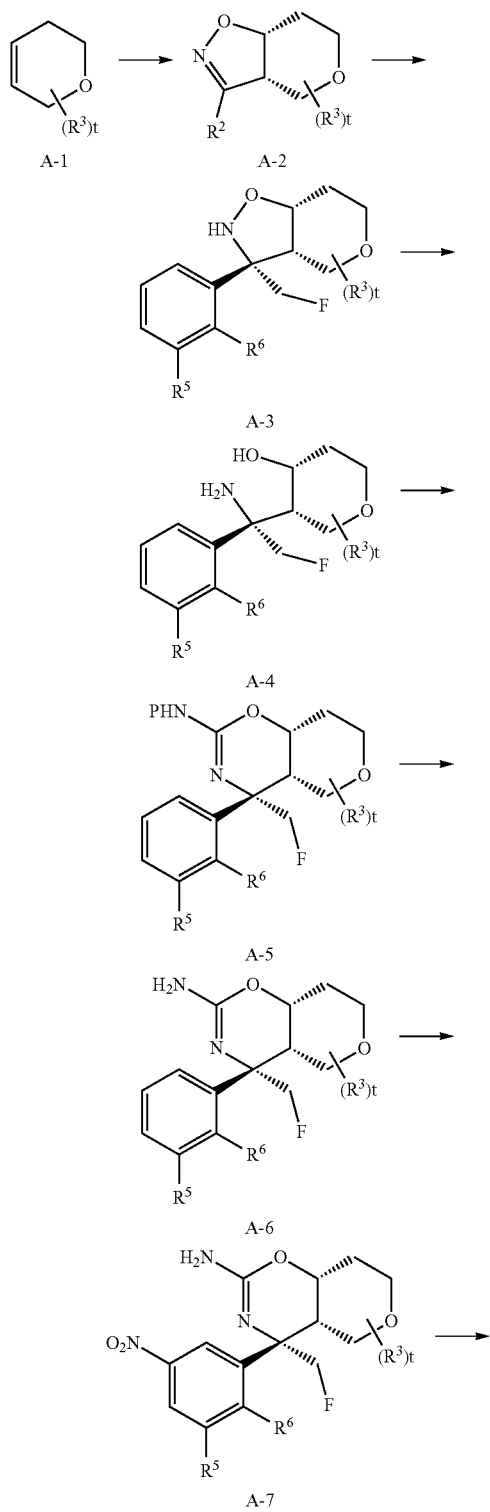

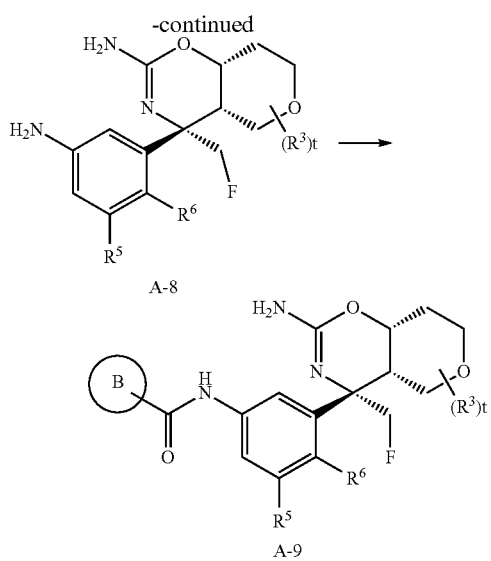

Wherein P is a protective group such as benzoyl or benzyl and the other symbols are the same as defined above (1).

General Procedure A is a method for preparing compounds of Compound A-9 from Compounds A-1 through multiple steps of Step 1 to Step 8. Those skilled in the art will be appreciate that protective groups P can be chosen depending on the reaction conditions used in later steps.

Step 1

Compound A-2 can be prepared by means of 1,3-dipolar cycloaddition. This type of reactions can be conducted using similar conditions described in J. Am. Chem. Soc., 1960, 82, 5339-5342 or J. Org. Chem. 1998, 63, 5272-5274. These 1,3-dipolar cycloadditions can be conducted with cyclic Compound A-1 and the corresponding nitrile oxides generated in situ from the corresponding nitroalkanes using an appropriate dehydrating agents such as, for example, phenyl isocyanate, pheyl diisocyanate or $(Boc)_2O$, and an appropriate base such as, for example, triethylamine, dipropylethylamine or N-methylmorpholine. Alternatively, the nitrile oxides can be generated in situ from the corresponding hydroximoyl chlorides with an appropriate base such as, for example, triethylamine, dipropylethylamine or N-methylmorpholine. The solvent used in this step is not particularly limited in so far as it does not interfere with the reaction. Examples of the solvent include tetrahydrofuran, 1,4-dioxane, 1,2-dimethoxyethane, diethyl ether, toluene, benzene, and mixed solvents thereof. The reaction temperature is preferably room temperature to 120° C. The reaction time is not particularly limited and is usually 5 minutes to 24 hours, preferably 30 minutes to 24 hours.

Step 2

Compound A-3 can be prepared by means of the nucleophilic addition of an appropriate aryllithium reagents or Grignard reagents to Compound A-2. This type of reactions can be conducted using similar conditions described in J. Am. Chem. Soc., 2005, 127, 5376-5384. Preferably, the aryllithium reagents or Grignard reagents can be prepared from the corresponding aromatic halides using an appropriate base, such as, for example, n-, sec- or tert-butyl lithium, isopropylmagnesium bromide or metallic magnesium, which can be then reacted to Compound A-2 with Lewis acid such as, for example, $BF_3$-$OEt_2$ to give Compound A-3. The solvent used in this step is not particularly limited in so far as it does not interfere with the reaction. Examples of the solvent include tetrahydrofuran, 1,4-dioxane, 1,2-dimethoxyethane, diethyl ether, toluene, benzene, and mixed solvents thereof. The reaction temperature is preferably −78° C. to room temperature. The reaction time is not particularly limited and is usually 5 minutes to 24 hours, preferably 30 minutes to 24 hours.

Step 3

Compound A-4 can be prepared by reductive cleavage reaction of the N—O bond of compound A-3. This reductive cleavage can be conducted using zinc with an appropriate acid such as acetic acid, formic acid or hydrochloric acid. The solvent used in this step is not particularly limited in so far as it does not interfere with the reaction. Examples of the solvent include methanol, ethanol, tetrahydrofuran, water and mixed solvents thereof. The reaction temperature is preferably −20° C. to solvent reflux temperature. The reaction time is not particularly limited and is usually 5 minutes to 24 hours, preferably 30 minutes to 24 hours.

Alternatively, this reaction can be performed using a metal catalyst such as platinum oxide under hydrogen. The solvent used in this step is not particularly limited in so far as it does not interfere with the reaction. Examples of the solvent include methanol, ethanol, water and mixed solvents thereof. The reaction temperature is preferably room temperature to 50° C. The reaction time is not particularly limited and is usually 5 minutes to 24 hours, preferably 30 minutes to 24 hours.

Furthermore, this type of reaction can also be conducted using lithium aluminum hydride. The solvent used in this step is not particularly limited in so far as it does not interfere with the reaction. Examples of the solvent include tetrahydrofuran, 1,4-dioxane, 1,2-dimethoxyethane, diethyl ether and mixed solvents thereof. The reaction temperature is preferably −20° C. to room temperature. The reaction time is not particularly limited and is usually 5 minutes to 24 hours, preferably 30 minutes to 24 hours.

Step 4

Compound A-5 can be prepared by formation of the corresponding thioureas from Compound A-4 in situ, followed by cyclization reaction. This type of reactions is known to a person skilled in the art and can be performed under the conditions described in WO2014/065434. The thiourea can be obtained in situ from Compound A-4 using an appropriate isothiocyanates such as, for example benzoyl isothiocyanate or benzyl isothiocyanate, then cyclization can be performed by adding reagents such as, for example m-CPBA, hydrogene peroxide, or carbodiimide reagents (e. g. DCC, DIC or EDC). Alternatively, this cyclization can be performed using alkylating reagents such as methyl iodide, and an appropriate base such as sodium hydride, sodium bicarbonate and potassium carbonate. The solvent used in this step is not particularly limited in so far as it does not interfere with the reaction. Examples of the solvent include chloroform, dichloromethane, dichloroethane, tetrahydrofuran, and mixed solvents thereof. The reaction temperature is usually 0° C. to 60° C. The reaction time is not particularly limited and is usually 5 minutes to 24 hours, preferably 30 minutes to 24 hours.

Step 5

Compound A-6 can be prepared by deprotection of Compound A-5. This deprotection reaction is known to a person skilled in the art and can be performed under the conditions described in Green's Protective Groups in Organic Synthesis, $4^{th}$ ed. When the protecting group is benoyl, the deprotecting reaction can be conducted under acidic conditions such as sulfuric acid or hydrochloric acid, or under basic condition such as hydrazine, DBU, or sodium hydroxide. The solvent used in this step is not particularly limited in so far as it does not interfere with the reaction. Examples of the solvent include dichloromethane, tetrahydrofuran, 1,4-dioxane, methanol, toluene, benzene and mixed solvents thereof. The reaction temperature is preferably room temperature to 100° C. The reaction time is not particularly limited and is usually 5 minutes to 24 hours, preferably 30 minutes to 24 hours.

Step 6

Compound A-7 can be prepared by nitration of Compound A-6. A typical procedure involves the treatment of Compound A6 dissolved in sulfuric acid and trifluoroacetic acid, with a source of nitronium ion, such as, for example, potassium nitrate or nitric acid. The reaction temperature is preferably −20° C. to 0° C. The reaction time is not particularly limited and is usually 5 minutes to 5 hours, preferably 30 minutes to 2 hours.

Step 7

Compound A-8 can be prepared by reduction of Compound A-7. The reduction can be conducted by a suitable catalyst, such as, for example, palladium on carbon under hydrogen atmosphere, or the use of a reducing agent such as, for example, iron, zinc or tin(II) chloride. The solvent used in this step is not particularly limited in so far as it does not interfere with the reaction. Examples of the solvent include tetrahydrofuran, methanol, ethanol, water, and mixed solvents thereof. The reaction temperature is usually room temperature to 80° C. and is preferably room temperature to 60° C. The reaction time is not particularly limited and is usually 5 minutes to 24 hours, preferably 30 minutes to 24 hours.

Step 8

Compound A-9 can be prepared by amide coupling reaction of an appropriate acid salt of Compound A-8 with the corresponding carboxylic acids. The acid salt of Compound A can be prepared with one equivalent of an appropriate acid such as HCl before conducting condensation reaction. This reaction can be conducted by a method known to a person skilled in the art, and suitable coupling conditions can be found in Chem. Rev. 2011, 111, 6557-6602, which includes: a) reactions using condensation reagents; b) reactions using acid chlorides or fluorides. This reaction must be conducted without addition of any base for chemoselective amide coupling on the aniline position.

Reaction a) can be conducted by use of condensation reagents such as dicyclohexylcarbodiimide (DCC), diisopropylcarbodiimide (DIC), 1-ethyl-3-(3-dimethylaminopropyl) carbodiimide hydrochloride (EDC hydrochloride), 0-(7-aza-1H-benzotriazol-1-yl)-N,N,N',N'-tetramethyluronium hexafluorophosphate (HATU), and 1H-Benzotriazol-1-yloxy-tri(pyrrolidino) phosphonium hexafluorophosphate (PyBOP). When using uronium or phosphonium salts such as HATU and PyBOP, the reaction can be performed in the presence of bases such as triethylamine and diisopropylethylamine. The reaction may be accelerated by use of catalysts such as 1-hydroxy-benzotriazole (HOBt) and 1-hydroxy-7-aza-benzotriazole (HOAt). The solvent used in the reaction is not particularly limited in so far as it does not interfere with the reaction. Examples of the solvent include dichloromethane, N,N-dimethylformamide (DMF), N-methylpyrrolidone (NMP), and tetrahydrofuran. The reaction temperature is usually 0° C. to 50° C. and is preferably room temperature.

Reaction b) can be performed by use of commercially available acid chlorides or those synthesized by known methods to a person skilled in the art in solvents such as dichloromethane, tetrahydrofuran, and ethyl acetate in the presence of bases such as triethylamine, diisopropylethylamine, pyridine, and N,N-dimethyl-4-aminopyridine. The reaction temperature is usually 0° C. to 60° C. and is preferably 0° C. to room temperature. The reaction time is not particularly limited and is usually 5 minutes to 24 hours, preferably 20 minutes to 6 hours.

General Procedure R

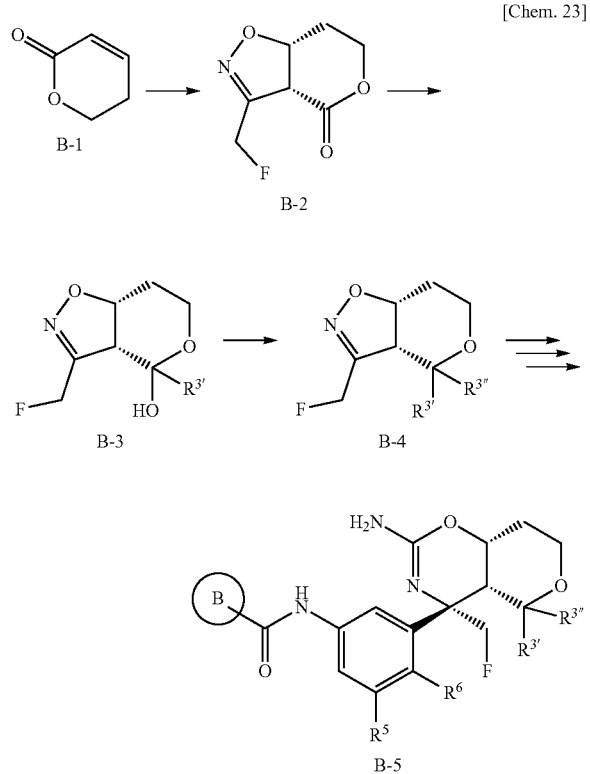

[Chem. 23]

Wherein $R^{3'}$ and $R^{3''}$ are each independently selected from the group consisting of alkyl optionally substituted with halogen, cyano, alkyloxy, haloalkyloxy or non-aromatic carbocyclyl, and heterocyclyl optionally substituted with alkyl, and other symbols are the same as defined above.

General Procedure B is a method for preparing Compound B-5 from Compound B-1 through multiple steps. Using Compound B-4 and Compound B-5 can be prepared according to the methods described in General procedure A.

Step 1

Compound B-2 can be prepared by means of 1,3-dipolar cycloaddition. This type of reactions can be conducted using similar conditions described in J. Am. Chem. Soc. 1960, 82, 5339-5342 or J. Org. Chem. 1998, 63, 5272-5274. These 1,3-dipolar cycloadditions can be conducted with cyclic Compound B-1 and the corresponding nitrile oxides generated in situ from the corresponding nitroalkanes using an appropriate dehydrating agents such as, for example, phenyl isocyanate, pheyl diisocyanate or (Boc)₂O, and an appropriate base such as, for example, triethylamine, diisopropylethylamine or N-methylmorpholine. Alternatively, the nitrile oxides can be generated in situ from the corresponding hydroximoly chlorides with an appropriate base such as, for example, triethylamine, diisopropylethylamine or N-methylmorpholine. The solvent used in this step is not particularly limited in so far as it does not interfere with the reaction. Examples of the solvent include tetrahydrofuran, 1,4-dioxane, 1,2-dimethoxyethane, diethyl ether, toluene, benzene, and mixed solvents thereof. The reaction temperature is preferably room temperature to 120° C. The reaction time is not particularly limited and is usually 5 minutes to 24 hours, preferably 30 minutes to 24 hours.

Step 2

When $R^{3'}$ is a hydrogen atom, Compound B-3 can be prepared by carbonyl reduction of Compound B-2. This type of reactions can be conducted using an appropriate metal hydrides such as, for example, DIBAL-H, lithium tri-tert-butoxyaluminum hydride or sodium bis(2-methoxyethoxy) aluminum hydride, by means of the nucleophilic hydride addition to Compound B-2. The solvent used in this step is not particularly limited in so far as it does not interfere with the reaction. Examples of the solvent include dichloromethane, tetrahydrofuran, 1,4-dioxane, 1,2-dimethoxyethane, diethyl ether, toluene, benzene, and mixed solvents thereof. The reaction temperature is preferably −78° C. to room temperature. The reaction time is not particularly limited and is usually 5 minutes to 24 hours, preferably 30 minutes to 24 hours.

When $R^{3'}$ is other than a hydrogen atom, Compound B-3 can be prepared by means of the nucleophilic addition to Compound B-2. This type of reactions can be conducted using an appropriate nucleophiles such as, for example organic lithium, magnesium, zinc or silyl reagents, with or without Lewis acid such as, for example $BF_3$-$OEt_2$. $AlCl_3$ or $TiCl_4$. The solvent used in this step is not particularly limited in so far as it does not interfere with the reaction. Examples of the solvent include dichloromethane, tetrahydrofuran, 1,4-dioxane, 1,2-dimethoxyethane, diethyl ether, toluene, benzene, and mixed solvents thereof. The reaction temperature is preferably −78° C. to room temperature. The reaction time is not particularly limited and is usually 5 minutes to 24 hours, preferably 30 minutes to 24 hours.

Step 3

When $R^{3''}$ is a hydrogen atom, Compound B-4 can be prepared by reduction of Compound B-3. This type of reactions can be conducted using an appropriate redusing agents such as triethylsilane, sodium borohydride with or without Lewis acid such as $BF_3$-$OEt_2$. The solvent used in this step is not particularly limited in so far as it does not interfere with the reaction. Examples of the solvent include dichloromethane, acetonitrile, tetrahydrofuran, 1,4-dioxane, 1,2-dimethoxyethane, diethyl ether, toluene, benzene, and mixed solvents thereof. The reaction temperature is preferably −20° C. to room temperature. The reaction time is not particularly limited and is usually 5 minutes to 24 hours, preferably 30 minutes to 24 hours.

When $R^{3''}$ is other than a hydrogen atom, Compound B-4 can be prepared by means of the nucleophilic addition to Compound B-2. This type of reactions can be conducted using an appropriate nucleophiles such as, for example organic lithium, magnesium, zinc or silyl reagents, with or without Lewis acid such as, for example $BF_3$-$OEt_2$. $AlCl_3$ or $TiCl_4$. The solvent used in this step is not particularly limited in so far as it does not interfere with the reaction. Examples of the solvent include dichloromethane, tetrahydrofuran, 1,4-dioxane, 1,2-dimethoxyethane, diethyl ether, toluene, benzene, and mixed solvents thereof. The reaction temperature is preferably −78° C. to room temperature. The reaction time is not particularly limited and is usually 5 minutes to 24 hours, preferably 30 minutes to 24 hours.

General Procedure C

[Chem. 24]

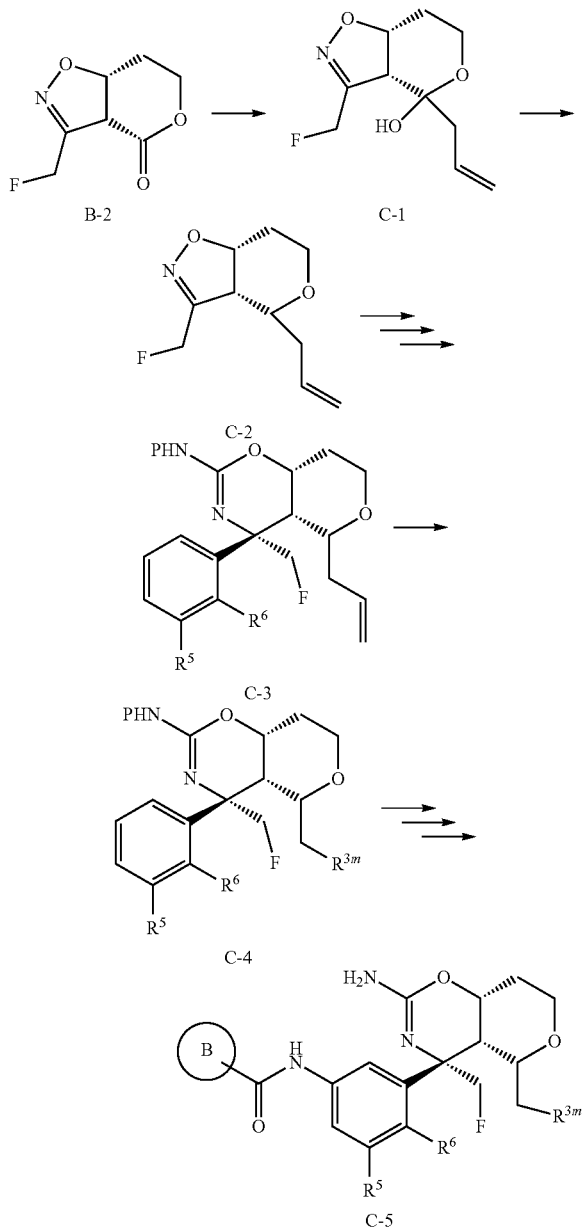

Wherein P is a protective group such as benzoyl or benzyl, $R^{3'''}$ is ethyl or cyclopropyl, and the other symbols are the same as defined above (1). General Procedure C is a method for preparing Compound C-5 from Compound B-1 through multiple steps. Compound C-3 and Compound C-5 can be prepared from Compound C-2 and C-5 according to the methods described in General procedure A.

Step 1

Compound C-1 can be prepared by means of the nucleophilic addition of allyl moiety to carbonyl group of Compound B-2. This type of reactions can be conducted using an appropriate commercially available or in situ generated allyl reagents such as, for example allyl silane, lithium, magnesium, zinc reagents, with or without Lewis acid such as, for example $BF_3$-$OEt_2$, $AlCl_3$ or $TiCl_4$. The solvent used in this step is not particularly limited in so far as it does not interfere with the reaction. Examples of the solvent include dichloromethane, tetrahydrofuran, 1,4-dioxane, 1,2-dimethoxyethane, diethyl ether, toluene, benzene, and mixed solvents thereof. The reaction temperature is preferably −78° C. to room temperature. The reaction time is not particularly limited and is usually 5 minutes to 24 hours, preferably 30 minutes to 24 hours.

Step 2

Compound C-2 can be prepared by reduction of Compound C-1. This type of reactions can be conducted using an appropriate reducing agents such as triethylsilane or sodium borohydride, with or without Lewis acid such as $BF_3$-$OEt_2$. The solvent used in this step is not particularly limited in so far as it does not interfere with the reaction. Examples of the solvent include dichloromethane, acetonitrile, tetrahydrofuran, 1,4-dioxane, 1,2-dimethoxyethane, diethyl ether, toluene, benzene, and mixed solvents thereof. The reaction temperature is preferably −20° C. to room temperature. The reaction time is not particularly limited and is usually 5 minutes to 24 hours, preferably 30 minutes to 24 hours.

Step 3

When $R^{3'''}$ is ethyl, Compound C-5 can be obtained by hydrogenation of Compound C-4. The hydrogenation can be performed using suitable catalyst such as, for example palladium on carbon under hydrogene atmosphere. The solvent used in this step is not particularly limited in so far as it does not interfere with the reaction. Examples of the solvent include tetrahydrofuran, methanol, ethanol, water, and mixed solvents thereof. The reaction temperature is usually room temperature to 80° C. and is preferably room temperature to 60° C. The reaction time is not particularly limited and is usually 5 minutes to 24 hours, preferably 30 minutes to 24 hours.

When $R^{3'''}$ is cyclopropyl, Compound C-5 can be obtained by means of cyclopropanation of Compound C-4. This type of reaction can be performed using an appropriate reagent such as diazomethane with or without a suitable catalyst, or Simmons-Smith reaction condition such as, for example diiodomethane with diethylzinc. The solvent used in this step is not particularly limited in so far as it does not interfere with the reaction. Examples of the solvent include dichloromethane, diethylether, toluene, benzene, or mixed solvents thereof. The reaction temperature is usually −30° C. to room temperature. The reaction time is not particularly limited and is usually 5 minutes to 24 hours, preferably 30 minutes to 24 hours.

General Procedure D

[Chem. 25]

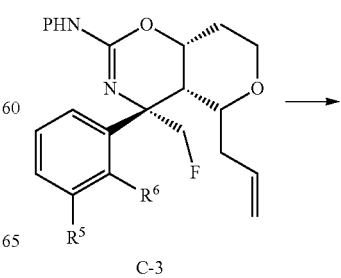

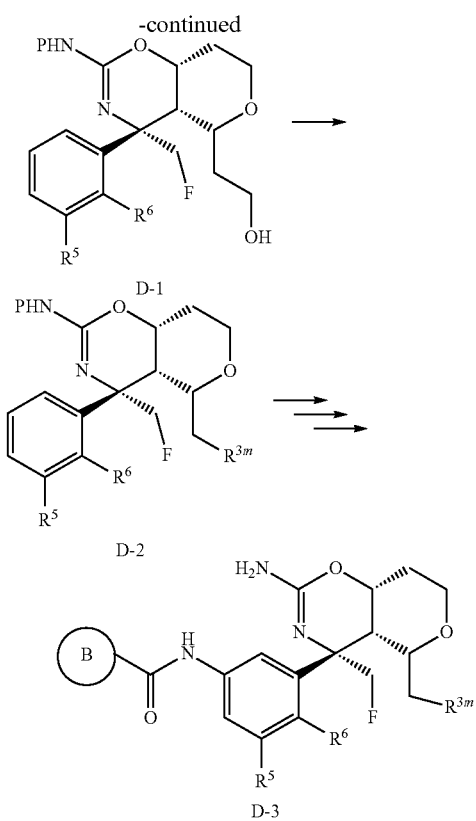

Wherein P is a protective group such as benzoyl or benzyl, $R^{3''''}$ is alkyl substituted with fluorine or alkyloxy, and the other symbols are the same as defined above (1).

General Procedure D is a method for preparing compounds of Compound D-3 from Compound C-3 through multiple steps. Compound D-3 can be prepared from Compound D-2 according to the methods described in General procedure A.

Step 1

Compound D-1 can be prepared by ozonolysis of Compound C-3, followed by reduction of the resulting aldehyde. This reaction can be performed by a method known to a person skilled in the art. The ozonolysis can be performed under ozone atmosphere in suitable solvent such as dichloromethane, methanol, and mixed thereof, with an appropriate regents such as triphenylphosphine, pyridine, dimethylsulfide and trimethylamine under nitrogen atmosphere for reductive workup. The temperature for generation of ozonide is preferably −78° C., then the temperature can be allowed to warm to room temperature for reductive workup. The reaction time is not particularly limited and is usually 30 minutes to 5 hours, preferably 30 minutes to 2 hours. The reduction of the resulting aldehyde can be performed in one pot using an appropriate reducing agent such as sodium borohydride or lithium aluminum hydride. The reaction temperature is preferably 0° C. to room temperature. The reaction time is not particularly limited and is usually 30 minutes to 5 hours, preferably 30 minutes to 2 hours.

Step 2

When $R^{3''''}$ is $CF_3$, $CHF_2$ or $CH_2F$, Compound D-2 can be obtained by two-step sequence; oxidation of Compound D-1 to the aldehyde or carboxylic acid followed by fluorination, or direct fluorination of Compound D-1. This reaction can be performed by a method known to a person skilled in the art.

For example, Compound D-1 can be oxidized to the corresponding aldehyde under an appropriate oxidation condition such as, for example TEMPO, Dess-Martin or Swern oxidation. The corresponding carboxylic acid can be obtained by oxidation of the resulting aldehyde, or oxidizing Compound D-1 directly using an appropriate condition such as for example, Pinnick, TEMPO or Jones oxadation. The solvent used in this step is not particularly limited in so far as it does not interfere with the reaction. The reaction temperature is usually −78° C. to room temperature. The reaction time is not particularly limited and is usually 5 minutes to 24 hours, preferably 30 minutes to 24 hours. The flurorination reaction can be performed using an appropriate reagent such as, for example DAST, Deoxofluor or sulfur tetrafluoride. The solvent used in this step is not particularly limited in so far as it does not interfere with the reaction. Examples of the solvent include dichloromethane, tetrahydrofuran, 1,4-dioxane, 1,2-dimethoxyethane, diethyl ether, toluene, benzene, and mixed solvents thereof. The reaction temperature is preferably −78° C. to 50° C. The reaction time is not particularly limited and is usually 5 minutes to 24 hours, preferably 30 minutes to 24 hours.

When $R^{3''''}$ is alkyloxy, Compound D-2 can be obtained by means of alkylation of the terminal alcohol of Compound D-1. This reaction can be performed using an appropriate base such as sodium hydride with the corresponding electrophiles such as alkyl halide, mesylate or triflate. The solvent used in this step is not particularly limited in so far as it does not interfere with the reaction. Examples of the solvent include acetone, acetonitrile, tetrahydrofuran, DMF, DMA, DMSO, toluene, and mixed solvents thereof. The reaction temperature is preferably 0° C. to 100° C. The reaction time is not particularly limited and is usually 5 minutes to 24 hours, preferably 30 minutes to 24 hours.

General Procedure E

[Chem. 26]

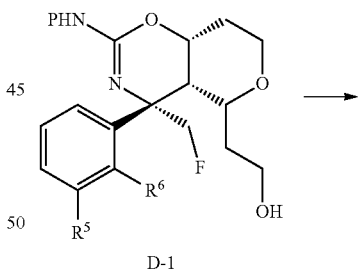

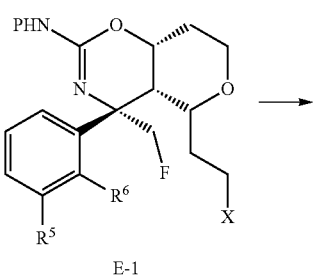

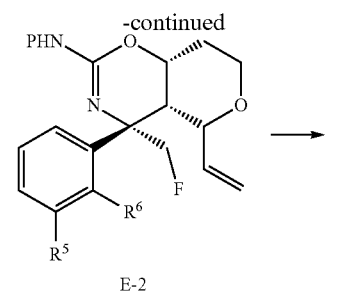

E-2

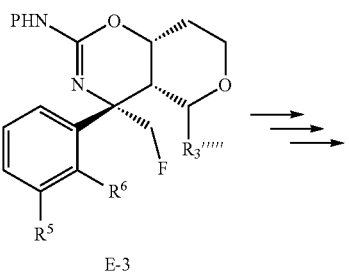

E-3

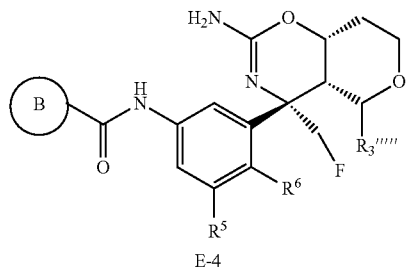

E-4

Wherein P is a protective group such as benzoyl or benzyl, $R^{3'''''}$ is ethyl or cyclopropyl, X is leaving group such as halogen, mesylate or triflate, and other symbols are the same as defined above (1).

General Procedure E is a method for preparing compounds of Compound E-4 from Compound D-1 through multiple steps. Compound E-4 can be prepared from Compound E-2 according to the methods described in General procedure A.

Step 1

Compound E-1 can be prepared by converting the terminal alcohol of Compound D-1 to a leaving group. This reaction can be performed by a method known to a person skilled in the art. Compound E-1 can be obtained under suitable halogenation conditions such as, for example using $SOX_2$, $POX_3$ (X=Cl or Br), or Appel reaction conditions such as triphenylphosphine with $CX_4$ (X=Cl or Br) or iodine. The solvent used in this step is not particularly limited in so far as it does not interfere with the reaction. Examples of the solvent include dichloromethane, tetrahydrofuran, toluene, and mixed solvents thereof. The reaction temperature is preferably 0° C. to 100° C. The reaction time is not particularly limited and is usually 5 minutes to 24 hours, preferably 30 minutes to 24 hours.

Step 2

Compound E-2 can be prepared by converting the terminal alcohol of Compound D-1 to a leaving group. This reaction can be performed by a method known to a person skilled in the art. Compound E-1 can be obtained under suitable halogenation conditions such as, for example using $SOX_2$, $POX_3$ (X=Cl or Br), or Appel reaction conditions such as triphenylphosphine with $CX_4$ (X=Cl or Br) or iodine. The solvent used in this step is not particularly limited in so far as it does not interfere with the reaction. Examples of the solvent include dichloromethane, tetrahydrofuran, toluene, and mixed solvents thereof. The reaction temperature is preferably 0° C. to 100° C. The reaction time is not particularly limited and is usually 5 minutes to 24 hours, preferably 30 minutes to 24 hours.

Step 3

Compound E-2 can be prepared by means of elimination reaction of compound E-1. This reaction can be performed by a method known to a person skilled in the art. Compound E-2 can be obtained using an appropriate base such as for example, sodium or potassium tert-butoxide, triethyamine, diisopropylethylamine, DBU or pyridine. The solvent used in this step is not particularly limited in so far as it does not interfere with the reaction. Examples of the solvent include dichloromethane, tetrahydrofuran, toluene, and mixed solvents thereof. The reaction temperature is preferably 0° C. to 60° C. The reaction time is not particularly limited and is usually 5 minutes to 24 hours, preferably 30 minutes to 24 hours.

Step 4

When $R^{3'''''}$ is ethyl, Compound E-3 can be obtained by hydrogenation of Compound E-2. The hydrogenation can be performed using suitable catalysts such as, for example palladium on carbon under hydrogen atmosphere. The solvent used in this step is not particularly limited in so far as it does not interfere with the reaction. Examples of the solvent include, tetrahydrofuran, methanol, ethanol, water, mixed solvents thereof. The reaction temperature is usually room temperature to 80° C. and is preferably room temperature to 60° C. The reaction time is not particularly limited and is usually 5 minutes to 24 hours, preferably 30 minutes to 24 hours.

When $R^{3'''''}$ is cyclopropyl, Compound E-3 can be obtained by means of cyclopropanation of Compound C-4. This type of reaction can be performed using an appropriate reagent such as diazomethane with or without a suitable catalyst, or Simmons-Smith reaction conditions such as, for example diiodomethane with diethylzinc. The solvent used in this step is not particularly limited in so far as it does not interfere with the reaction. Examples of the solvent include dichloromethane, diethylether, toluene, benzene, or mixed solvents thereof. The reaction temperature is usually −30° C. to room temperature. The reaction time is not particularly limited and is usually 5 minutes to 24 hours, preferably 30 minutes to 24 hours.

General Procedure F

[Chem. 27]

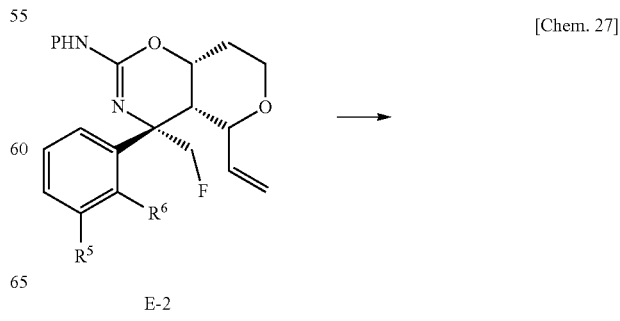

E-2

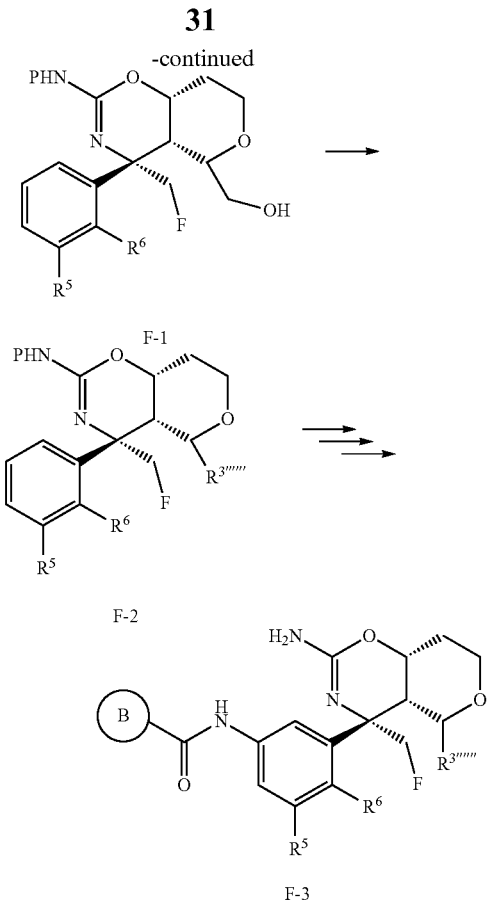

Wherein P is a protective group such as benzoyl or benzyl, R$^{3''''''}$ is alkyl substituted with fluorine or alkyloxy, and other symbols are the same as defined above.

General Procedure F is a method for preparing Compound F-3 from Compounds E2 through multiple steps. Compounds F-3 can be prepared from Compound F-2 according to the methods described in General procedure A.

Step 1

Compound F-1 can be prepared by ozonolysis of Compound F-3, followed by reduction of the resulting aldehyde. This reaction can be performed by a method known to a person skilled in the art. The ozonolysis can be performed under ozone atmosphere in a suitable solvent such as dichloromethane, methanol, and mixed thereof, with an appropriate reagent such as triphenylphosphine, pyridine, dimethylsulfide and trimethylamine under nitrogen atmosphere for reductive workup. The temperature for generation of ozonide is preferably −78° C., then the temperature can be allowed to warm to room temperature for reductive workup. The reaction time is not particularly limited and is usually 30 minutes to 5 hours, preferably 30 minutes to 2 hours. The reduction of the resulting aldehyde can be performed in one pot using an appropriate reducing agent such as sodium borohydride or lithium aluminum hydride. The reaction temperature is preferably 0° C. to room temperature. The reaction time is not particularly limited and is usually 30 minutes to 5 hours, preferably 30 minutes to 2 hours.

Step 2

When R$^{3''''''}$ is CF$_3$, CHF$_2$ or CH$_2$F, Compound F-2 can be obtained by two-step sequence; oxidation of Compound F-1 to the aldehyde or carboxylic acid followed by fluorination, or direct fluorination of Compound F-1. This reaction can be performed by a method known to a person skilled in the art.

For example, Compound F-1 can be oxidized to the corresponding aldehyde under an appropriate oxidation condition such as, for example TEMPO, Dess-Martin or Swern oxidation. The corresponding carboxylic acid can be obtained by oxidation of the resulting aldehyde, or oxidizing Compound F-1 directly using an appropriate condition such as for example, Pinnick, TEMPO or Jones oxadation. The solvent used in this step is not particularly limited in so far as it does not interfere with the reaction. The reaction temperature is usually −78° C. to room temperature. The reaction time is not particularly limited and is usually 5 minutes to 24 hours, preferably 30 minutes to 24 hours. The fluorination reaction can be performed using an appropriate reagent such as, for example DAST, Deoxofluor or sulfur tetrafluoride. The solvent used in this step is not particularly limited in so far as it does not interfere with the reaction. Examples of the solvent include dichloromethane, tetrahydrofuran, 1,4-dioxane, 1,2-dimethoxyethane, diethyl ether, toluene, benzene, and mixed solvents thereof. The reaction temperature is preferably −78° C. to 50° C. The reaction time is not particularly limited and is usually 5 minutes to 24 hours, preferably 30 minutes to 24 hours.

When R$^{3''''''}$ is alkyloxy, Compound F-2 can be obtained by means of alkylation of the terminal alcohol of Compound F-1. This reaction can be performed using an appropriate base such as sodium hydride with the corresponding electrophiles such as alkyl halide, mesylate or triflate. The solvent used in this step is not particularly limited in so far as it does not interfere with the reaction. Examples of the solvent include acetone, acetonitrile, tetrahydrofuran, DMF, DMA, DMSO, toluene, and mixed solvents thereof. The reaction temperature is preferably 0° C. to 100° C. The reaction time is not particularly limited and is usually 5 minutes to 24 hours, preferably 30 minutes to 24 hours.

The compounds of the present invention have BACE1 inhibitory activity and are effective in treatment and/or prevention, symptom improvement, and prevention of the progression of disease induced by the production, secretion or deposition of amyloid ß protein, such as Alzheimer's disease, Alzheimer dementia, senile dementia of Alzheimer type, mild cognitive impairment (MCI), prodromal Alzheimer's disease (e.g., MCI due to Alzheimer's disease), Down's syndrome, memory impairment, prion disease (Creutzfeldt-Jakob disease), Dutch type of hereditary cerebral hemorrhage with amyloidosis, cerebral amyloid angiopathy, other type of degenerative dementia, mixed dementia such as coexist Alzheimer's disease with vascular type dementia, dementia with Parkinson's Disease, dementia with progressive supranuclear palsy, dementia with Corticobasal degeneration, Alzheimer's disease with diffuse Lewy body disease, age-related macular degeneration, Parkinson's Disease, amyloid angiopathy or the like.

Furthermore, the compounds of the present invention are effective in preventing the progression in a patient asymptomatic at risk for Alzheimer dementia (preclinical Alzheimer's disease).

"A patient asymptomatic at risk for Alzheimer dementia" includes a subject who is cognitively and functionally normal but has potential very early signs of Alzheimer's disease or typical age related changes (e.g., mild white matter hyper intensity on MRI), and/or have evidence of amyloid deposition as demonstrated by low cerebrospinal fluid AB-42 levels. For example, "a patient asymptomatic at risk for Alzheimer dementia" includes a subject whose score of the Clinical Dementia Rating (CDR) or Clinical Dementia Rating-Japanese version (CDR-J) is 0, and/or whose stage of the Functional Assessment Staging (FAST) is stage 1 or stage 2.

The compound of the present invention has not only BACE1 inhibitory activity but the beneficialness as a medicament. The compound has, preferably, any one or more of the following superior properties.

a) The compound has weak inhibitory activity for CYP enzymes such as CYP1A2, CYP2C9, CYP2C19, CYP2D6, CYP3A4.
b) The compound shows excellent pharmacokinetics profiles such as high bioavailability or low clearance.
c) The compound has a high metabolic stability.
d) The compound does not show irreversible inhibitions to CYP enzymes such as CYP3A4 in the range of the concentrations of the measurement conditions described in this description.
e) The compound does not show a mutagenesis.
f) The compound is at a low risk for cardiovascular systems.
g) The compound shows a high solubility.
h) The compound shows a high brain distribution.
i) The compound has a high oral absorption.
j) The compound has a long half-life period.
k) The compound has a high protein unbinding ratio.
l) The compound is negative in the Ames test.
m) The compound has a high BACE1 selectivity over BACE2.
n) The compound has weak mechanism based inhibition against CYP enzymes. For example, the reactive metabolites of the compound have week inhibition against CYP enzymes.
o) The compound generates little reactive metabolites.
p) The compound is a weak P-gp substrate.

Since the compound of the present invention has high inhibitory activity on BACE1 and/or high selectivity on other enzymes, for example, BACE2, it can be a medicament with reduced side effect. Further, since the compound has high effect of reducing amyloid ß production in a cell system, particularly, has high effect of reducing amyloid ß production in brain, it can be an excellent medicament. In addition, by converting the compound into an optically active compound having suitable stereochemistry, the compound can be a medicament having a wider safety margin on the side effect.

When a pharmaceutical composition of the present invention is administered, it can be administered orally or parenterally. The composition for oral administration can be administered in usual dosage forms such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrated tablets. Powders and granules can be dry syrups. Capsules can be soft capsules, micro capsules or sustained-release capsules.

The composition for parenteral administration can be administered suitably in usual parenteral dosage forms such as dermal, subcutaneous, intravenous, intraarterial, intramuscular, intraperitoneal, transmucosal, inhalation, transnasal, ophthalmic, inner ear or vaginal administration and the like. In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The compounds of the present invention can be preferably administered in an oral dosage form because of their high oral absorbability.

A pharmaceutical composition can be formulated by mixing various additive agents for medicaments, if needed, such as excipients, binders, disintegrating agents, and lubricants which are suitable for the formulations with an effective amount of the compound of the present invention. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

The dosage of a pharmaceutical composition of the present invention should be determined in consideration of the patient's age and body weight, the type and degree of diseases, the administration route and the like. The usual oral dosage for adults is in the range of 0.05 to 100 mg/kg/day and preferable is 0.1 to 10 mg/kg/day. For parenteral administration, the dosage highly varies with administration routes and the usual dosage is in the range of 0.005 to 10 mg/kg/day and preferably 0.01 to 1 mg/kg/day. The dosage may be administered once or several times per day.

The compound of the present invention can be used in combination with other drugs for treating Alzheimer's disease, Alzheimer dementia or the like such as acetylcholinesterase inhibitor (hereinafter referred to as a concomitant medicament) for the purpose of enforcement of the activity of the compound or reduction of the amount of medication of the compound or the like. In this case, timing of administration of the compound of the present invention and the concomitant medicament is not limited and these may be administered to the subject simultaneously or at regular intervals. Furthermore, the compound of the present invention and concomitant medicament may be administered as two different compositions containing each active ingredient or as a single composition containing both active ingredient.

The dose of the concomitant medicament can be suitably selected on the basis of the dose used on clinical. Moreover, the mix ratio of the compound of the present invention and a concomitant medicament can be suitably selected in consideration of the subject of administration, administration route, target diseases, symptoms, combinations, etc. For example, when the subject of administration is human, the concomitant medicament can be used in the range of 0.01 to 100 parts by weight relative to 1 part by weight of the compounds of the present invention.

Examples of a concomitant medicament are Donepezil hydrochloride, Tacrine, Galanthamine, Rivastigmine, Zanapezil, Memantine and Vinpocetine.

EXAMPLE

Following examples and test examples illustrate the present invention in more detail, but the present invention is not limited by these examples.

In examples, the meaning of each abbreviation is as follows:
Ac: Acetyl
Et: ethyl
Bz: benzoyl
DCC: dicyclohexylcarbodiimide
DIC: diisopropylcarbodiimide
iPr: isopropyl
Me: methyl
Ph: phenyl
t-Bu: tert-butyl
TBS: tert-butyldimethylsilyl
AIBN: azobisisobutyronitrile
ADDP: 1,1'-(Azodicarbonyl)dipiperidine
AIBN: 2,2'-azobis(isobutyronitrile)
$(Boc)_2O$: di-tert-butyl Dicarbonate
BOMCl: benzyl chloromethyl etheroxymethyl chloride
DAST: N,N-diethylaminosulfur trifluoride
DBU: 1,8-Diazabicyclo[5.4.0]-7-undecene
DCM: dichloromethane
DEAD: diethyl azodicarboxylate
DIAD: diisopropyl azodicarboxylate
DIBAL: diisobutylaluminum Hydride
DIPEA: N,N-diisopropylethylamine
DMA: N,N-dimethylacetamide
DMAP: 4-dimethylaminopyridine
DMF: N,N-dimethylformamide
DMSO: dimethylsulfoxide
EDC: 1-ethyl-3-(3-dimethylaminopropyl)carbodiimide
HATU: O-(7-aza-1H-benzotriazol-1-yl)-N,N,N',N'-tetramethyluronium hexafluorophosphate
HOAt: 1-hydroxy-7-aza-benzotriazole
HOBt: 1-hydroxy-benzotriazole
LDA: lithium diisopropylamide
LHMDS: lithium bis(trimethylsilyl)amide
mCPBA: m-chloroperoxybenzoic acid
NCS: N-chlorosuccinimide
NMP: N-methylpyrrolidone
PPTS: pyridinium p-toluenesulfonate
PyBOP: 1H-Benzotriazol-1-yloxy-tri(pyrrolidino) phosphonium hexafluorophosphate
TEMPO: 2,2,6,6-tetramethylpiperidine 1-oxyl free radical
TFA: trifluoroacetic acid
THF: tetrahydrofuran
THP: 2-tetrahydropyranyl $^1$H NMR spectra were recorded on Bruker Advance 400 MHz spectrometer with chemical shift reported relative to tetramethylsilane or the residual solvent peak ($CDCl_3$=7.26 ppm, DMSO-$d_6$=2.50 ppm).

Analytical LC/MS (ESI positive or negative, retention time (RT)) data were recorded on Shimadzu UFLC or Waters UPLC system under the following conditions:
Method A
Column: XBridge (Registered trademark) C18 (5 μm, i.d.4.6×50 mm) (Waters)
Flow rate: 3 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 1 minute.
Method B
Column: Shim-pack XR-ODS (2.2 μm, i.d. 50×3.0 mm) (Shimadzu)
Flow rate: 1.6 mL/min
Column oven: 50° C.
UV detection wavelength: 254 nm
Mobile phase: [A] 0.1% formic acid-containing aqueous solution; [B] 0.1% formic acid-containing acetonitrile solution
Gradient: linear gradient from 10% to 100% solvent [B] for 3 minutes and 100% solvent [B] for 1 minute
Method C
Column: BEH C18 (1.7 μm, 2.1×50 mm) (Waters)
Flow rate: 0.8 mL/min
UV detection wavelength: 254 nm
Mobile phases: [A] is 10 mM $CH_3COONH_4$ in 95% $H_2O$+ 5% $CH_3CN$, and [B] is acetonitrile.
Gradient: linear gradient of 5% to 95% solvent [B] for 1.3 minutes was performed, and 95% solvent [B] was maintained for 0.7 minutes.
Method D
Column: HSS T3 (1.8 μm, 2.1×100 mm) (Waters)
Flow rate: 0.7 mL/min
UV detection wavelength: 254 nm
Mobile phases: [A] is 10 mM $CH_3COONH_4$ in 95% $H_2O$+ 5% $CH_3CN$, and [B] is acetonitrile.
Gradient: linear gradient of 0% to 95% solvent [B] for 2.1 minutes was performed, and 95% solvent [B] was maintained for 0.5 minutes.

Example 1

Synthesis of Compound I-007

[Chem. 28]

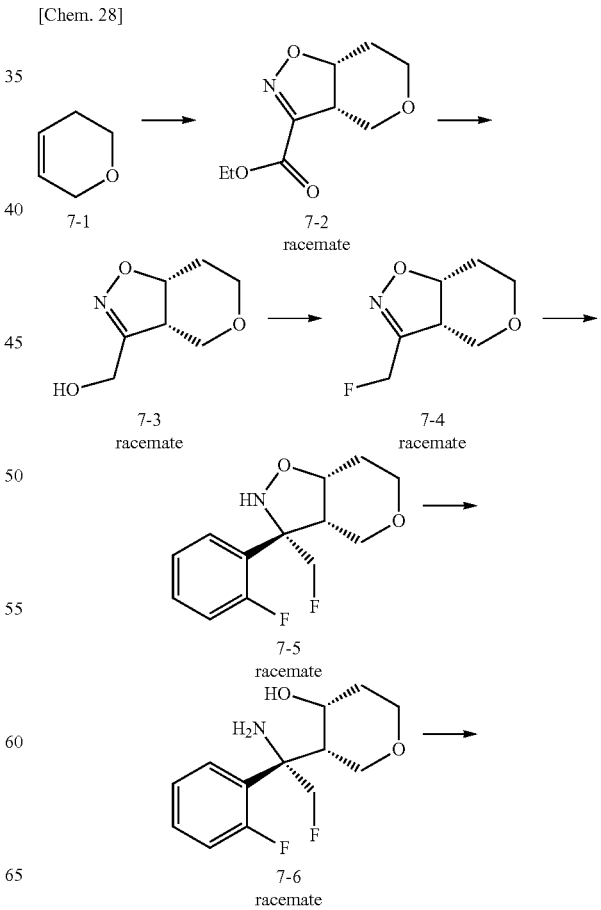

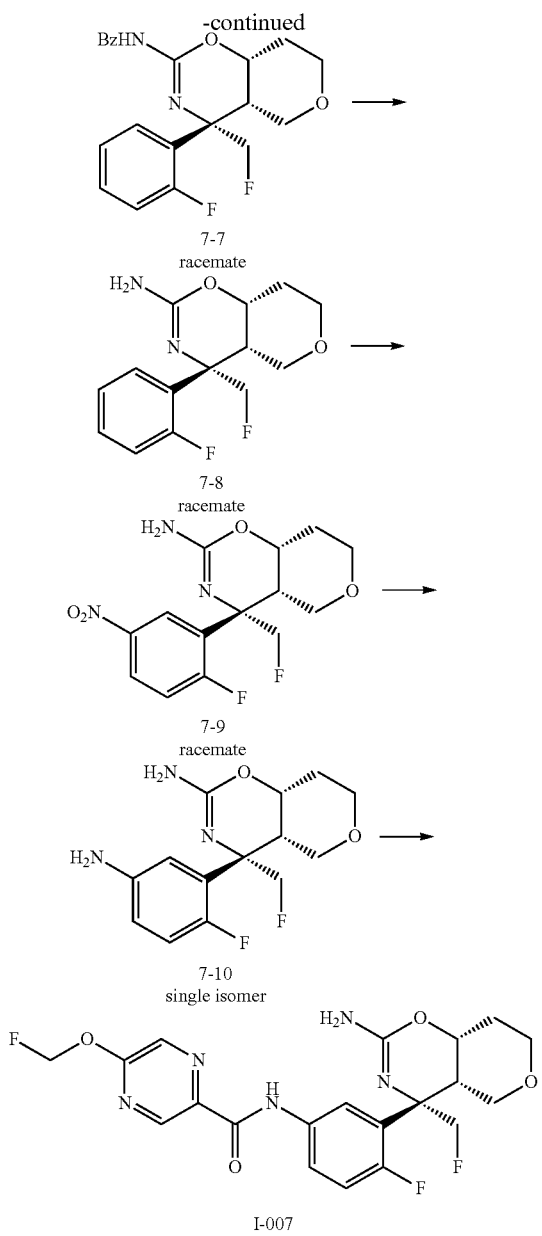

Step 1: Synthesis of Compound 7-2

To a solution of 3,6-dihydro-2H-pyran 7-1 (6.20 g, 73.7 mmol) and Et₃N (10.2 ml, 73.7 mmol) in toluene (60 ml) was added ethyl (2)-2-chloro 2-(hydroxyimino)acetate (22.3 g, 147 mmol) in toluene (120 ml) at 100° C. After stirring for 4 hours at reflux temperature, to the reaction mixture was added Et₃N (10.2 ml, 73.7 mmol). After stirring for 6 hours at reflux temperature, to the reaction mixture were added ethyl (Z)-2-chloro 2-(hydroxyimino)acetate (11.2 g, 73.7 mmol) and Et₃N (10.2 ml, 73.7 mmol). After stirring for 5 hours at reflux temperature, to the reaction mixture were added ethyl (2)-2-chloro 2-(hydroxyimino)acetate (5.58 g, 36.9 mmol) and Et₃N (5.1 ml, 36.9 mmol). After stirring for 1 hour at reflux temperature, the reaction mixture was cooled to room temperature. To the mixture was added H₂O, and the aqueous layer was extracted with EtOAc. The organic layer was washed with water, dried over Na₂SO₄ and filtered. The filtrate was concentrated in vacuo. The crude product was added to a silica gel column and eluted with hexane/EtOAc 0% to 40%. Collected fractions were evaporated to afford Compound 7-2 (5.10 g, 25.6 mmol, 35%) as an orange oil.

¹H NMR (CDCl₃) δ: 1.38 (3H, t, J=7.2 Hz), 2.07-2.12 (2H, m), 3.43 (1H, dd, J=14.6, 7.9 Hz), 3.55 (1H, dd, J=11.8, 7.9 Hz), 3.66 (1H, dt, J=15.7, 5.3 Hz), 3.77-3.82 (1H, m), 4.04 (1H, dd, J=11.9, 6.3 Hz), 4.32-4.38 (2H, m), 4.78-4.83 (1H, m).

Step 2: Synthesis of Compound 7-3

To a solution of NaBH₄ (3.26 g, 86.0 mmol) in EtOH (140 ml) was added a solution of Compound 7-2 (14.3 g, 71.9 mmol) in EtOH (140 mL) at 0° C. The reaction mixture was stirred for 3 hours at 40° C. and was treated with AcOH at 0° C. The reaction mixture was concentrated in vacuo. The crude product was added to a silica gel column and eluted with hexane/EtOAc 50% to 70%. Collected fractions were evaporated to afford Compound 7-3 (7.24 g, 46.1 mmol, 64%) as a colorless oil.

¹H NMR (CDCl₃) δ: 1.88-2.08 (2H, m), 3.25 (1H, q, J=6.9 Hz), 3.64-3.76 (3H, m), 3.94 (1H, dd, J=12.0, 6.0 Hz), 4.44-4.49 (2H, m), 4.67-4.70 (1H, m).

Step 3: Synthesis of Compound 7-4

To a solution of Compound 7-3 (7.24 g, 46.1 mmol) in CH₂Cl₂ (109 ml) was added 90% DAST (13.5 ml, 92.0 mmol) at −78° C. The reaction mixture was stirred for 2.5 hours at room temperature and was treated with aqueous potassium carbonate at 0° C. The mixture was extracted with CHCl₃ and dried over Na₂SO₄, filtered and concentrated. The crude product was added to a silica gel column and eluted with hexane/EtOAc 20% to 40%. Collected fractions were evaporated to afford Compound 7-4 (4.39 g, 27.6 mmol, 60%) as a yellow oil.

¹H NMR (CDCl₃) δ: 1.91-2.02 (1H, m), 2.02-2.12 (1H, m), 3.29-3.31 (1H, m), 3.62 (1H, dd, J=12.2, 7.0 Hz), 3.71 (2H, dd, J=7.0, 4.5 Hz), 3.95 (1H, dd, J=12.2, 6.0 Hz), 4.70-4.74 (1H, m), 5.12-5.23 (2H, m).

Step 4: Synthesis of Compound 7-5

To a solution of 1-bromo-2-fluorobenzene (4.39 g, 27.6 mmol) in toluene (176 mL) and THF (44 mL) was added n-BuLi (1.64 M in n-hexane, 50.5 mL, 83.0 mmol) at −78° C. and the reaction mixture was stirred for 5 minutes at the same temperature. To the reaction mixture were added BF₃·OEt₂ (4.2 ml, 33.1 mmol) and a solution of Compound 7-4 (4.39 g, 27.6 mmol) in toluene (97 mL) at −78° C. and the reaction mixture was stirred for 10 minutes at the same temperature. To the reaction mixture was added aqueous NH₄Cl solution, and the aqueous layer was extracted with EtOAc. The organic layer was washed with water and was concentrated in vacuo. The crude product was added to a silica gel column and eluted with hexane/EtOAc 10% to 20%. Collected fractions were evaporated to afford Compound 7-5 (4.91 g, 19.2 mmol, 70%) as a yellow oil.

¹H NMR (CDCl₃) δ: 1.91-1.85 (2H, m), 2.89-2.95 (1H, m), 3.60-3.66 (1H, m), 3.69-3.74 (1H, m), 3.76-3.82 (1H, m), 4.01-4.04 (1H, m), 4.08-4.13 (2H, m), 4.54 (1H, dd, J=47.9, 10.2 Hz), 5.04 (1H, dd, J=47.2, 10.2 Hz), 6.46 (1H, br s), 7.03-7.09 (1H, m), 7.19-7.22 (1H, m), 7.28-7.34 (1H, m), 7.92-7.96 (1H, m).

Step 5: Synthesis of Compound 7-6

To a solution of Compound 7-5 (4.91 g, 19.2 mmol) in AcOH (49 ml) was added Zn (12.6 g, 192 mmol) at room temperature. After stirring for 1 hour at 60° C., the reaction mixture was cooled to room temperature and was filtered through Celite (Registered trademark) pad. To the filtrate was added aqueous potassium carbonate solution. The mixture was filtered through Celite (Registered trademark) pad, and the filtrate was extracted with EtOAc. The organic layer was washed with water and concentrated in vacuo. The crude product was added to a silica gel column and eluted with Hexane/EtOAc 50%. Collected fractions were evaporated to afford Compound 7-6 (3.80 g, 14.8 mmol, 77%) as a colorless oil.

$^1$H NMR (CDCl$_3$) δ: 1.51-1.55 (1H, m), 1.61-1.69 (1H, m), 2.38-2.43 (1H, m), 3.57 (1H, br s), 3.67 (1H, dd, J=11.0, 5.1 Hz), 3.81-3.87 (1H, m), 3.94 (1H, t, J=11.2 Hz), 4.02-4.07 (1H, m), 4.45 (1H, dd, J=47.7, 9.3 Hz), 4.97 (1H, ddd, J=48.1, 9.3, 3.7 Hz), 7.08 (1H, dd, J=12.4, 8.2 Hz), 7.22-7.24 (1H, m), 7.33-7.37 (1H, m), 7.62-7.63 (1H, m).

Step 6: Synthesis of Compound 7-7

To a solution of Compound 7-6 (3.80 g, 14.8 mmol) in CH$_2$Cl$_2$ (38 ml) was added benzoyl isothiocyanate (2.18 ml, 16.2 mmol) at 0° C. After stirring for 19 hours at room temperature, to the reaction mixture was added EDC-HCl (5.66 g, 29.5 mmol) at the same temperature. After stirring for 3 hours at 40° C., the reaction mixture was concentrated in vacuo. The crude product was added to a silica gel column and eluted with Hexane/EtOAc 10% to 40%. Collected fractions were evaporated to afford Compound 7-7 (4.22 g, 10.9 mmol, 74%) as a white solid.

$^1$H NMR (CDCl$_3$) δ: 1.85-1.93 (1H, m), 2.04-2.08 (1H, m), 2.87-2.92 (1H, m), 3.74 (1H, t, J=11.7 Hz), 3.80-3.84 (2H, m), 4.04-4.09 (1H, m), 4.37 (1H, br s), 4.70-4.98 (2H, m), 7.13-7.25 (2H, m), 7.38-7.46 (4H, m), 7.51-7.54 (1H, m), 8.28 (2H, d, J=7.5 Hz), 12.14 (1H, s).

Step 7: Synthesis of Compound 7-8

To a solution of Compound 7-7 (4.22 g, 10.9 mmol) in MeOH (42 ml) was added DBU (1.81 ml, 12.0 mmol) at room temperature. After stirring for 7 hours at 60° C., to the reaction mixture were added 2 mol/L HCl and Et$_{2}$O. The organic layer was back-extracted with H$_2$O. The aqueous layer was alkalinized with K$_2$CO$_3$ (pH=8) and extracted with AcOEt. The organic layer was washed with water and concentrated in vacuo. The crude product was triturated with CHCl$_3$ to give Compound 7-8 (2.39 g, 8.47 mmol, 78%) as a yellow solid.

$^1$H NMR (CDCl$_3$) δ: 1.71-1.85 (2H, m), 2.69-2.74 (1H, m), 3.58-3.65 (2H, m), 3.75 (1H, dd, J=11.5, 5.0 Hz), 4.00-4.04 (2H, m), 4.25 (2H, s), 4.54-4.74 (2H, m), 7.04 (1H, dd, J=12.3, 8.2 Hz), 7.14-7.17 (1H, m), 7.27-7.31 (1H, m), 7.43-7.47 (1H, m).

Step 8: Synthesis of Compound 7-9

To a solution of Compound 7-8 (3.00 g, 10.6 mmol) in TFA (17.2 ml) was added sulfuric acid (4.25 ml, 80 mmol) at −15° C. After stirring for 10 minutes at the same temperature, to the reaction mixture was added HNO$_3$ (0.712 ml, 15.9 mmol). After stirring for 15 minutes at the same temperature, the reaction mixture was treated with aqueous K$_2$CO$_3$ solution. The aqueous layer was extracted with AcOEt. The organic layer was washed with brine, dried over Na$_2$SO$_4$ and filtered. The filtrate was concentrated under vacuum to give Compound 7-9 as a pale yellow solid that was used for the next step without purification.

Step 9: Synthesis of Compound 7-10

A solution of Compound 7-9 and 10% Pd—C (674 mg, 3.00 mmol) in MeOH (101 ml) was stirred under H$_2$ atmosphere at room temperature. After stirring for 2 hours at the same temperature, the mixture was filtered through Celite (Registered trademark) pad. The filtrate was concentrated under vacuum. The crude product was purified by supercritical fluid chromatography (SFC) (Chiralpak (Registered trademark) IC; 40% ethanol with 0.1% diethylamine) SFC to afford Compound 7-10 (1.35 g, 4.56 mmol, 44%) as a yellow solid.

$^1$H NMR (CDCl$_3$) δ: 1.71-1.85 (2H, m), 2.68-2.73 (1H, m), 3.55-3.64 (4H, m), 3.75 (1H, dd, J=11.5, 5.1 Hz), 3.98-4.03 (1H, m), 4.07 (1H, br s), 4.25 (2H, br s), 4.49-4.72 (2H, m), 6.53-6.56 (1H, m), 6.74 (1H, dd, J=6.7, 3.0 Hz), 6.83 (1H, dd, J=11.7, 8.6 Hz).

Step 10: Synthesis of Compound I-007

To a solution of Compound 7-10 (31.6 mg, 0.106 mmol) in MeOH (2 ml) were added 5-(fluoromethoxy)pyrazine-2-carboxylic acid (18.3 mg, 0.106 mmol) and 2 mol/L HCl (0.053 ml, 0.106 mmol) at 0° C. To the reaction mixture was added EDC-HCl (9.86 mg, 0.0370 mmol) at the same temperature. After stirring for 30 minutes at room temperature, the reaction mixture was treated with aqueous NaHCO$_3$ solution. The aqueous layer was extracted with AcOEt. The organic layer was washed with H$_2$O and brine, dried over Na$_2$SO$_4$ and filtered. The filtrate was concentrated in vacuo. The crude product was triturated with AcOEt/hexane to give Compound I-007 (32.1 mg, 0.071 mmol, 67%) as a yellow solid.

MS (method B): m/z=452 [M+H]$^+$ $^1$H NMR (CDCl$_3$) δ: 1.73-1.84 (2H, m), 2.74-2.78 (1H, m), 3.58-3.66 (2H, m), 3.75-3.79 (1H, m), 4.00-4.05 (1H, m), 4.09 (1H, br s), 4.32 (2H, br s), 4.63 (2H, d, J=46.9 Hz), 6.15 (2H, dd, J=51.1, 7.5 Hz), 7.10 (1H, dd, J=11.4, 9.0 Hz), 7.49 (1H, dd, J=6.9, 2.6 Hz), 7.98-8.03 (1H, m), 8.29 (1H, s), 9.08 (1H, s), 9.50 (1H, s).

Example 2

Synthesis of Compound I-008

[Chem. 29]

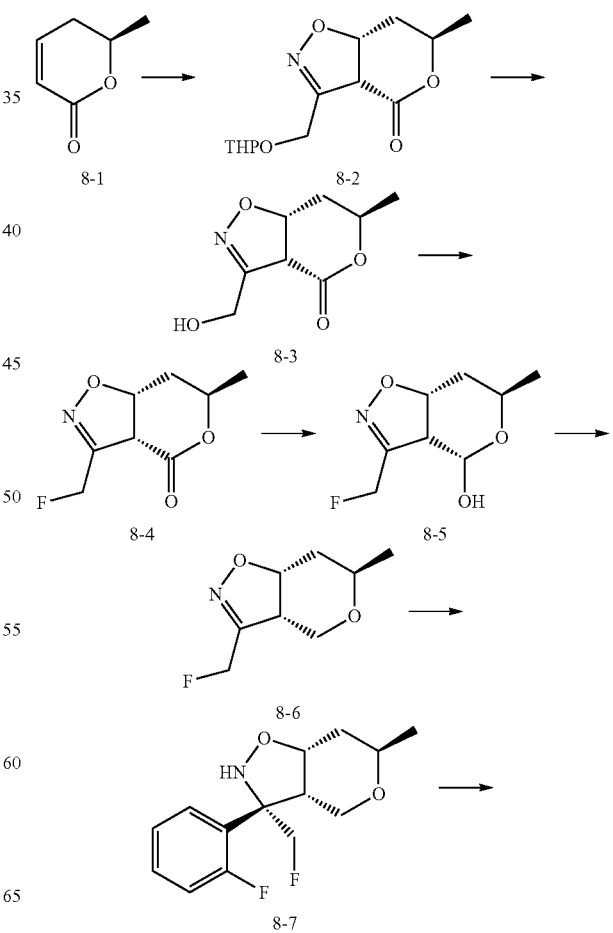

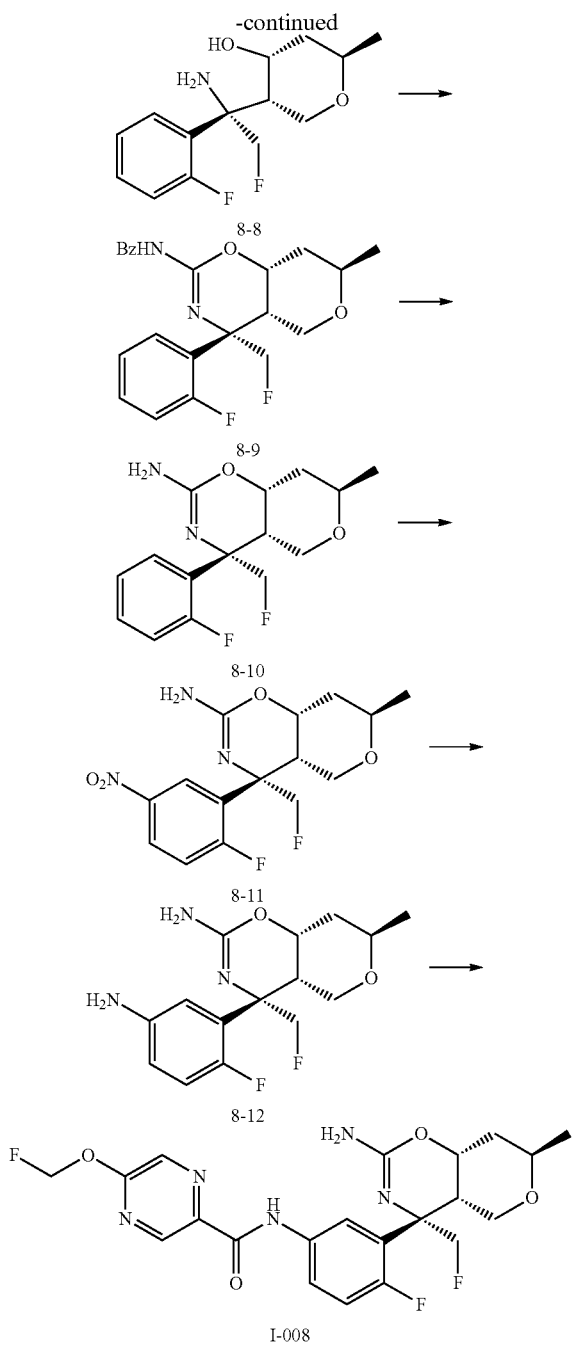

fractions were evaporated to afford Compound 8-2 (8.05 g, 29.9 mmol, 82%) as an orange oil.

$^1$H NMR (CDCl$_3$) δ: 1.41 (3H, dd, J=6.3, 1.5 Hz), 1.60-1.74 (5H, m), 1.78-1.86 (2H, m), 2.17-2.21 (1H, m), 3.53-3.57 (1H, m), 3.82-3.94 (1H, m), 4.25 (1H, dd, J=12.5, 6.9 Hz), 4.37-4.41 (1H, m), 4.50-4.59 (2H, m), 4.70-4.76 (1H, m), 5.07-5.11 (1H, m).

Step 2: Synthesis of Compound 8-3

To a solution of Compound 8-2 (8.05 g, 29.9 mmol) in EtOH (81 ml) was added PPTS (1.50 g, 5.98 mmol) at room temperature. After stirring for 2 hours at 60° C., the reaction mixture was concentrated in vacuo. The crude product was added to a silica gel column and eluted with hexane/EtOAc 10% to 80%. Collected fractions were evaporated to afford Compound 8-3 (4.46 g, 29.9 mmol, 81%) as a brown oil.

$^1$H NMR (CDCl$_3$) δ: 1.44 (3H, d, J=6.3 Hz), 1.83-1.91 (1H, m), 2.21-2.25 (1H, m), 2.47-2.50 (1H, m), 4.41 (1H, d, J=10.9 Hz), 4.51 (2H, dd, J=13.9, 6.7 Hz), 4.55-4.63 (1H, m), 5.06-5.10 (1H, m).

Step 3: Synthesis of Compound 8-4

To a solution of Compound 8-3 (4.93 g, 26.6 mmol) in CH$_2$Cl$_2$ (49 ml) was added 90% DAST (5.86 ml, 39.9 mmol) at −78° C. The reaction mixture was stirred for 2 hours at room temperature and was treated with aqueous potassium carbonate solution. The mixture was extracted with CH$_2$Cl$_2$. The organic layer was dried over Na$_2$SO$_4$ and concentrated in vacuo. The crude product was added to a silica gel column and eluted with hexane/EtOAc 10% to 30%. Collected fractions were evaporated to afford Compound 8-4 (4.50 g, 24.1 mmol, 90%) as a yellow oil.

$^1$H NMR (CDCl$_3$) δ: 1.43 (3H, d, J=6.4 Hz), 1.85-1.92 (1H, m), 2.25 (1H, d, J=15.3 Hz), 4.39 (1H, dd, J=11.0, 3.0 Hz), 4.54-4.58 (1H, m), 5.16-5.27 (3H, m).

Step 4: Synthesis of Compound 8-5

To a solution of Compound 8-4 (4.50 g, 24.1 mmol) in CH$_2$Cl$_2$ (45 ml) was added DIBAL (1.03 mol/L in hexane, 24.5 ml, 10.9 mmol) at −78° C. After stirring for 20 minutes at the same temperature, to the reaction mixture was added Rochelle's salt. After stirring for 3 hours at room temperature, to the mixture was added 2 mol/L HCl (pH=4). To the mixture was added NaCl, which was then extracted with CH$_2$Cl$_2$ and AcOEt. The combined organic layers were dried over Na$_2$SO$_4$ and filtered. The filtrate was concentrated under vacuum. The crude product was added to a silica gel column and eluted with hexane/EtOAc 30% to 50%. Collected fractions were evaporated to afford Compound 8-5 (2.65 g, 14.0 mmol, 58%) as a white solid as diastereomer mixture.

$^1$H NMR (CDCl$_3$) δ: 1.30 (3H, d, J=6.3 Hz), 1.76-1.84 (1H, m), 2.11-2.15 (1H, m), 3.06 (1H, t, J=7.7 Hz), 3.14 (1H, d, J=4.5 Hz), 3.83-3.91 (1H, m), 4.71-4.74 (1H, m), 4.77 (1H, dd, J=7.1, 4.7 Hz), 5.16-5.26 (2H, m).

Step 5: Synthesis of Compound 8-6

To a solution of Compound 8-5 (2.55 g, 13.5 mmol) and triethylsilane (10.8 ml, 67.5 mmol) in DCM (41 ml) and MeCN (41 ml) was added BF$_3$-OEt$_2$ (8.56 ml, 67.5 mmol) at 0° C. After stirring for 40 minutes at the same temperature, the reaction mixture was treated with aqueous sodium carbonate solution. The aqueous layer was extracted with CH$_2$Cl$_2$, and the organic layer was dried over Na$_2$SO$_4$ and filtered. The filtrate was concentrated under vacuum to give Compound 8-6 as a yellow oil that was used for the next step without purification.

Step 6: Synthesis of Compound 8-7

To a solution of 1-bromo-2-fluorobenzene (6.11 g, 34.9 mmol) in toluene (128 mL) and THF (16 mL) was added n-BuLi (1.64 M in n-hexane, 21.3 mL, 34.9 mmol) at −78°

Step 1: Synthesis of Compound 8-2

To a solution of Compound 8-1 (4.10 g, 36.6 mmol), which was prepared according to a known procedure, and phenyl isocyanate (12.0 ml, 110 mmol) in toluene (80 ml) were added 2-(2-nitroethoxy)tetrahydro-2H-pyran (9.62 g, 54.9 mmol) and DIPEA (0.320 ml, 1.83 mmol) in toluene (30 ml) at 110° C. After stirring for 2 hours at reflux temperature, to the reaction mixture were added DIPEA (0.639 ml, 3.66 mmol) and phenyl isocyanate (12.0 ml, 110 mmol). After stirring for 4 hours at reflux temperature, the reaction mixture was cooled to room temperature. The mixture was filtered, and the filtrate was concentrated in vacuo. The crude product was added to a silica gel column and eluted with hexane/EtOAc 10% to 30%. Collected C., and the reaction mixture was stirred for 5 minutes at the same temperature. To the reaction mixture was added $BF_3$-$OEt_2$ (1.77 ml, 14.0 mmol). After stirring for 10 minutes at the same temperature, to the mixture was added a solution of crude Compound 8-6 in THF (16 mL) and toluene (32 ml) at −78° C., and the reaction mixture was stirred for 15 minutes at the same temperature. To the reaction mixture was added aqueous $NH_4Cl$ solution, and the aqueous layer was extracted with EtOAc. The organic layer was washed with water and concentrated in vacuo. The crude product was added to a silica gel column and eluted with hexane/EtOAc 0% to 20%. Collected fractions were evaporated to afford Compound 8-7 (3.19 g, 11.8 mmol, 85%) as a yellow oil.

$^1$H NMR ($CDCl_3$) δ: 1.18 (3H, d, J=6.1 Hz), 1.45-1.54 (1H, m), 1.91-1.94 (1H, m), 2.89-2.95 (1H, m), 3.58-3.66 (1H, m), 3.68-3.76 (1H, m), 3.92-3.93 (1H, m), 4.15-4.21 (1H, m), 4.49 (1H, dd, J=48.2, 10.4 Hz), 5.03 (1H, dd, J=46.9, 10.4 Hz), 6.50 (1H, br s), 7.04-7.10 (1H, m), 7.19-7.23 (1H, m), 7.29-7.34 (1H, m), 7.90-7.94 (1H, m).

Step 7: Synthesis of Compound 8-8

To a solution of Compound 8-7 (3.19 g, 11.9 mmol) in AcOH (31.9 ml) was added Zn (7.74 g, 118 mmol) at room temperature. After stirring for 2 hours at 60° C., the reaction mixture was cooled to room temperature and was filtered through Celite (Registered trademark) pad. The filtrate was treated with aqueous potassium carbonate solution, and the mixture was extracted with EtOAc. The organic layer was washed with water and concentrated in vacuo to afford Compound 8-8 (3.07 g), which was used for the next reaction without further purification.

Step 8: Synthesis of Compound 8-9

To a solution of crude Compound 8-8 (11.3 g) in $CH_2Cl_2$ (30.7 ml) was added benzoyl isothiocyanate (1.67 ml, 12.5 mmol) at 0° C. After stirring for 14 hours at room temperature, to the reaction mixture was added EDC-HCl (4.34 g, 22.7 mmol). After stirring for 5 h at 40° C., the reaction mixture was concentrated in vacuo. The crude product was added to a silica gel column and eluted with $CHCl_3$/AcOEt 20%. Collected fractions were evaporated to afford Compound 8-9 (3.73 g, 9.32 mmol, 82%) as a yellow solid.

$^1$H NMR ($CDCl_3$) δ: 1.20 (3H, d, J=6.3 Hz), 1.50 (1H, td, J=10.0, 4.8 Hz), 2.10-2.14 (1H, m), 2.83-2.86 (1H, m), 3.80 (1H, t, J=11.7 Hz), 3.86-3.94 (1H, m), 4.07 (1H, dd, J=12.7, 6.1 Hz), 4.36 (1H, br s), 4.70-4.82 (1H, m), 4.92 (1H, dd, J=46.2, 9.5 Hz), 7.16 (1H, dd, J=12.3, 8.3 Hz), 7.20-7.24 (1H, m), 7.38-7.46 (4H, m), 7.50-7.54 (1H, m), 8.27-8.29 (2H, m), 12.13 (1H, br s).

Step 9: Synthesis of Compound 8-10

To a solution of Compound 8-9 (3.73 g, 9.32 mmol) in MeOH (37 ml) and THF (37 ml) was added hydrazine hydrate (4.53 ml, 93.0 mmol) at room temperature. After stirring for 14 hours at the same temperature, the reaction mixture was concentrated. The resulting residue was added to an amino silica gel column and eluted with Hexane/EtOAc 40%. Collected fractions were evaporated to afford Compound 8-10 (2.30 g, 7.77 mmol, 83%) as a white solid.

$^1$H NMR ($CDCl_3$) δ: 1.16 (3H, d, J=6.3 Hz), 1.37-1.44 (1H, m), 1.82-1.77 (1H, m), 2.64-2.68 (1H, m), 3.65-3.73 (2H, m), 4.00-4.04 (2H, m), 4.25 (2H, br s), 4.59-4.71 (2H, m), 7.04 (1H, dd, J=12.3, 8.0 Hz), 7.14-7.17 (1H, m), 7.29-7.31 (1H, m), 7.43-7.47 (1H, m).

Step 10: Synthesis of Compound 8-11

To a solution of Compound 8-10 (2.30 g, 7.76 mmol) in TFA (12.6 ml) was added sulfuric acid (3.10 ml, 58.2 mmol) at −17° C. After stirring for 10 minutes at the same temperature, to the reaction mixture was added $HNO_3$ (0.520 ml, 11.6 mmol). After stirring for 20 minutes at the same temperature, the reaction mixture was treated with aqueous $K_2CO$ solution, and the aqueous layer was extracted with EtOAc. The organic layer was washed with water and concentrated in vacuo to afford Compound 8-11 (2.83 g), which was used for the next reaction without further purification.

Step 11: Synthesis of Compound 8-12

A solution of crude Compound 8-11 (2.83 g, 7.76 mmol) and 10% Pd—C (566 mg) in MeOH (85 ml) was stirred under $H_2$ atmosphere at room temperature. After stirring for 2 hours at the same temperature, the mixture was filtered through Celite (Registered trademark) pad. The filtrate was concentrated under vacuum. The residue was triturated with AcOEt, then the resulting solid was collected, washed with AcOEt and dried under reduced pressure to afford Compound 8-12 (1.50 g, 4.83 mmol, 62%) as a white solid. The filtrate was concentrated, and then the residue was purified by column chromatography (silica-gel AcOEt/MeOH=10/1) to afford Compound 8-12 (374 mg, 1.20 mmol, 16%) as a white solid.

$^1$H NMR ($CDCl_3$) δ: 1.16 (3H, d, J=6.3 Hz), 1.38-1.45 (1H, m), 1.78-1.83 (1H, m), 2.62-2.67 (1H, m), 3.58 (2H, br s), 3.62-3.73 (2H, m), 3.99-4.03 (1H, m), 4.07 (1H, br s), 4.23 (2H, br s), 4.51-4.71 (2H, m), 6.52-6.56 (1H, m), 6.74 (1H, dd, J=6.7, 2.9 Hz), 6.83 (1H, dd, J=11.8, 8.5 Hz).

Step 12: Synthesis of Compound I-008

To a solution of Compound 8-12 (50.1 mg, 0.161 mmol) in MeOH (3.0 ml) were added 5-(fluoromethoxy)pyrazine-2-carboxylic acid (27.7 mg, 0.161 mmol) and 2 mol/L HCl (0.080 ml, 0.177 mmol) at 0° C. To the reaction mixture was added EDC-HCl (33.9 mg, 0.177 mmol) at the same temperature. After stirring for 30 minutes at room temperature, the reaction mixture was treated with aqueous $NaHCO_3$ solution. The aqueous layer was extracted with AcOEt. The organic layer was washed with $H_2O$ and brine, dried over $Na_2SO_4$ and concentrated in vacuo. The resulting residue was added to an amino silica gel column and eluted with Hexane/EtOAc 50% to 100%. Collected fractions were evaporated. The residue was triturated with AcOEt/Hexane to give Compound 8-13 (45.5 mg, 0.098 mmol, 61%) as a white solid.

MS (method B): m/z=466 [M+H]$^+$ $^1$H NMR ($CDCl_3$) δ: 1.17 (3H, d, J=6.0 Hz), 1.40-1.47 (1H, m), 1.80-1.84 (1H, m), 2.68-2.73 (1H, m), 3.65-3.74 (2H, m), 4.01-4.08 (2H, m), 4.32 (2H, br s), 4.64 (2H, d, J=47.2 Hz), 6.07-6.23 (2H, m), 7.10 (1H, dd, J=11.4, 8.7 Hz), 7.48 (1H, dd, J=6.8, 2.8 Hz), 7.98-8.02 (1H, m), 8.29 (1H, d, J=1.3 Hz), 9.08 (1H, d, J=1.3 Hz), 9.51 (1H, br s).

Example 3

Synthesis of Compound I-009

[Chem. 30]

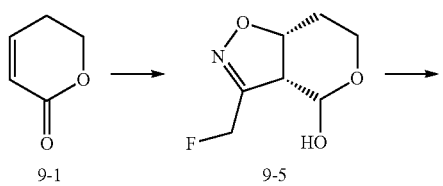

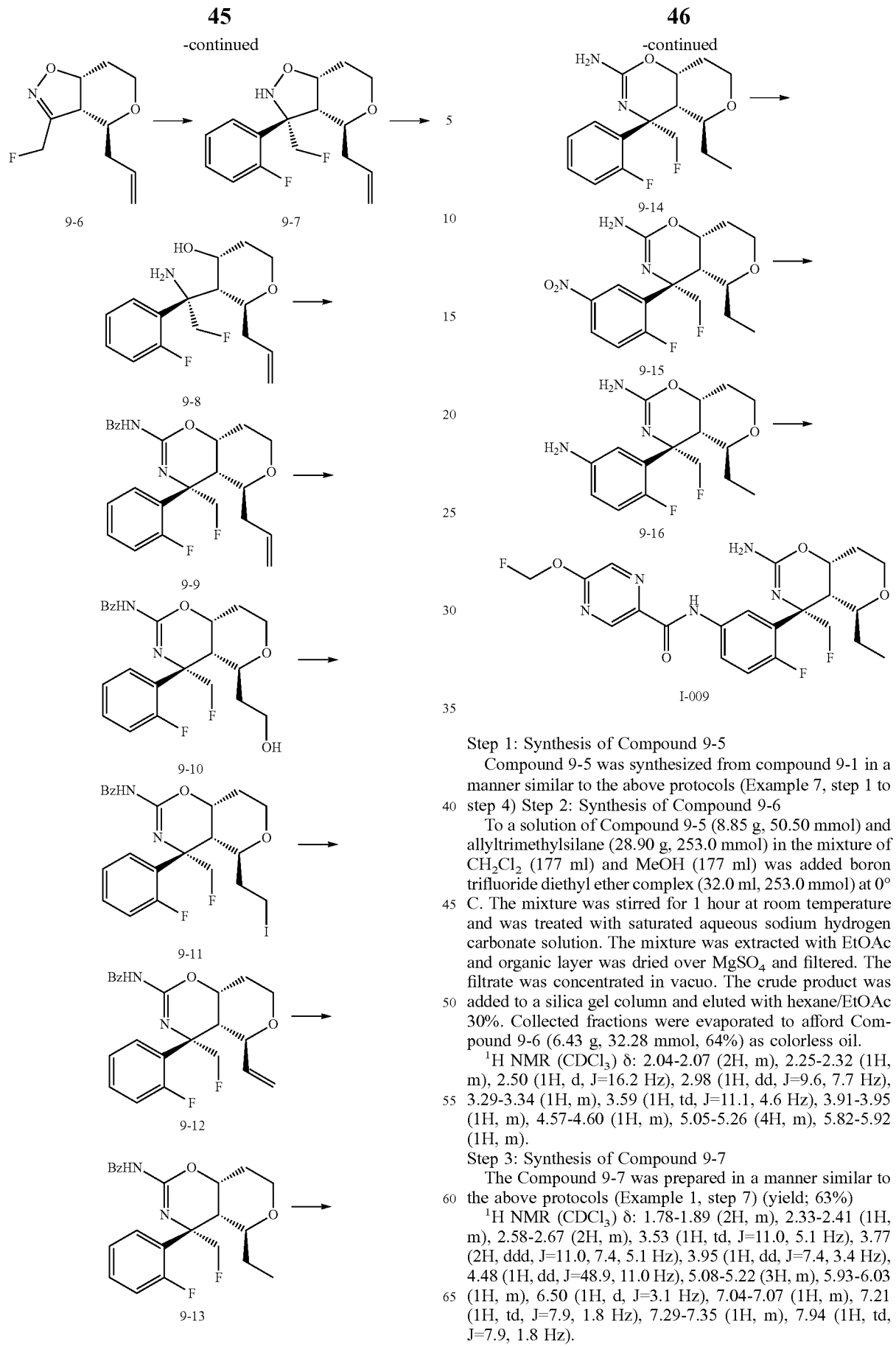

Step 1: Synthesis of Compound 9-5

Compound 9-5 was synthesized from compound 9-1 in a manner similar to the above protocols (Example 7, step 1 to step 4) Step 2: Synthesis of Compound 9-6

To a solution of Compound 9-5 (8.85 g, 50.50 mmol) and allyltrimethylsilane (28.90 g, 253.0 mmol) in the mixture of $CH_2Cl_2$ (177 ml) and MeOH (177 ml) was added boron trifluoride diethyl ether complex (32.0 ml, 253.0 mmol) at 0° C. The mixture was stirred for 1 hour at room temperature and was treated with saturated aqueous sodium hydrogen carbonate solution. The mixture was extracted with EtOAc and organic layer was dried over $MgSO_4$ and filtered. The filtrate was concentrated in vacuo. The crude product was added to a silica gel column and eluted with hexane/EtOAc 30%. Collected fractions were evaporated to afford Compound 9-6 (6.43 g, 32.28 mmol, 64%) as colorless oil.

$^1$H NMR (CDCl$_3$) δ: 2.04-2.07 (2H, m), 2.25-2.32 (1H, m), 2.50 (1H, d, J=16.2 Hz), 2.98 (1H, dd, J=9.6, 7.7 Hz), 3.29-3.34 (1H, m), 3.59 (1H, td, J=11.1, 4.6 Hz), 3.91-3.95 (1H, m), 4.57-4.60 (1H, m), 5.05-5.26 (4H, m), 5.82-5.92 (1H, m).

Step 3: Synthesis of Compound 9-7

The Compound 9-7 was prepared in a manner similar to the above protocols (Example 1, step 7) (yield; 63%)

$^1$H NMR (CDCl$_3$) δ: 1.78-1.89 (2H, m), 2.33-2.41 (1H, m), 2.58-2.67 (2H, m), 3.53 (1H, td, J=11.0, 5.1 Hz), 3.77 (2H, ddd, J=11.0, 7.4, 5.1 Hz), 3.95 (1H, dd, J=7.4, 3.4 Hz), 4.48 (1H, dd, J=48.9, 11.0 Hz), 5.08-5.22 (3H, m), 5.93-6.03 (1H, m), 6.50 (1H, d, J=3.1 Hz), 7.04-7.07 (1H, m), 7.21 (1H, td, J=7.9, 1.8 Hz), 7.29-7.35 (1H, m), 7.94 (1H, td, J=7.9, 1.8 Hz).

Step 4: Synthesis of Compound 9-8

The Compound 9-8 was prepared in a manner similar to the above protocols (Example 1, step 8) (yield; crude)

MS (method B): m/z=298 [M+H]$^+$.

Step 5: Synthesis of Compound 9-9

The Compound 9-9 was prepared in a manner similar to the above protocols (Example 1, step 9) (yield; 70%)

$^1$H NMR (CDCl$_3$) δ: 1.76-1.84 (1H, m), 2.01-2.06 (1H, m), 2.38-2.45 (1H, m), 2.59 (2H, dt, J=13.6, 5.5 Hz), 3.84 (3H, tt, J=13.6, 5.5 Hz), 4.41 (1H, d, J=2.8 Hz), 4.90-5.00 (2H, m), 5.17-5.20 (2H, m), 5.92-6.03 (1H, m), 7.12-7.24 (2H, m), 7.38-7.46 (4H, m), 7.53-7.58 (1H, m), 8.28 (2H, t, J=4.1 Hz), 12.10 (1H, s).

Step 6: Synthesis of Compound 9-10

O$_3$ was bubbled into a solution of Compound 9-9 (6.40 g, 15.01 mmol) in CH$_2$Cl$_2$ (224 ml) at −78° C. After 1.5 hours, N$_2$ was bubbled into this solution for 1.5 hours while the reaction temperature was gradually raised to room temperature. PPh$_3$ (9.05 g, 34.50 mmol) was added, and the resulting mixture was stirred at room temperature. After 1 hour, MeOH (64 ml) and NaBH$_4$ (1.70 g, 45.0 mmol) were added at 0° C. After being stirred at room temperature for 1 hour, the reaction mixture was quenched by saturated aqueous NH$_4$Cl solution. The mixture was extracted with EtOAc, and organic layer was dried over MgSO$_4$ and filtered. The filtrate was concentrated in vacuo. The crude product was added to a silica gel column and eluted with hexane/EtOAc 70%. Collected fractions were evaporated to afford Compound 9-10 (4.84 g, 11.24 mmol, 75%) as a white solid.

$^1$H NMR (CDCl$_3$) δ: 1.78-1.97 (2H, m), 2.08 (1H, t, J=1.8 Hz), 2.41-2.44 (1H, m), 2.59 (1H, dd, J=10.3, 2.4 Hz), 3.84-3.89 (5H, m), 4.04 (1H, t, J=10.3 Hz), 4.41 (1H, d, J=2.4 Hz), 4.91 (2H, d, J=46.7 Hz), 7.17 (1H, dd, J=12.4, 8.0 Hz), 7.21-7.25 (1H, m), 7.38-7.54 (5H, m), 8.28 (2H, t, J=4.3 Hz), 12.09 (1H, s).

Step 7: Synthesis of Compound 9-11

To a solution of Compound 9-10 (4.41 g, 10.25 mmol) in THF (88 ml) were added PPh$_3$ (5.37 g, 20.49 mmol), imidazole (1.40 g, 20.49 mmol) and iodine (5.20 g, 20.49 mmol) at 0° C. The mixture was stirred for 1 hour at the same temperature and was treated with 2% aqueous NaHSO$_3$ solution. The mixture was extracted with EtOAc, and the organic layer was dried over MgSO$_4$ and filtered. The filtrate was concentrated in vacuo. The crude product was added to a silica gel column and eluted with CHCl$_3$/EtOAc 20%. Collected fractions were evaporated to afford Compound 9-11 (5.22 g, 9.66 mmol, 94%) as white solid.

$^1$H NMR (CDCl$_3$) δ: 1.75-1.87 (1H, m), 2.07-2.16 (2H, m), 2.23-2.31 (1H, m), 2.52 (1H, d, J=8.0 Hz), 3.35-3.39 (2H, m), 3.78-3.84 (3H, m), 4.40 (1H, d, J=2.8 Hz), 4.90 (2H, d, J=46.7 Hz), 7.16 (1H, dd, J=12.5, 8.0 Hz), 7.23 (1H, t, J=8.0 Hz), 7.42-7.51 (5H, m), 8.29 (2H, d, J=7.3 Hz), 12.13 (1H, s).

Step 8: Synthesis of Compound 9-12

The Compound 9-12 was prepared in a manner similar to the above protocols (Example 1, step 11) (yield; 98%)

$^1$H NMR (CDCl$_3$) δ: 1.84-1.88 (1H, m), 2.05-2.07 (1H, m), 2.70 (1H, dd, J=10.3, 1.8 Hz), 3.85-3.97 (2H, m), 4.13-4.18 (1H, m), 4.43 (1H, d, J=2.8 Hz), 4.70-4.97 (2H, m), 5.54 (2H, dd, J=38.6, 13.7 Hz), 6.00-6.09 (1H, m), 7.16-7.21 (2H, m), 7.38-7.47 (4H, m), 7.53 (1H, tt, J=7.3, 1.7 Hz), 8.29-8.30 (2H, m), 12.13 (1H, s).

Step 9: Synthesis of Compound 9-13

The Compound 9-13 was prepared in a manner similar to the above protocols (Example 2, step 1). The yield was not determined because the product was used in the next step without purification.

MS (method B): m/z=415 [M+H]$^+$.

Step 10: Synthesis of Compound 9-14

The Compound 9-14 was prepared in a manner similar to the above protocols (Example 1, step 15). The yield was not determined because the product was used in the next step without purification.

MS (method B): m/z=311 [M+H]$^+$.

Step 11: Synthesis of Compound 9-15

The Compound 9-15 was prepared in a manner similar to the above protocols (Example 1, step 16). The yield was not determined because the product was used in the next step without purification.

MS (method B): m/z=356 [M+H]$^+$.

Step 12: Synthesis of Compound 9-16

The Compound 16 was prepared in a manner similar to the above protocols (Example 1, step 17). The crude was purified by supercritical fluid chromatography (SFC) (Chiralpak (Registered trademark) IC; 40% ethanol with 0.1% diethylamine) to afford Compound 9-16. (yield: 36%, 4 steps)

MS (method B): m/z=326 [M+H]$^+$.

Step 13: Synthesis of Compound I-009

The Compound I-009 was prepared in a manner similar to the above protocols (Example 1, step 18). (yield: 77%)

$^1$H NMR (CDCl$_3$) δ: 1.06 (3H, t, J=7.2 Hz), 1.56-1.89 (4H, m), 2.41 (1H, d, J=10.2 Hz), 3.61-3.71 (3H, m), 4.12 (1H, s), 4.39 (2H, br s), 4.66-4.78 (2H, m), 6.15 (2H, dd, J=51.1, 9.3 Hz), 7.09 (1H, dd, J=10.9, 9.3 Hz), 7.46 (1H, dd, J=6.8, 2.3 Hz), 7.99-8.00 (1H, m), 8.27 (1H, s), 9.06 (1H, s), 9.50 (1H, s).

Example 4

Synthesis of Compound I-010

[Chem. 31]

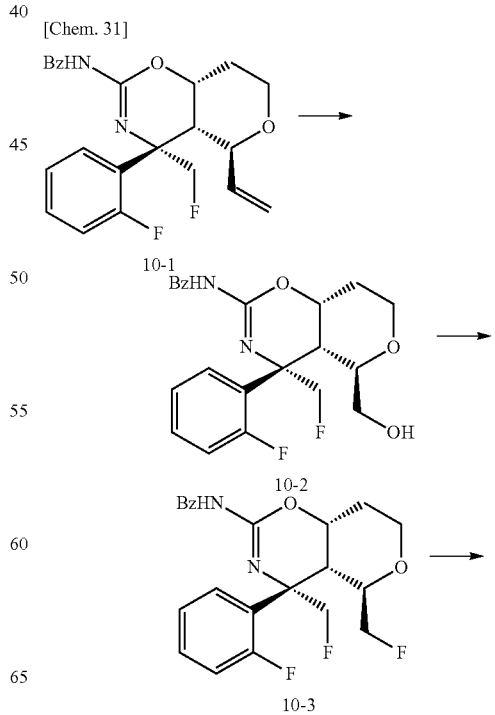

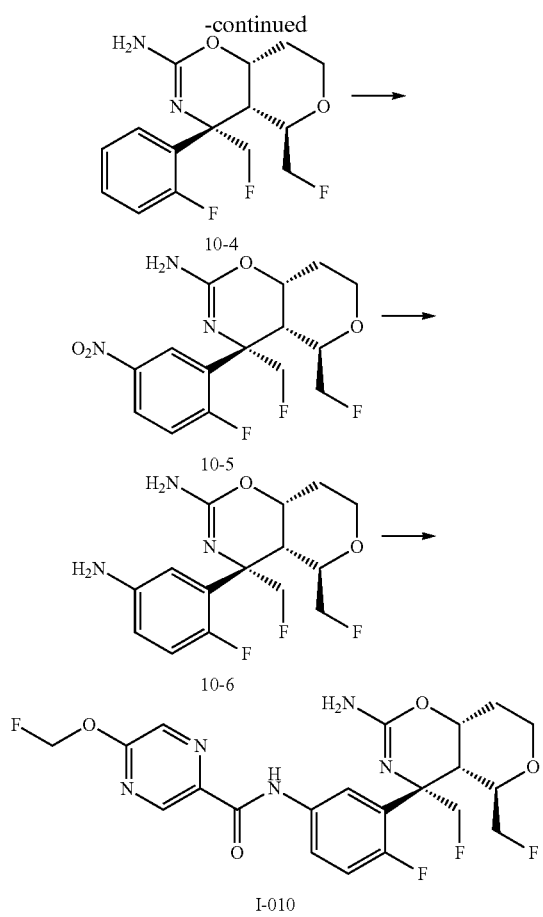

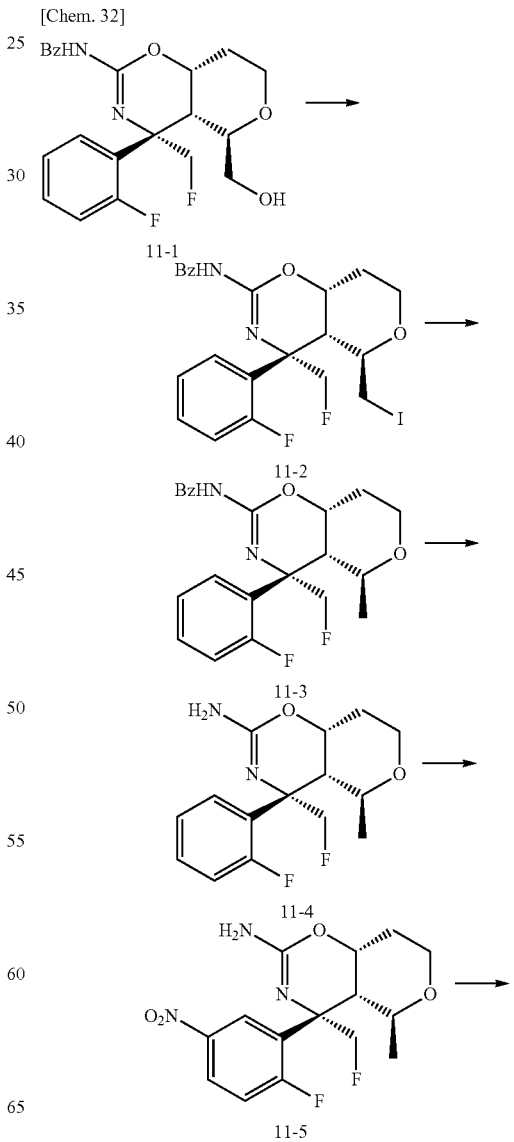

Step 5: Synthesis of Compound 10-6

The Compound 10-6 was prepared in a manner similar to the above protocols (Example 1, step 17). The crude was purified by supercritical fluid chromatography (SFC) (Chiralpak (Registered trademark) IC; 40% isopropanol with 0.1% diethylamine) to afford Compound 10-6 (yield: 50%)

MS (method B): m/z=330 [M+H]$^+$.

Step 6: Synthesis of Compound I-010 The compound 10-7 was prepared in a manner similar to the above protocols (Example 1, step 18). (yield; 71%)

$^1$H NMR (CDCl$_3$) δ: 1.73-1.84 (2H, m), 2.75-2.77 (1H, m), 3.75-3.87 (3H, m), 4.19 (1H, d, J=2.5 Hz), 4.41 (2H, s), 4.54-4.92 (4H, m), 6.15 (2H, dd, J=51.1, 8.3 Hz), 7.10 (1H, dd, J=11.3, 8.8 Hz), 7.54 (1H, dd, J=6.8, 2.8 Hz), 7.95 (1H, dt, J=8.8, 2.8 Hz), 8.28 (1H, d, J=1.3 Hz), 9.07 (1H, d, J=1.3 Hz), 9.50 (1H, s).

Example 5

Synthesis of Compound I-011

[Chem. 32]

Step 1: Synthesis of Compound 10-2

The Compound 10-2 was prepared in a manner similar to the above protocols (Example 7 step 5). (yield: 77%)

$^1$H NMR (CDCl$_3$) δ:1.79-1.84 (1H, m), 2.05-2.08 (1H, m), 2.23-2.25 (1H, m), 2.87 (1H, dd, J=10.3, 2.5 Hz), 3.75-3.99 (5H, m), 4.45 (1H, d, J=2.5 Hz), 4.93 (2H, dd, J=46.7, 2.5 Hz), 7.16 (1H, dd, J=12.3, 8.0 Hz), 7.23 (1H, t, J=8.0 Hz), 7.38-7.55 (4H, m), 7.67 (1H, dt, J=12.3, 4.3 Hz), 8.27 (2H, t, J=4.3 Hz), 12.10 (1H, s).

Step 2: Synthesis of Compound 10-3

The Compound 10-3 was prepared in a manner similar to the above protocols (Example 3, step 1). (yield: 32%)

$^1$H NMR (CDCl$_3$) δ: 1.85-1.88 (1H, m), 2.04-2.06 (1H, m), 2.97 (1H, dd, J=10.4, 1.9 Hz), 3.90-3.97 (3H, m), 4.48 (1H, s), 4.78-4.98 (4H, m), 7.17 (1H, dd, J=11.9, 8.2 Hz), 7.22-7.24 (1H, m), 7.41-7.45 (4H, m), 7.53 (1H, t, J=7.3 Hz), 8.27 (2H, d, J=7.3 Hz), 12.10 (1H, s).

Step 3: Synthesis of Compound 10-4

The Compound 10-4 was prepared in a manner similar to the above protocols (Example 1, step 15). The yield was not determined because the product was used in the next step without purification.

MS (method B): m/z=315 [M+H]$^+$.

Step 4: Synthesis of Compound 10-5

The Compound 10-5 was prepared in a manner similar to the above protocols (Example 1, step 16). The yield was not determined because the product was used in the next step without purification.

MS (method B): m/z=360 [M+H]$^+$.

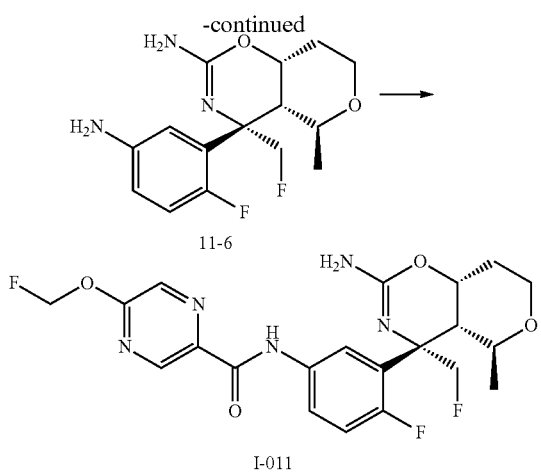

Step 1: Synthesis of Compound 11-2

The Compound 11-2 was prepared in a manner similar to the above protocols (Example 1, step 13). (yield: 88%)

MS (method B): m/z=527 [M+H]$^+$.

Step 2: Synthesis of Compound 11-3 The compound 11-3 was prepared in a manner similar to the above protocols (Example 1, step 14). (yield: 75%)

$^1$H NMR (CDCl$_3$) δ: 1.47 (3H, d, J=5.8 Hz), 1.77-1.85 (1H, m), 2.02-2.06 (1H, m), 2.46 (1H, d, J=9.9 Hz), 3.78-3.91 (3H, m), 4.39 (1H, d, J=2.5 Hz), 4.84-4.99 (2H, m), 7.16 (1H, dd, J=12.3, 8.2 Hz), 7.23 (1H, td, J=7.6, 1.0 Hz), 7.38-7.46 (4H, m), 7.50-7.54 (1H, m), 8.28 (2H, t, J=4.3 Hz), 12.10 (1H, s).

Step 3: Synthesis of Compound 11-4

The Compound 11-4 was prepared in a manner similar to the above protocols (Example 1, step 15). The yield was not determined because the product was used in the next step without purification.

MS (method B): m/z=297 [M+H]$^+$.

Step 4: Synthesis of Compound 11-5

The Compound 11-5 was prepared in a manner similar to the above protocols (Example 1, step 16). The yield was not determined because the product was used in the next step without purification.

MS (method B): m/z=342 [M+H]$^+$

Step 5: Synthesis of Compound 11-6

The Compound 11-6 was prepared in a manner similar to the above protocols (Example 1, step 17). The crude was purified by supercritical fluid chromatography (SFC) (Chiralpak (Registered trademark) IC; 40% ethanol with 0.1% diethylamine) to afford Compound 11-6 (yield; 32%, 3 steps)

MS (method B): m/z=312 [M+H]$^+$ Step 6: Synthesis of Compound I-011

The Compound 11-8 was prepared in a manner similar to the above protocols (Example 1, step 18). (yield; 71%)

$^1$H NMR (CDCl$_3$) δ: 1.45 (3H, d, J=5.8 Hz), 1.73 (2H, s), 2.32 (1H, d, J=9.9 Hz), 3.64-3.79 (3H, m), 4.11 (1H, s), 4.59-4.76 (4H, m), 6.15 (2H, dd, J=51.1, 9.2 Hz), 7.09 (1H, dd, J=10.9, 9.4 Hz), 7.50 (1H, t, J=3.3 Hz), 7.98-7.99 (1H, m), 8.25 (1H, s), 9.05 (1H, s), 9.51 (1H, s).

The following compounds are prepared in a manner similar to the above. In the tables, tR means LC/MS retention time (minute).

TABLE 1

| No. | Structure | $^1$H NMR | M + H observed | tR (min) | LC/MS method |
|---|---|---|---|---|---|
| I-047 | 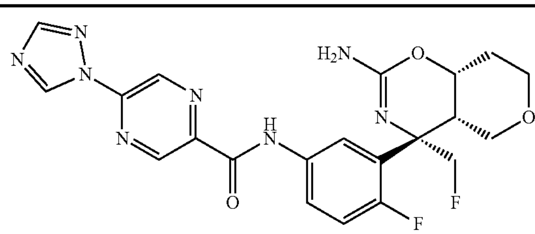 | $^1$H NMR (400 MHz, CDCl$_3$) δ: 1.75-1.88 (2H, m), 2.80-2.75 (1H, m), 3.59-3.66 (2H, m), 3.78 (1H, dd, J = 11.2, 4.8 Hz), 4.01-4.05 (1H, m), 4.10 (1H, br s), 4.37 (2H, s), 4.64 (2H, d, J = 47.1 Hz), 7.13 (1H, dd, J = 11.4, 8.8 Hz), 7.55 (1H, dd, J = 6.3, 2.4 Hz), 8.01-8.05 (1H, m), 8.22 (1H, s), 9.25 (2H, s), 9.33 (1H, br s), 9.59 (1H, brs). | 471 | 0.99 | B |
| I-055 | 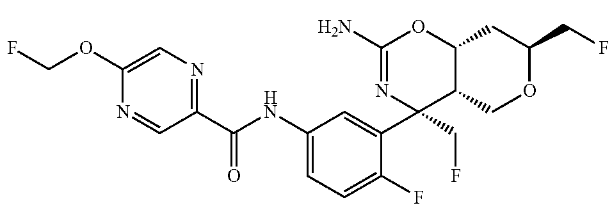 [SMILES: NC1=N[C@](CF)(c2cc(NC(=O)c3cnc(OCF)cn3)ccc2F)[C@H]2CO[C@H](CF)C[C@H]2O1] | $^1$H NMR (400 MHz, CDCl$_3$) δ: 1.18 (2H, d, J = 6.0 Hz), 1.41-1.48 (1H, m), 1.81-1.85 (1H, m), 2.69-2.74 (1H, m), 3.66-3.74 (2H, m), 4.01-4.09 (2H, m), 4.38 (2H, br s), 4.56-4.73 (2H, m), 7.12 (1H, dd, J = 11.4, 8.9 Hz), 7.54 (1H, dd, J = 6.8, 2.8 Hz), 8.00-8.05 (1H, m), 8.22 (1H, s), 9.25 (2H, s), 9.33 (1H, br s), 9.59 (1H, s). | 485 | 1.09 | B |

TABLE 1-continued

| No. | Structure | ¹H NMR | M + H observed | tR (min) | LC/MS method |
|---|---|---|---|---|---|
| I-059 | 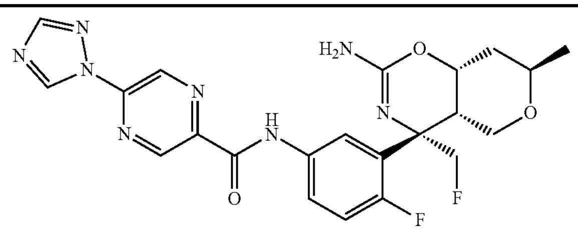 | ¹H NMR (400 MHz, CDCl$_3$) δ: 1.69-1.82 (2H, m), 2.74-2.78 (1H, m), 3.73 (1H, t, J = 11.8 Hz), 3.80-3.93 (1H, m), 4.17-4.28 (2H, m), 4.28-4.74 (6H, m), 6.15 (2H, add, J = 51.2, 9.5, 2.0 Hz), 7.11 (1H, dd, J = 11.5, 8.8 Hz), 7.51 (1H, dd, J = 6.8, 2.6 Hz), 7.95 (1H, s), 7.97-8.01 (1H, m), 8.29 (1H, d, J = 1.3 Hz), 9.08 (1H, d, J = 1.3 Hz), 9.51 (1H. brs). | 484 | 1.31 | B |
| I-061 | 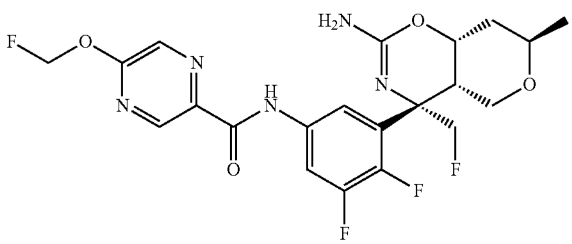 [SMILES: C[C@@H]1C[C@H]2OC(N)=N[C@](CF)(c3cc(NC(=O)c4cnc(OCF)cn4)cc(F)c3F)[C@H]2CO1] | ¹H NMR (400 MHz, CDCl$_3$) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 484 | 1.33 | B |

TABLE 2

| No. | Structure | ¹H NMR | M + H observed | tR (min) | LC/MS method |
|---|---|---|---|---|---|
| I-065 | 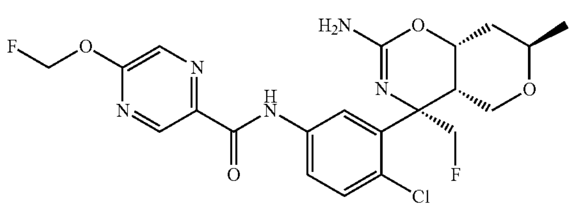 [SMILES: C[C@@H]1C[C@H]2OC(N)=N[C@](CF)(c3cc(NC(=O)c4cnc(OCF)cn4)ccc3Cl)[C@H]2CO1] | ¹H NMR (400 MHz, CDCl$_3$) δ: 1.17 (3H, d, J = 6.3 Hz), 1.41-1.48 (m, 1H), 1.79-1.84 (m, 1H), 3.15-3.20 (1H, m), 3.67-3.76 (2H, m), 3.99-4.04 (2H, m), 4.76-5.04 (2H, m), 6.15 (2H, ddd, J = 51.1, 11.5, 2.0 Hz), 7.40 (1H, d, J = 8.5 Hz), 7.63 (1H, d, J = 2.8 Hz), 8.03 (1H, dd, J = 8.7, 2.8 Hz), 8.28 (1H, d, J = 1.4 Hz), 9.07 (1H, d, J = 1.4 Hz), 9.54 (1H, brs). | 482 | 1.33 | B |
| I-067 | 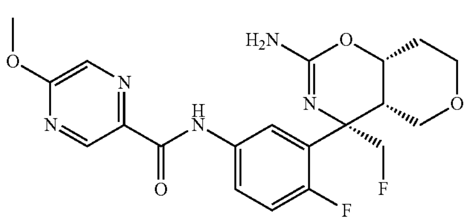 [SMILES: COc1cnc(C(=O)Nc2ccc(F)c([C@@]3(CF)N=C(N)O[C@@H]4CCOC[C@@H]43)c2)cn1] | ¹H NMR (400 MHz, CDCl$_3$) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 434 | 1.02 | B |

TABLE 2-continued
| | | | | | |
|---|---|---|---|---|---|
| I-068 | 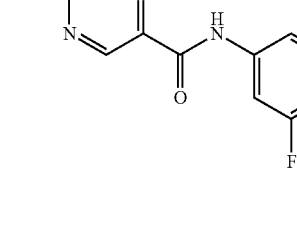 | ¹H NMR (400 MHz, CDCl₃) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 464 | 1.24 | B |
| I-069 | | ¹H NMR (400 MHz, CDCl₃) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 448 | 1.11 | B |
TABLE 3
| | | | | | |
|---|---|---|---|---|---|
| I-073 | 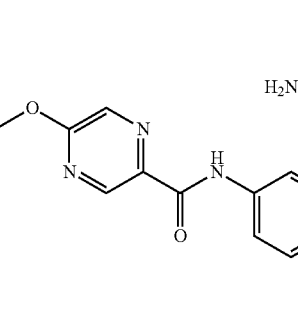 | ¹H NMR (400 MHz, CDCl₃) δ: 1.73-1.92 (2H, m), 2.75 (1H, ddd, J = 11.4, 4.9, 2.3 Hz), 3.57-3.67 (2H, m), 3.78 (1H, dd, J = 11.4, 4.9 Hz), 3.98-4.05 (1H, m), 4.07-4.10 (1H, m), 4.50-4.73 (2H, m), 6.15 (2H, ddd, J = 51.2, 11.8, 1.9 Hz), 7.16-7.20 (1H, m), 8.12 (1H, ddd, J = 11.5, 6.7, 2.6 Hz), 8.28 (1H, d, J = 1.3 Hz), 9.06 (1H, d, J = 1.3 Hz), 9.52 (1H, s). | 470 | 1.2 | B |
| I-074 | | ¹H NMR (400 MHz, CDCl₃) δ: 1.02 (3H, d, J = 7.4 Hz), 1.82-1.84 (1H, m), 2.92 (1H, ddd, J = 11.5, 5.1, 2.3 Hz), 3.50-3.62 (2H, m), 3.73-3.80 (2H, m), 4.01 (1H, dd, J = 11.5, 2.3 Hz), 4.44 (2H, br s), 4.56 (1H, s), 4.68 (1H, s), 6.15 (2H, ddd, J = 51.1, 10.3, 1.9 Hz), 7.11 (1H, dd, J = 11.5, 8.9 Hz), 7.49 (1H, dd, J = 6.8, 2.8 Hz), 8.01 (1H, ddd, J = 8.9, 4.1, 2.8 Hz), 8.28 (1H, d, J = 1.3 Hz), 9.07 (1H, d, J = 1.3 Hz), 9.51 (1H, s). | 466 | 1.12 | B |

TABLE 4

| I- | Structure | ¹H NMR | | | |
|---|---|---|---|---|---|
| I-075 | 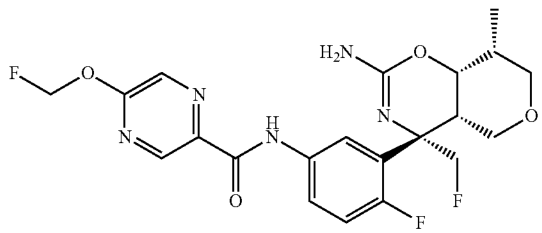 [SMILES: C[C@@H]1COC[C@H]2[C@@H]1OC(N)=N[C@]2(CF)c1cc(NC(=O)c2cnc(OCF)cn2)ccc1F] | ¹H NMR (400 MHz, CDCl₃) δ: 0.85 (3H, d, J = 7.0 Hz), 1.83-1.89 (1H, m), 2.74 (1H, ddd, J = 11.6, 4.9, 2.1 Hz), 3.32 (1H, t, J = 11.6 Hz), 3.54 (1H, t, J = 11.6 Hz), 3.62 (1H, dd, J = 11.6, 4.9 Hz), 3.87 (1H, s), 4.01 (1H, dd, J = 11.6, 2.8 Hz), 4.33 (2H, s), 4.57 (1H, s), 4.69 (1H, s), 6.15 (2H, ddd, J = 51.1, 10.5, 1.9 Hz), 7.10 (1H, dd, J = 11.5, 8.8 Hz), 7.48 (1H, dd, J = 6.8, 2.8 Hz), 8.05 (1H, ddd, J = 8.8, 4.0, 2.8 Hz), 8.28 (1H, d, J = 1.1 Hz), 9.08 (1H, d, J = 1.1 Hz), 9.52 (1H, s). | 466 | 1.13 | B |
| I-076 | 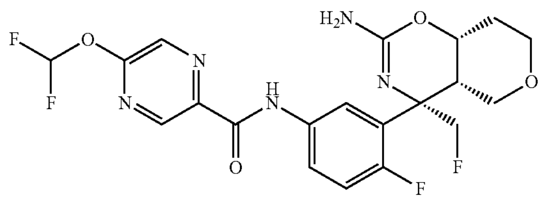 | ¹H NMR (400 MHz, CDCl₃) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 470 | 1.18 | B |
| I-077 | 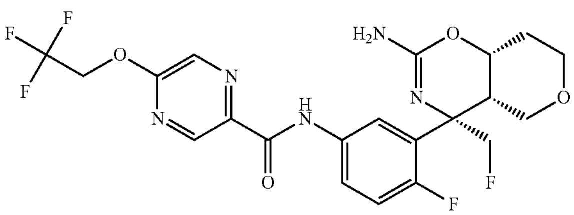 [SMILES: NC1=N[C@](CF)(c2cc(NC(=O)c3cnc(OCC(F)(F)F)cn3)ccc2F)[C@H]2COCC[C@H]2O1] | ¹H NMR (400 MHz, CDCl₃) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 502 | 135 | B |
| I-078 | 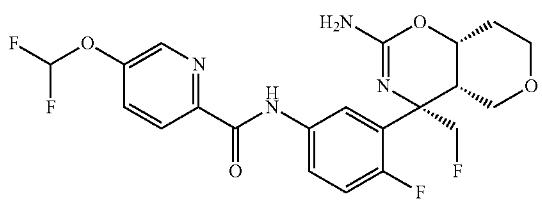 | ¹H NMR (400 MHz, CDCl₃) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 HH, s), 7.80 (1H, s), 7.93-7.99 (1H, m), 8.14 (1H, s), 9.84 (1H, s). | 469 | 1.23 | B |

TABLE 5

| I- | Structure | ¹H NMR | | | |
|---|---|---|---|---|---|
| I-079 | 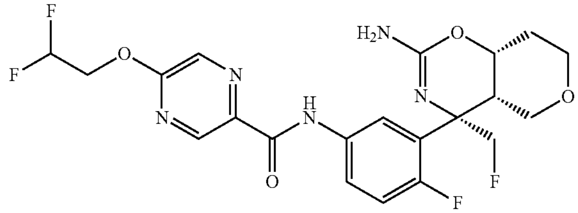 [SMILES: NC1=N[C@](CF)(c2cc(NC(=O)c3cnc(OCC(F)F)cn3)ccc2F)[C@H]2COCC[C@H]2O1] | ¹H NMR (400 MHz, CDCl₃) δ: 1.39 (3H, s), 3.31-3.37 (1H, m), 3.91-3.99 (2H, m), 3.93 (3H, s), 4.32-4.45 (5H, m), 5.07 (1H, d, J = 9.3 Hz), 7.07 (1H, t, J = 10.1 Hz), 7.40-7.45 (1H, m), 7.46 (1H, s), 7.61 (1H, s), 7.80 (1H, s), 7.93-7.99 (1H, m), 8.14 (1H, s), 9.84 (1H, s). | 484 | 1.23 | B |

TABLE 5-continued

| I-084 | (structure) | ¹H NMR (400 MHz, CDCl₃) δ: 1.69-1.89 (2H, m), 2.72-2.78 (2H, m), 3.58-3.67 (1H, m), 3.77 (1H, dd, J = 11.2, 4.8 Hz), 3.98-4.10 (2H, m), 4.27-4.49 (2H, br), 4.54-4.59 (1H, m), 4.66-4.71 (1H, m), 5.58 (2H, s), 7,09 (1H, t, J = 10.0 Hz), 7.18 (1H, s), 7.49 (1H, d, J = 6.5 Hz), 7.72 (1H, s), 7.97-8.03 (1H, m), 8.25 (1H, s), 9.02 (1H, s), 9.50 (1H, s). | 501 | 1.07 | B |
|---|---|---|---|---|---|
| I-085 | (structure) | ¹H NMR (400 MHz, CDCl₃) δ: 1.74-1.88 (3H, m), 2.73-2.79 (1H, m), 3.57-3.67 (3H, m), 3.73-3.80 (3H, m), 4.03 (1H, d, J = 9.5 Hz), 4.09 (1H, s), 4.54-4.62 (1H, m), 4.64-4.77 (4H, m), 4.83-4.89 (1H, m), 7.10 (1H, dd, J = 11.5, 8.8 Hz), 7.49 (1H, dd, J = 6.9, 2.8 Hz), 8.01 (1H, ddd, J = 10.0, 5.0, 2.5 Hz), 8.23 (1H, d, J = 1.3 Hz), 8.99 (1H, d, J = 1.4 Hz), 9.51 (1H, s). | 465 | 1.15 | A |
| I-086 | (structure) | ¹H NMR (400 MHz, CDCl₃) δ: 0.83-0.91 (2H, m), 1.19-1.30 (2H, m), 1.74-1.87 (2H, m), 2.74-2.77 (1H, m), 3.61-3.64 (2H, m), 3.75-3.78 (1H, m), 4.03 (1H, d, 1 = 9.2 Hz), 4.09 (1H, d, J = 1.6 Hz), 4.58-4.78 (4H, m), 7.09 (1H, dd, J = 11.5, 8.8 Hz), 7.49 (1H, dd, J = 6.8, 2.7 Hz), 7.98-8.02 (1H, m), 8.26 (1H, d, J = 1.3 Hz), 8.97 (1H, d, J = 1.3 Hz), 9.52 (1H, s). | 492 | 1.52 | B |

TABLE 6

| I-088 | (structure) | ¹H NMR (400 MHz, CDCl₃) δ: 1.17 (3H, d, J = 6.3 Hz), 1.41-1.48 (2H, m), 1.80-1.85 (1H, m), 2.71 (1H, ddd, J = 11.7, 5.0, 2.3Hz), 3.66-3.74 (2H, m), 4.01-4.09 (2H, m), 4.62-4.55 (1H, m), 4.67-4.73 (1H, m), 6.79 (1H, t, J = 54.5 Hz), 7.12 (1H, dd, J = 11.5, 8.8 Hz), 7.54 (1H, dd, J = 6.8, 2.6 Hz), 7.98-8.02 (1H, m), 8.93 (1H, s), 9.52 (1H, s), 9.66 (1H, s). | 468 | 1.16 | B |

TABLE 6-continued

| | | | | | |
|---|---|---|---|---|---|
| I-089 | | ¹H NMR (400 MHz, CDCl₃) δ: 1.17 (3H, d, J = 6.0 Hz), 1.40-1.47 (1H, m), 1.80-1.85 (1H, m), 2.70 (1H, ddd, J = 11.5, 4.9, 2.1Hz), 3.65-3.74 (2H, m), 4.01-4.08 (3H, m), 4.39 (1H, br s), 4.55-4.72 (2H, m), 7.10 (1H, dd, J = 11.4, 8.9 Hz), 7.33-7.69 (2H, m), 8.01-7.96 (1H, m), 8.34 (1H, d, J = 1.3 Hz), 9.07 (1H, d, J = 1.3 Hz), 9.49 (1H, s). | 484 | 1.29 | B |
| I-094 | | ¹H NMR (400 MHz, CDCl₃) δ: 1.06 (3H, t, J = 7.3 Hz), 1.72-1.89 (3H, m), 2.41 (1H, dd, J = 10.2, 2.6 Hz), 3.57-3.76 (3H, m), 4.12 (1H, d, J = 2.6 Hz), 4.34 (2H, s), 4.61-4.83 (3H, m), 7.10 (1H, dd, J = 11.5, 8.8 Hz), 7.33-7.69 (2H, m), 7.99 (1H, ddd, J = 8.8, 3.9, 3.0 Hz), 8.33 (1H, d, J = 1.0 Hz), 9.06 (1H, d, J = 1.0 Hz), 9.48 (1H, s). | 498 | 1.3 | B |

TABLE 7

| | | | | | |
|---|---|---|---|---|---|
| I-099 | | ¹H NMR (400 MHz, CDCl₃) δ ppm 1.18 (d, J = 6.51 Hz, 3H), 1.45 (ddd, J = 14.24, 11.39, 2.85 Hz, 1H), 1.81-1.86 (m, 1H), 2.70-2.75 (ddd, J = 11.6, 5.09, 2.44 Hz, 1H), 3.76 (m, 1H), 4.05 (m, 1H), 4.09 (br d, J = 2.44 Hz, 1H), 4.65 (m, 2H), 7.11 (dd, J = 8.54, 2.85 Hz, 1H), 7.56 (dd, J = 6.92, 2.85 Hz, 1H), 8.03 (m, 1H), 8.17 (dd, J = 7.93, 1.83 Hz, 1H), 8.42 (d, J = 8.14Hz, 1H), 8.88 (m, 1H) | 485 | 1.08 | C |
| I-100 | | ¹H NMR (400 MHz, CDCl₃) δ ppm 1.18 (d, J = 6 Hz, 3 H), 1.44 (ddd, J = 14.34, 11.49, 2.64 Hz, 1H), 1.80-1.85 (dt, J = 14.24, 2.64 Hz, 1H), 2.72 (m, 1H), 2.88 (s, 3H), 3.64-3.75 (m, 2H), 4.03 (br d, J = 4.48 Hz, 1H), 4.08 (m, 1H), 4.60 (s, 1H), 4.70 (s, 1H), 7.1 (dd, J = 11.6, 8.75 Hz, 1H), 7.42 (dd, J = 6.71, 2.64 Hz, 1H), 7.89 (s, 1H), 8.07 (m, 1H), 8.7 (s, 1H), 10.09 (s, 1H) | 498 | 1.12 | C |

TABLE 7-continued

| Cmpd | Structure | ¹H NMR | MS | RT | Method |
|---|---|---|---|---|---|
| I-101 | [5-(trifluoromethyl)-3-chloro-pyridine-2-carboxamide linked to phenyl(F) bearing fused aminooxazine-pyran with CH₂F] | ¹H NMR (400 MHz, CDCl₃) δ ppm 1.18 (d, J = 6.1 Hz, 3H), 1.45 (ddd, J = 14.14, 11.49, 2.44 Hz, 1H), 1.83 (dt, J = 14.24, 2.64 Hz, 1H), 2.72 (ddd, J = 11.6, 5.09, 2.44 Hz, 1H), 3.69 (m, 1H), 4.03 (br dd, J = 9.97, 4.68 Hz, 1H), 4.08 (br d, J = 2.44 Hz, 1H), 4.57 (m, 1H), 4.70 (m, 1H), 7.11 (dd, J = 11.6, 8.75 Hz, 1H), 7.4 (dd, J = 6.71, 2.64 Hz, 1H), 8.11 (m, 1H), 8,14 (m, 1H), 8.77 (m, 1H) | 519 | 1.06 | C |

TABLE 8

| Cmpd | Structure | ¹H NMR | MS | RT | Method |
|---|---|---|---|---|---|
| I-102 | [5-(trifluoromethyl)pyrazine-2-carboxamide linked to phenyl(F) bearing fused aminooxazine-pyran with CH₂F] | ¹H NMR (400 MHz, CDCl₃) δ ppm 1.77 (m, 1H), 1.80-1.89 (m, 1H), 2.77 (ddd, J = 11.6, 5.09, 2.44 Hz, 1H), 3.59-3.69 (m, 2H), 3.78 (dd, J = 11.6, 4.68 Hz, 1H), 4.03 (m, 1H), 4.09 (m, 1H), 4.55-4.74 (m, 2H) 7.12 (dd, J = 11.39, 8.95 Hz, 1H), 7.57 (dd, J = 6.92, 2.85 Hz, 1H), 7.99 (ddd, J = 8.55, 4.07, 2.85 Hz, 1H), 8.94 (d, J = 1.63 Hz, 1H), 9.59 (d, J = 1.22 Hz, 1H) | 472 | 0.89 | C |
| I-103 | [5-(difluoromethyl)pyrazine-2-carboxamide linked to phenyl(F) bearing fused aminooxazine-pyran with CH₂F] | ¹H NMR (400 MHz, CDCl₃) δ ppm 1.77 (m, 1H), 1.80-1.89 (m, 1H), 2.77 (ddd, J = 11.39, 5.09, 2.44 Hz, 1H), 3.59-3.69 (m, 2H), 3.64-3.74 (m, 2H), 3.78 (dd, J = 10.99, 4.07, 1H), 4.04 (m, 1H), 4.09 (m, 1H), 4.56-4.73 (m, 2H), 6.65 (t, J = 54.52 Hz, 1H) 7.13 (dd, J = 11.39, 8.95 Hz, 1H), 7.56 (dd, J = 6.92, 2.85 Hz, 1H), 8.01 (ddd, J = 8.65, 4.17, 2.65 Hz, 1H), 8.92 (s, 1H), 9.52 (s, 1H) | 454 | 0.77 | C |

TABLE 9
| | | | | | |
|---|---|---|---|---|---|
| I-104 |  | ¹H NMR (400 MHz, CDCl₃) δ ppm 1.75 (m, 1H), 1.78-1.88 (m, 1H), 2.76 (ddd, J = 11.39, 4.88, 2.44 Hz, 1H), 3.58-3.68 (m, 2H), 3.77 (dd, J = 11.4, 4.07, 1H), 4.01-4.06 (m, 1H), 4.08 (m, 1H), 4.54-4.74 (m, 2H) 7.09 (dd, J = 11.6, 8.75 Hz, 1H), 7.51 (dd, J = 6.92, 2.85 Hz, 1H), 8 (ddd, J = 8.75, 4.27, 2.85 Hz, 1H), 8.14 (d, J = 1.23 Hz, 1H), 9 (d, J = 1.63 Hz, 1H) | 437 | 0.76 | C |
| I-105 | | ¹H NMR (400 MHz, CDCl₃) δ ppm 1.77 (m, 1H), 1.79-1.89 (m, 1H), 2.77 (ddd, J = 11.6, 5.09, 2.44 Hz, 1H), 3.60-3.69 (m, 2H), 3.77 (dd, J = 11.39, 4.48, 1H), 4.03 (m, 1H), 4.09 (m, J = 2.85, 1H), 4.56-4.73 (dd, J = 47.2, 1.63 Hz, 2H) 7.11 (dd, J = 11.6, 8.75 Hz, 1H), 7.57 (dd, J = 6.71, 2.64 Hz, 1H), 8.03 (ddd, J = 8.54, 4.07, 2.85 Hz, 1H), 8.17 (dd, J = 8.14, 1.63 Hz, 1H), 8.43 (d, J = 8.14 Hz, 1H), 8.89 (m, 1H) | 471 | 0.87 | C |
45
TABLE 10
| | | | | | |
|---|---|---|---|---|---|
| I-106 | 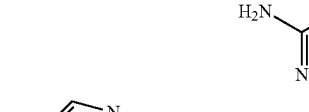 | ¹H NMR (400 MHz, CDCl₃) δ ppm 1.75 (m, 1H), 1.77-1.87 (m, 1H), 2.76 (ddd, J = 11.49, 4.98, 2.24 Hz, 1H), 2.82 (s, 1H), 3.58-3.69 (m, 2H), 3.76 (dd, J = 11.39, 4.48, 1H), 4.03 (m, 1H), 4.06 (m, J = 2.03, 1H), 4.56-4.76 (m, 2H), 7.04 (dd, J = 11.6, 8.75 Hz, 1H), 7.49 (dd, J = 6.92, 2.85 Hz, 1H), 7.85 (d, J = 0.81 Hz, 1H), 7.99 (ddd, J = 8.95, 4.07, 2.85 Hz, 1H), 8.58 (s, 1H) | 485 | 0.93 | C |

TABLE 10-continued

| | | | | | |
|---|---|---|---|---|---|
| I-107 | 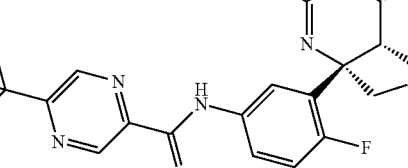 | $^1$H NMR (400 MHz, CHLOROFORM-d) δ ppm 1.71-1.79 (m, 1H) 1.79-1.89 (m, 1 H) 2.03-2.16 (m, 3 H) 2.76 (ddd, J = 11.60, 5.09, 2.44 Hz, 1 H) 3.59-3.68 (m, 2 H) 3.74-3.80 (m, 1 H) 4.02 (br dd, J = 10.38, 4.27 Hz, 1 H) 4.08 (br d, J = 2.44 Hz, 1 H) 4.59 (qd, J = 8.90, 1.80 Hz, 1 H) 4.67-4.75 (m, 1 H) 7.10 (dd, J = 11.60, 8.75 Hz, 1 H) 7.59 (dd, J = 6.92, 2.85 Hz, 1 H) 7.98 (ddd, J = 8.95, 4.07, 2.85 Hz, 1 H) 8.88 (d, J = 1.22 Hz, 1 H) 9.45 (d, J = 1.00 Hz, 1 H) 9.64 (s, 1 H) | 468 | 1.67 | D |

TABLE 11

| | | | | | |
|---|---|---|---|---|---|
| I-108 | | $^1$H NMR (400 MHz, CDCl$_3$) δ ppm 1.76 (m, 1H), 1.79-1.89 (m, 1H), 2.77 (ddd, J = 11.5, 4.98, 2.24 Hz, 1H), 3.58-3.69 (m, 2H), 3.77 (dd, J = 10.99, 4.07, 1H), 4.02 (m, 1H), 4.08 (m, J = 2.44, 1H), 4.54-4.72 (m, 2H) 7.1 (dd, J = 11.39, 8.95 Hz, 1H), 7.43 (dd, J = 6.71, 2.64 Hz, 1H), 8.08 (ddd, J = 8.54, 4.07, 2.85 Hz, 1H), 8.12 (m, 1H), 8.75 (m, 1H) | 505 | 0.87 | C |
| I-109 | | $^1$H NMR (400 MHz, CDCl$_3$) δ ppm 1.45 (t, J = 7.1 Hz, 3H), 1.75-1.88 (m, 3H), 2.78 (d, J = 9.3 Hz, 1H), 3.62 (t, J = 11.7 Hz, 2H), 3.78 (dd, J = 11.3, 4.9 Hz, 1H), 4.04 (d, J = 11.7 Hz, 1H), 4.12 (s, 1H), 4.49 (q, J = 7.1 Hz, 2H), 4.55-4.63 (m, 1H), 4.67-4.78 (m, 1H), 7.10 (dd, J = 11.5, 9.0 Hz, 1H), 7.48 (dd, J = 6.9, 2.8 Hz, 1H), 7.99-8.03 (m, 1H), 7.99-7.99 (m, 1H), 8.12 (d, J = 1.4 Hz, 1H), 8.99 (d, J = 1.4 Hz, 1H), 9.53 (s, 1H). | 448 | 1.21 | B |

TABLE 12

| No. | Structure | NMR | M+H | tR | LC/MS Method |
|---|---|---|---|---|---|
| I-110 | [Structure: 5-(trideuteromethoxy)-3-methyl-pyridine-2-carboxamide linked to N-H to 3-(spirocyclic aminooxazine with CH2F and methyl substituents)-4-fluorophenyl] | ¹H NMR (400 MHz, CDCl₃) δ ppm 1.18 (d, J = 6.1 Hz, 3H), 1.44 (ddd, J = 14.14, 11.49, 2.44 Hz, 1H), 1.82 (dt, J = 14.37, 2.83 Hz, 1H), 2.7 (ddd, J = 11.6, 5.09, 2.44 Hz, 1H), 3.62-3.76 (m, 2H), 4.04 (m, 1H), 4.08 (m, 1H), 4.54-4.72 (dd, J = 46.79, 1.00 Hz, 2H) 7.09 (dd, J = 11.6, 8.75 Hz, 1H), 7.49 (dd, J = 6.92, 2.85 Hz, 1H), 8.01 (ddd, J = 8.95, 4.07, 2.85 Hz, 1H), 8.14 (d, J = 1.22 Hz, 1H), 9.01 (d, J = 1.22 Hz, 1H) | 451 | 0.79 | C |

TABLE 13

| No. | Structure | M + H observed | tR (min) | LC/MS Method |
|---|---|---|---|---|
| II-1 | [Structure: 5-(fluoromethoxy)pyrazine-2-carboxamide linked via N-H to 3-(spirocyclopropyl aminooxazine with CH2F)-4-fluorophenyl] | 478 | 1.06 | B |
| II-2 | [Structure: 5-(fluoromethoxy)pyrazine-2-carboxamide linked via N-H to 3-(methyl-substituted aminooxazine with CH2F)-4-fluorophenyl] | 466 | 1.09 | B |
| II-3 | [Structure: 5-(fluoromethoxy)pyrazine-2-carboxamide linked via N-H to 3-(CHF2-substituted aminooxazine with CH2F)-4-fluorophenyl] | 502 | 1.11 | B |

TABLE 14

| No. | NMR |
|---|---|
| II-1 | 1H NMR (400 MHz, CDCk3) δ: 0.41-0.52 (2H, m), 0.77-0.81 (2H, m), 1.33 (1H, dd, J = 14.5, 2.9 Hz), 2.31 (1H, dd, J = 14.5, 2.9 Hz), 2.82 (1H, dq, J = 11.5, 2.9 Hz), 3.78 (1H, t, J = 11.5 Hz), 3.92-3.94 (1H, m), 4.13 (1H, d, J = 2.9 Hz), 4.38 (2H, br s), 4.60-4.72 (2H, m), 6.09 (1H, dd, J = 9.6, 1.8 Hz), 6.21 (1H, dd, J = 9.6, 1.8 Hz), 7.11 (1H, dd, J = 11.4, 8.9 Hz), 7.51 (1H, dd, J = 6.8, 3.5 Hz), 8.01 (1H, dt, J = 8.9, 3.5 Hz), 8.28 (1H, s), 9.07 (1H, s), 9.50 (1H, s). |
| II-2 | 1H-NMR (CDCl3) δ: 1.36 (3H, d, J = 6.9 Hz), 1.76 (1H, dd, J = 14.7, 3.4 Hz), 1.93 (1H, dq, J = 14.7, 3.4 Hz), 2.71 (1H, ddd, J = 11.2, 4.9, 3.4 Hz), 3.78 (1H, dd, J = 11.2, 4.9 Hz), 3.93-3.96 (1H, m), 4.05-4.10 (2H, m), 4.38 (2H, br s), 4.68 (2H, d, J = 47.2 Hz), 6.09 (1H, dd, J = 9.8, 1.8 Hz), 6.21 (1H, dd, J = 9.8, 1.8 Hz), 7.10 (1H, dd, J = 11.5, 8.8 Hz), 7.49 (1H, dd, J = 6.8, 3.5 Hz), 8.00 (1H, dt, J = 8.7, 3.5 Hz), 8.28 (1H, s), 9.07 (1H, s), 9.50 (1H, s). |
| II-3 | 1H-NMR (CDCl3) δ: 1.70 (1H, t, J = 13.9 Hz), 1.93 (1H, d, J = 13.9 Hz), 2.78 (1H, dd, J = 11.6, 5.0 Hz), 3.71-3.89 (2H, m), 4.18-4.35 (4H, m), 4.56-4.69 (2H, m), 5.72 (1H, td, J = 55.5, 3.2 Hz), 6.09 (1H, d, J = 7.5 Hz), 6.22 (1H, d, J = 7.5 Hz), 7.11 (1H, t, J = 10.2 Hz), 7.53 (1H, dd, J = 6.4, 2.0 Hz), 7.97-8.01 (1H, m), 8.29 (1H, s), 9.08 (1H, s), 9.51 (1H, s). |

Test Examples for the compounds of the present invention are mentioned below.

PHARMACOLOGICAL EXAMPLES

The compounds provided in the present invention are inhibitors of the beta-site APP-cleaving enzyme 1 (BACE1). Inhibition of BACE1, an aspartic protease, is believed to be relevant for treatment of Alzheimer's Disease (AD). The production and accumulation of beta-amyloid peptides (Abeta) from the beta-amyloid precursor protein (APP) is believed to play a key role in the onset and progression of AD. Abeta is produced from the amyloid precursor protein (APP) by sequential cleavage at the N- and C-termini of the Abeta domain by BACE1 and gamma-secretase, respectively.

Compounds of the present invention are expected to have their effect selectively at BACE1 versus BACE2 by virtue of their ability to selectively bind to BACE1 versus BACE2 and inhibit the BACE1 versus BACE2 enzymatic activity. The behaviour of such inhibitors is tested using a biochemical competitive radioligand binding assay, a biochemical Fluorescence Resonance Energy Transfer (FRET) based assay and a cellular αLisa assay described below, which are suitable for the identification of such compounds.

Test Example 1: BACE1 and BACE2 Biochemical Competitive Radioligand Binding Assay To explore the BACE1 versus BACE2 enzyme selectivity, the binding affinity (Ki) to the respective purified enzymes was determined in a competitive radioligand binding assay, i.e. in competition with a tritiated non-selective BACE1/BACE 2 inhibitor.

Briefly in test tubes, compounds of interest were combined with the radioligand and the BACE1 or BACE2-containing HEK 293 derived membrane. The competitive binding reaction was performed at pH 6.2 and incubated at room temperature until the equilibrium was reached. Afterwards free radioligand was separated from bound radioligand by filtration with a Brandell 96 harvester. The filter was washed 4 times with washing buffer and the filter sheets were punched into scintillation vials. Ultima Gold scintillation cocktail was added and samples were shaken. The day after, the vials were counted in a Tricarb scintillation counter to obtain the disintegrations per minute (dpm) of the bound radioligand.

Calculating the % CTL=(sample/HC)*100, with HC being the high control, i.e. total binding of radioligand, allowed to fit curves through the data points of the different doses of test compound. The $pIC_{50}$ or $IC_{50}$ was calculated and could be converted to $K_i$ by the formula $K_i=IC_{50}/(1+([RL]/K_d))$, with [RL] being the used concentration of radioligand and $K_d$ the determinated dissociation constant of the radioligand-membrane complex.

Test Example 2

(1) BACE1 Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) beta-site secretase cleavage site. This substrate also contains two fluorophores: (7-methoxycoumarin-4-yl) acetic acid (Mca) is a fluorescent donor with excitation wavelength at 320 nm and emission at 405 nm and 2,4-dinitrophenol (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis.

Briefly in a 384-well format recombinant BACE1 protein in a final concentration of 0.04 μg/mL was incubated for 450 minutes at room temperature with 20 μm substrate in incubation buffer (final concentrations: 33.3 mM Citrate buffer pH 5.0, 0.033% PEG, 3% DMSO) in the absence or presence of compound. Next the amount of proteolysis was directly measured by fluorescence measurement at T=0'-120' and T=450' (excitation at 320 nm and emission at 405 nm). Results were expressed in RFU (Relative Fluorescence Units), as difference between T450 and Tx (Tx is chosen depending on the reaction speed between 0 and 120 minutes).

A best-fit curve was fitted by a minimum sum of squares method to the plot of % Controlmin versus compound concentration. From this an $IC_{50}$ value (inhibitory concentration causing 50% inhibition of activity) can be obtained.
LC=Median of the low control values
=Low control: Reaction without enzyme
HC=Median of the High control values
=High Control: Reaction with enzyme % Effect=100−[(sample−LC)/(HC−LC)*100]

% Control=(sample/HC)*100

% Controlmin=(sample−LC)/(HC−LC)*100

A compound of the present invention are expected to have BACE1 inhibiting activity, and it is sufficient that the compound can inhibit the BACE1 receptor.

Specifically, by the protocol above shown, IC50 is preferably 5000 nM or less, more preferably 1000 nM or less, further preferably 100 nM or less.

(2) BACE2 Biochemical FRET Based Assay

This assay is a Fluorescence Resonance Energy Transfer Assay (FRET) based assay. The substrate for this assay contains the 'Swedish' Lys-Met/Asn-Leu mutation of the amyloid precursor protein (APP) beta-secretase cleavage site. This substrate also contains two fluorophores: (7-methoxycoumarin-4-yl) acetic acid (Mca) is a fluorescent donor with excitation wavelength at 320 nm and emission at 405 nm and 2,4-dinitrophenol (Dnp) is a proprietary quencher acceptor. The distance between those two groups has been selected so that upon light excitation, the donor fluorescence energy is significantly quenched by the acceptor, through resonance energy transfer. Upon cleavage by the beta-secretase, the fluorophore Mca is separated from the quenching group Dnp, restoring the full fluorescence yield of the donor. The increase in fluorescence is linearly related to the rate of proteolysis.

Briefly in a 384-well format recombinant BACE2 protein in a final concentration of 0.4 μg/mL was incubated for 450 minutes at room temperature with 10 μM substrate in incubation buffer (final concentrations: 33.3 mM Citrate buffer pH 5.0, 0.033% PEG, 2% DMSO) in the absence or presence of compound. Next the amount of proteolysis was directly measured by fluorescence measurement at T=0 and T=450 (excitation at 320 nm and emission at 405 nm). Results were expressed in RFU (Relative Fluorescence Units), as difference between T450 and T0.

A best-fit curve was fitted by a minimum sum of squares method to the plot of % Controlmin versus compound concentration. From this an $IC_{50}$ value (inhibitory concentration causing 50% inhibition of activity) can be obtained.
LC=Median of the low control values
=Low control: Reaction without enzyme
HC=Median of the High control values
=High Control: Reaction with enzyme % Effect=100−[(sample−*LC*)/(*HC*−*LC*)\*100]

% Control=(sample/*HC*)\*100

% Controlmin=(sample−*LC*)/(*HC*−*LC*)\*100

The following exemplified compounds were tested essentially as described above and exhibited the following activity:

TABLE 15

| No. | BACE1 IC50 (nM) | BACE2 IC50 (nM) | Selectivity |
| --- | --- | --- | --- |
| I-007 | 7.4 | 302 | 40.7 |
| I-008 | 14.8 | 646 | 43.7 |
| I-009 | 15.5 | 692 | 44.7 |
| I-010 | 10.7 | 457 | 42.7 |
| I-011 | 13.2 | 417 | 31.6 |
| I-047 | 17.0 | 1175 | 69.2 |
| I-059 | 8.7 | 302 | 34.7 |
| I-061 | 17.4 | 933 | 53.7 |
| I-065 | 9.5 | 339 | 35.5 |
| I-067 | 8.9 | 269 | 30.2 |
| I-068 | 11.2 | 275 | 24.5 |
| I-069 | 11.7 | 1445 | 123 |
| I-074 | 4.3 | 155 | 36.3 |
| I-075 | 26 | 724 | 27.5 |
| I-076 | 2.8 | 178 | 63.1 |
| I-077 | 8.1 | 1820 | 223 |
| I-078 | 9.8 | 245 | 25.1 |
| I-079 | 18.6 | 1000 | 52.7 |
| I-086 | 10.0 | 537 | 53.7 |
| I-088 | 55.0 | 617 | 11.2 |
| I-089 | 9.8 | 550 | 56.2 |

TABLE 15-continued

| No. | BACE1 IC50 (nM) | BACE2 IC50 (nM) | Selectivity |
| --- | --- | --- | --- |
| I-094 | 5.9 | 417 | 70.8 |
| I-099 | 19.1 | 550 | 28.8 |
| I-100 | 16.6 | 257 | 15.5 |

TABLE 16

| No. | BACE1 IC50 (nM) | BACE2 IC50 (nM) | Selectivity |
| --- | --- | --- | --- |
| I-101 | 28.2 | 398 | 14.1 |
| I-102 | 33.9 | 977 | 28.8 |
| I-103 | 21.9 | 316 | 14.5 |
| I-104 | 14.5 | 398 | 27.5 |
| I-105 | 17.0 | 302 | 17.8 |
| I-106 | 14.2 | 148 | 10.2 |
| I-107 | 53.7 | 3388 | 63.1 |
| I-108 | 20.0 | 200 | 10.0 |
| I-109 | 22.4 | 417 | 18.6 |
| II-1 | 21.9 | 977 | 44.7 |

Test Example 3-1: Lowering Effect on the Brain ß Amyloid in Rats

Compound of the present invention is suspended in 0.5% methylcellulose, the final concentration is adjusted to 2 mg/mL, and this is orally administered to male Crl:SD rat (7 to 9 weeks old) at 10 mg/kg. In a vehicle control group, only 0.5% methylcellulose is administered, and an administration test is performed at 3 to 8 animals per group. A brain is isolated 3 hours after administration, a cerebral hemisphere is isolated, a weight thereof is measured, the hemisphere is rapidly frozen in liquid nitrogen, and stored at −80° C. until extraction date. The frozen cerebral hemisphere is transferred to a homogenizer manufactured by Teflon (Registered trademark) under ice cooling, a 4-fold volume of a weight of an extraction buffer (containing 1% CHAPS ({3-[(3-chloroamidopropyl)dimethylammonio]-1-propanesulfonate}), 20 mmol/L Tris-HCl (pH 8.0), 150 mmol/L NaCl, Complete (Roche) protease inhibitor) is added, up and down movement is repeated, and this is homogenized to solubilize for 2 minutes. The suspension is transferred to a centrifugation tube, allowed to stand on an ice for 3 hours or more and, thereafter centrifuged at 100,000×g, 4° C. for 20 minutes. After centrifugation, the supernatant is transferred to an ELISA plate (product No. 294-62501, Wako Junyaku Kogyo) for measuring ß amyloid 40. ELISA measurement is performed according to the attached instruction. The lowering effect is calculated as a ratio compared to the brain ß amyloid 40 level of vehicle control group of each test.

Test Example 3-2: Lowering Effect on the Brain ß Amyloid in Mice

Compound of the present invention was dissolved in 20% hydroxyl-beta-cyclodextrin, the final concentration was adjusted to 2 mg/mL, and this was orally administered to male Crl:CD1 (1CR) mouse (6 to 8 weeks old) at 1 to 10 mg/kg. In a vehicle control group, only 20% hydroxyl-beta-cyclodextrin was administered, and an administration test was performed at 3 to 6 animals per group. A brain was isolated 1 to 6 hours after administration, a cerebral hemisphere was isolated, a weight thereof was measured, the hemisphere was rapidly frozen in liquid nitrogen, and stored at −80° C. until extraction date.

The frozen cerebral hemisphere was transferred to a homogenize tube containing ceramic beads in a 8-fold volume of a weight of an extraction buffer (containing 0.4% DEA (diethylamine), 50 mmol/L NaCl, Complete protease inhibitor (Roche)) and incubated on an ice for 20 minutes. Thereafter, the homogenization was done using MP BIO FastPrep (Registered trademark)-24 with Lysing matrix D 1.4 mm ceramic beads (20 seconds at 6 m/s). Then, the tube spins down for 1 minute, the supernatant was transferred to a centrifugation tube, and centrifuged at 221,000×g, 4C for 50 minutes. After centrifugation, the supernatant was transferred to Nunc Maxisorp (Registered trademark) plate (Thermo Fisher Scientific) coating with antibody against N-terminal of ß amyloid for measuring total ß amyloid, and the plate was incubated overnight at 4° C. The plate was washed with TBS-T (Tris buffered saline containing 0.05% Triton X-100), and HRP-conjugated 4G8 dissolved in PBS (pH 7.4) containing 0.1% casein was added in the plate and incubated at 4° C. for 1 hour. After it was washed with TBS-T, SuperSignal ELISA Pico Chemiluminescent Substrate (Thermo Scientific) was added in the plate. Then, the chemi-luminescence counting was measured by ARVO (Registered trademark) MX 1420 Multilabel Counter (Perkin Elmer) as soon as possible. The lowering effect was calculated as a ratio compared to the brain total ß amyloid level of vehicle control group of each test.

Test Example 4-1: CYP3A4 Fluorescent MBI Test

The CYP3A4 fluorescent MBI test is a test of investigating enhancement of CYP3A4 inhibition of a compound by a metabolism reaction. 7-benzyloxytrifluoromethylcoumarin (7-BFC) is debenzylated by the CYP3A4 enzyme (enzyme expressed in *Escherichia coli*) and 7-hydroxytrifluoromethylcoumarin (7-HFC) is produced as a fluorescing metabolite. The test is performed using 7-HFC production reaction as a marker reaction.

The reaction conditions are as follows: substrate, 5.6 µmol/L 7-BFC; pre-reaction time, 0 or 30 minutes; substrate reaction time, 15 minutes; reaction temperature, 25° C. (room temperature); CYP3A4 content (expressed in *Escherichia coli*), 62.5 µmol/mL at pre-reaction time, 6.25 µmol/mL (10-fold dilution) at reaction time; concentrations of the compound of the present invention, 0.625, 1.25, 2.5, 5, 10, 20 µmol/L (6 points).

An enzyme in a K-Pi buffer (pH 7.4) and a compound of the present invention solution as a pre-reaction solution are added to a 96-well plate at the composition of the pre-reaction. A part of pre-reaction solution is transferred to another 96-well plate, and diluted 10-fold by a substrate in a K-Pi buffer. NADPH as a co-factor is added in order to initiate a marker reaction (without preincubation). After a predetermined time of the marker reaction, acetonitrile/0.5 mol/L Tris (trishydroxyaminomethane)=4/1 (v/v) solution is added in order to terminate the marker reaction. On the other hand, NADPH is also added to a remaining pre-reaction solution in order to initiate a pre-reaction (with preincubation). After a predetermined time of a pre-reaction, a part is transferred to another 96-well plate, and diluted 10-fold by a substrate in a K-Pi buffer in order to initiate the marker reaction. After a predetermined time of the marker reaction, acetonitrile/0.5 mol/L Tris (trishydroxyaminomethane)=4/1 (v/v) solution is added in order to terminate the marker reaction. Fluorescent values of 7-HFC as a metabolite are measured in each index reaction plate with a fluorescent plate reader (Ex=420 nm, Em=535 nm).

The sample adding DMSO to a reaction system instead of compound of the present invention solution is adopted as a control (100%) because DMSO is used as a solvent to dissolve a compound of the present invention. Remaining activity (%) is calculated at each concentration of the compound of the present invention added as the solution, and $IC_{50}$ value is calculated by reverse-presumption using a logistic model with a concentration and an inhibition rate. When a difference subtracting $IC_{50}$ value with preincubation from that without preincubation is 5 µM or more, this is defined as positive (+). When the difference is 3 µM or less, this is defined as negative (−).

(Test Example 4-2: CYP3A4(MDZ) MBI Test)

CYP3A4(MDZ) MBI test is a test of investigating mechanism based inhibition (MBI) potential on CYP3A4 inhibition of a compound. CYP3A4 inhibition is evaluated using 1-hydroxylation reaction of midazolam (MDZ) by pooled human liver microsomes as a marker reaction.

The reaction conditions were as follows: substrate, 10 µmol/L MDZ; pre-reaction time, 0 or 30 minutes; substrate reaction time, 2 minutes; reaction temperature, 37° C.; protein content of pooled human liver microsomes, 0.5 mg/mL at pre-reaction time, 0.05 pmg/mL (at 10-fold dilution) at reaction time; concentrations of the compound of the present invention, 1, 5, 10, 20 µmol/L (4 points).

Pooled human liver microsomes in a K-Pi buffer (pH 7.4) and a compound of the present invention solution as a pre-reaction solution were added to a 96-well plate at the composition of the pre-reaction. A part of pre-reaction solution was transferred to another 96-well plate, and diluted 10-fold by a substrate in a K-Pi buffer. NADPH as a co-factor was added to initiate the marker reaction (without preincubation). After a predetermined time of the marker reaction, methanol/acetonitrile=1/1 (v/v) solution was added in order to terminate the marker reaction. On the other hand, NADPH was also added to a remaining pre-reaction solution in order to initiate a pre-reaction (with preincubation). After a predetermined time of a pre-reaction, a part was transferred to another 96-well plate, and diluted 10-fold by a substrate in a K-Pi buffer in order to initiate the marker reaction. After a predetermined time of the marker reaction, methanol/acetonitrile=1/1 (v/v) solution is added in order to terminate the marker reaction. After centrifuged at 3000 rpm for 15 minutes, 1-hydroxymidazolam in the supernatant is quantified by LC/MS/MS.

The sample adding DMSO to a reaction system instead of compound of the present invention solution was adopted as a control (100%) because DMSO is used as a solvent to dissolve a compound of the present invention. Remaining activity (%) was calculated at each concentration of the compound of the present invention added as the solution, and $IC_{50}$ value was calculated by reverse-presumption using a logistic model with a concentration and an inhibition rate. Shifted IC value was calculated as "IC value without preincubation (0 minutes)/IC value with preincubation (30 minutes)". When a shifted IC value was 1.5 or more, this was defined as positive. When a shifted IC value was less than 1.1, this was defined as negative.

TABLE 17

| No. | MBI MDZ |
|---|---|
| I-007 | Negative |
| I-008 | Negative |
| I-047 | Negative |
| I-059 | Negative |
| I-065 | Negative |
| I-067 | Negative |
| I-076 | Negative |
| I-105 | Negative |

Test Example 5: CYP Inhibition Test

The CYP inhibition test is a test to assess the inhibitory effect of a compound of the present invention towards typical substrate metabolism reactions on CYP enzymes in human liver microsomes. The marker reactions on human main five CYP enzymes (CYP1A2, 2C9, 2C19, 2D6, and 3A4) were used as follows; 7-ethoxyresorufin O-deethylation (CYP1A2), tolbutamide methyl-hydroxylation (CYP2C9), mephenytoin 4'-hydroxylation (CYP2C19), dextromethorphan 0-demethylation (CYP2D6), and terfenadine hydroxylation (CYP3A4). The commercially available pooled human liver microsomes were used as an enzyme resource.

The reaction conditions were as follows: substrate, 0.5 μmol/L ethoxyresorufin (CYP1A2), 100 μmol/L tolbutamide (CYP2C$_9$), 50 μmol/L S-mephenytoin (CYP2C$_{19}$), 5 μmol/L dextromethorphan (CYP2D6), 1 μmol/L terfenadine (CYP3A4); reaction time, 15 minutes; reaction temperature, 37° C.; enzyme, pooled human liver microsomes 0.2 mg protein/mL; concentrations of the compound of the present invention, 1, 5, 10, 20 μmol/L (4 points). Five kinds of substrates, human liver microsomes, and a compound solution of the present invention in 50 mmol/L Hepes buffer were added to a 96-well plate at the composition as described above as a reaction solution. NADPH as a cofactor was added to this 96-well plate in order to initiate marker reactions. After the incubation at 37° C. for 15 minutes, a methanol/acetonitrile=1/1 (v/v) solution was added in order to terminate the marker reactions. After the centrifugation at 3000 rpm for 15 minutes, resorufin (CYP1A2 metabolite) in the supernatant was quantified by a fluorescent plate reader or LC/MS/MS, and hydroxytolbutamide (CYP2C9 metabolite), 4'-hydroxymephenytoin (CYP2C19 metabolite), dextrorphan (CYP2D6 metabolite), and terfenadine alcohol metabolite (CYP3A4 metabolite) in the supernatant were quantified by LC/MS/MS.

The sample adding DMSO to a reaction system instead of compound of the present invention solution was adopted as a control (100%) because DMSO was used as a solvent to dissolve a compound of the present invention. Remaining activity (%) was calculated at each concentration of a compound of the present invention, and IC$_{50}$ value was calculated by reverse presumption using a logistic model with a concentration and an inhibition rate.

Test Example 6: Fluctuation Ames Test

Each 20 μL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 7.70 to 8.00 mL of TA98 culture is centrifuged (2000× g, 10 minutes) to remove medium, and the bacteria is suspended in 7.70 mL of Micro F buffer (K$_2$HPO$_4$: 3.5 g/L, KH$_2$PO$_4$: 1 g/L, (NH$_4$)$_2$SO$_4$: 1 g/L, trisodium citrate dihydrate: 0.25 g/L, MgSO$_4$ 7H$_2$O: 0.1 g/L), and the suspension is added to 120 mL of Exposure medium (Micro F buffer containing Biotin: 8 μg/mL, histidine: 0.2 μg/mL, glucose: 8 mg/mL). 3.10 to 3.42 mL of TA100 culture is added to 130 mL of Exposure medium to prepare the test bacterial solution. 588 μL of the test bacterial solution (or mixed solution of 498 PL of the test bacterial solution and 90 μL of the S9 mix in the case with metabolic activation system) are mixed with each 12 μL of the following solution: DMSO solution of the compound of the present invention (several stage dilution from maximum dose 50 mg/mL at 2 to 3-fold ratio); DMSO as negative control; 50 μg/mL of 4-nitroquinoline-1-oxide DMSO solution as positive control for TA98 without metabolic activation system; 0.25 μg/mL of 2-(2-furyl)-3-(5-nitro-2-furyl)acrylamide DMSO solution as positive control for TA100 without metabolic activation system; 40 μg/mL of 2-aminoanthracene DMSO solution as positive control for TA98 with metabolic activation system; or 20 μg/mL of 2-aminoanthracene DMSO solution as positive control for TA100 with metabolic activation system. A mixed solution is incubated at 37° C. under shaking for 90 minutes. 460 μL of the bacterial solution exposed to the compound of the present invention is mixed with 2300 μL of Indicator medium (Micro F buffer containing biotin: 8 μg/mL, histidine: 0.2 μg/mL, glucose: 8 mg/mL, Bromo Cresol Purple: 37.5 μg/mL), each 50 μL is dispensed into 48 wells/dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose is counted, and evaluate the mutagenicity by comparing with the negative control group. (−) means that mutagenicity is negative and (+) means positive.

Test Example 7: Solubility Test

The solubility of each compound of the present invention was determined under 1% DMSO addition conditions. A 10 mmol/L solution of the compound was prepared with DMSO, and 2 μL of the compound of the present invention solution was added, respectively, to 198 μL of JP 1st fluid (water was added to 2.0 g of sodium chloride and 7.0 mL of hydrochloric acid to reach 1000 mL) and JP 2nd fluid (1 volume of water was added to 1 volume of the solution which 3.40 g of potassium dihydrogen phosphate and 3.55 g of anhydrous disodium hydrogen phosphate dissolve in water to reach 1000 mL). The mixture was left standing for 16 hours at 25° C. or shaken for 1 hour at room temperature, and the mixture was vacuum-filtered. The filtrate was ten or one hundred-fold diluted with methanol/water=1/1 (v/v) or MeCN/MeOH/H$_2$O(=1/1/2), and the compound concentration in the filtrate was measured with LC/MS or solid phase extraction (SPE)/MS by the absolute calibration method.

Test Example 8: Metabolic Stability Test

Using a commercially available pooled human liver microsomes, a compound of the present invention was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The compound of the present invention in the supernatant was quantified by LC/MS/MS or solid phase extraction (SPE)MS, and a remaining amount of the compound of the present invention after the reaction was calculated, letting a compound amount at 0 minute reaction time to be 100%.

TABLE 18

| No. | Remaining rate(%) at 30 min |
| --- | --- |
| I-007 | 107 |
| I-008 | 94.4 |
| I-047 | 61.6 |
| I-059 | 103 |
| I-065 | 79.6 |
| I-067 | 91.4 |
| I-076 | 91.7 |
| I-105 | 87.9 |

Test Example 9: hERG Test

For the purpose of assessing risk of an electrocardiogram QT interval prolongation, effects on delayed rectifier K+ current ($I_{Kr}$), which plays an important role in the ventricular repolarization process of the compound of the present invention, was studied using CHO cells expressing human ether-a-go-go related gene (hERG) channel.

A cell was retained at a membrane potential of −80 mV by whole cell patch clamp method using an automated patch clamp system (QPatch; Sophion Bioscience A/S). After application of leak potential at −50 mV, $I_{Kr}$ induced by depolarization pulse stimulation at +20 mV for 2 seconds and, further, repolarization pulse stimulation at −50 mV for 2 seconds was recorded.

After the generated current was stabilized, extracellular solution (NaCl: 145 mmol/L, KCl: 4 mmol/L, CaCl$_2$: 2 mmol/L MgCl$_2$: 1 mmol/L, 1 mmol/L, HEPES(4-(2 hydroxyethyl)-1-piperazineethanesulfonic acid: 10 mmol/L, glucose: 10 mmol/L pH=7.4) in which the compound of the present invention have been dissolved at an objective concentration was applied to the cell under the room temperature condition for 10 minutes. From the recording $I_{Kr}$, an absolute value of the tail peak current was measured based on the current value at the resting membrane potential using an analysis software (QPatch assay software; Sophion Bioscience A/S). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

The following data show the inhibition at 3 μM of the compounds of the present invention.

TABLE 19

| No. | hERG inhibition (%) at 3 μM |
| --- | --- |
| I-007 | 6.83 |
| I-008 | 18.5 |
| I-047 | 11.6 |
| I-059 | 20.4 |
| I-065 | 37.8 |
| I-067 | 5.39 |
| I-076 | 18.5 |
| I-105 | 40.8 |

Test Example 10: Powder Solubility Test

Appropriate amounts of the compound of the present invention were put into appropriate containers. 200 μL of JP 1$^{st}$ fluid (water is added to 2.0 g of sodium chloride and 7.0 mL of hydrochloric acid to reach 1000 mL), 200 μL of JP 2$^{nd}$ fluid (1 volume of water is added to 1 volume of the solution which 3.40 g of potassium dihydrogen phosphate and 3.55 g of anhydrous disodium hydrogen phosphate dissolve in water to reach 1000 mL), 200 μL of fasted state simulated intestinal fluid (FaSSIF), and 200 μL of fed state simulated intestinal fluid (FeSSIF) were added to the respective containers. When total amount of the compound of the present invention was dissolved after the addition of the test fluid, the compound was added as appropriate. The containers were sealed, and shaken for 1 and/or 24 hours at 37° C. The mixtures were filtered, and 100 μL of methanol was added to each of the filtrate (100 μL) so that the filtrates were two-fold diluted. The dilution ratio may be changed if necessary. After confirming that there was no bubbles and precipitates in the diluted solution, the containers were sealed and shaken. Quantification was performed by HPLC with an absolute calibration method.

Test Example 11: Pharmacokinetic Study

Materials and methods for studies on oral absorption
(1) Animal: mouse or rat
(2) Breeding conditions: mouse or rat was allowed free access to the tap water and the solid food.
(3) Dose and grouping: orally or intravenously administered at a predetermined dose; grouping was as follows (Dose depends on the compound) Oral administration: approximately 1 to 30 mg/kg (n=2 to 3) Intravenous administration: approximately 0.5 to 10 mg/kg (n=2 to 3)
(4) Dosing formulation: for oral administration, in a solution or a suspension state; for intravenous administration, in a solubilized state
(5) Dosing method: in oral administration, forcedly administer using a syringe attached a flexible feeding tube; in intravenous administration, administer from caudal vein using a syringe attached with a needle.
(6) Evaluation items: blood was collected at the scheduled time, and the plasma concentration of the compound of the present invention was measured by LC/MS/MS
(7) Statistical analysis: regarding the transition of the plasma concentration of the compound of the present invention, the area under the plasma concentration-time curve (AUC) was calculated by trapezoidal method, and the bioavailability (BA) of the compound of the present invention was calculated from the AUCs of the oral administration group and intravenous administration group.

Test Example 12: Brain Distribution Studies

Compound of the present invention was intravenously administered to a rat at approximately 0.5 mg/mL/kg dosage. 30 minutes later, all blood was drawn from the abdominal aorta under isoflurane anesthesia for death from exsanguination. The brain was enucleated and 20 to 25% of homogenate thereof was prepared with distilled water.

The obtained blood was used as plasma after centrifuging. The control plasma was added to the brain sample at 1:1. The control brain homogenate was added to the plasma sample at 1:1. Each sample was measured using LC/MS/MS. The obtained area ratio (a brain/plasma) was used for the brain Kp value.

Test Example 13: Ames Test

Ames test is performed by using Salmonellas (*Salmonella typhimurium*) TA 98, TA100, TA1535 and TA1537 and *Escherichia coli* WP2uvrA as test strains with or without metabolic activation in the pre-incubation method to check the presence or absence of gene mutagenicity of compounds of the present invention.

Test Example 14: P-Gp Substrate Test

1. Cell line:
   a. MDR1/LLC-PK1 (Becton Dickinson)
   b. LLC-PK1 (Becton Dickinson)
2. Reference substrates:
   a. Digoxin (2 µM)
   Methods and Procedures
1. MDR1 expressing LLC-PK1 cells and its parent cells were routinely cultured in Medium A (Medium 199 (Invitrogen) supplemented with 10% FBS (Invitrogen), gentamycin (0.05 mg/mL, Invitrogen) and hygromycin B (100 µg/mL, Invitrogen)) at 37° C. under 5% CO2/95% O2 gasses. For the transport experiments, these cells were seeded on Transwell (Registered trademark) insert (96-well, pore size: 0.4 µm, Coaster) at a density of $1.4 \times 10^4$ cells/insert and added Medium B (Medium 199 supplemented with 10% FBS and gentamycin at 0.05 mg/mL) to the feeder tray. These cells were incubated in a CO2 incubator (5% CO2/95% O2 gasses, 37° C.) and replace apical and basolateral culture medium every 48-72 hr after seeding. These cells were used between 4 and 6 days after seeding.
2. The medium in the culture insert seeded with MDR1 expressing cells or parent cells were removed by aspiration and rinsed by HBSS. The apical side (140 µL) or basolateral side (175 µL) was replaced with transport buffer containing reference substrates and the present invention and then an aliquot (50 µL) of transport buffer in the donor side was collected to estimate initial concentration of reference substrate and the present invention. After incubation for designed time at 37° C., an aliquot (50 µL) of transport buffer in the donor and receiver side were collected. Assay was performed by duplicate or triplicate.
3. Reference substrate and the present invention in the aliquot was quantified by LC/MS/MS.
   Calculations
   Permeated amounts across monolayers of MDR1 expressing and parent cells were determined, and permeation coefficients (Pe) were calculated using Excel 2003 from the following equitation:

$$Pe \text{ (cm/sec)} = \text{Permeated amount (pmol)/area of cell membrane } (cm^2)/\text{initial concentration (nM)/incubation time (sec)}$$

Where, permeated amount was calculated from permeation concentration (nM, concentration of the receiver side) of the substance after incubation for the defined time (sec) multiplied by volume (mL) and area of cell membrane was used 0.1433 (cm2).

The efflux ratio was calculated using the following equation:

$$\text{Efflux Ratio} = \text{Basolateral-to-Apical Pe/Apical-to-Basolateral Pe}$$

The net flux was calculated using the following equation:

$$\text{Net flux} = \text{Efflux Ratio in MDR1 expressing cells/Efflux Ratio in parent cells}$$

TABLE 20

| No. | P-gp ER ratio |
| --- | --- |
| I-007 | 5.5 |
| I-008 | 6.2 |
| I-047 | 4.7 |
| I-059 | 10 |
| I-065 | 5.7 |
| I-067 | 6.1 |
| I-076 | 6.2 |
| I-105 | 7.1 |

Test Example 15: Inhibitory Effects on P-Gp Transport

Materials
1. Cell line:
   a. MDR1/LLC-PK1 (Becton Dickinson)
   b. LLC-PK1 (Becton Dickinson)
2. Reference substrates:
   a. [$^3$H]Digoxin (1 µM)
   b. [$^{14}$C]Mannitol (1 µM)
3. Reference inhibitor:
   Verapamil (1 µM)
   Methods and Procedures
1. MDR1 expressing LLC-PK1 cells and its parent cells were routinely cultured in Medium A (Medium 199 (Invitrogen) supplemented with 10% FBS (Invitrogen), gentamycin (0.05 mg/mL, Invitrogen) and hygromycin B (100 µg/mL, Invitrogen)) at 37° C. under 5% $CO_2$/95% 02 gasses. For the transport experiments, these cells were seeded on Transwell (Registered trademark) insert (96-well, pore size: 0.4 µm, Coaster) at a density of $1.4 \times 10^4$ cells/insert and added Medium B (Medium 199 supplemented with 10% FBS and gentamycin at 0.05 mg/mL) to the feeder tray. These cells were incubated in a $CO_2$ incubator (5% $CO_2$/95% $O_2$ gasses, 37° C.) and replace apical and basolateral culture medium every 48-72 hr after seeding. These cells were used between 6 and 9 days after seeding.
2. The medium in the culture insert seeded with MDR1 expressing cells or parent cells were removed by aspiration and rinsed by HBSS. The apical side (150 µL) or basolateral side (200 µL) was replaced with transport buffer containing reference substrates with or without the compound of the present invention and then an aliquot (50 µL) of transport buffer in the donor side was collected to estimate initial concentration of reference substrate. After incubation for designed time at 37° C., an aliquot (50 µL) of transport buffer in the donor and receiver side were collected. Assay was performed by triplicate.

3. An aliquot (50 µL) of the transport buffer was mixed with 5 mL of a scintillation cocktail, and the radioactivity was measured using a liquid scintillation counter.

Calculations

Permeated amounts across monolayers of MDR1 expressing and parent cells were determined, and permeation coefficients (Pe) were calculated using Excel 2003 from the following equitation:

Pe (cm/sec)=Permeated amount (pmol)/area of cell membrane (cm$^2$)/initial concentration (nM)/ incubation time (sec)

Where, permeated amount was calculated from permeation concentration (nM, concentration of the receiver side) of the substance after incubation for the defined time (sec) multiplied by volume (mL) and area of cell membrane was used 0.33 (cm$^2$).

The efflux ratio will be calculated using the following equation:

Efflux Ratio=Basolateral-to-Apical Pe/Apical-to-Basolateral Pe

The net flux is calculated using the following equation:

Net flux=Efflux Ratio in MDR1 expressing cells/Efflux Ratio in parent cells

The percent of control was calculated as the net efflux ratio of reference compounds in the presence of the compound of the present invention to that in the absence of the compound of the present invention.

$IC_{50}$ values were calculated using the curve-fitting program XLfit.

(Test Example 16: P-Gp Substrate Test Using Mdr1a/1b (−/−) B6 Mice)

Materials
Animal: mdr1a/1b (−) B6 mice (KO mouse) or C57BL/6J mice (Wild mouse)

Methods and Procedures
1. Animals may be fed prior to dosing of the compounds of the present invention.
2. The compounds of the present invention are dosed to three animals for each time point and blood and brain samples are removed at selected time points (e.g. 15 min, 30 min, 1 hr, 2 hr, 4 hr, 6 hr, 8 hr, or 24 hr) after dosing. Blood (0.3-0.7 mL) is collected via trunk blood collection with syringe containing anticoagulants (EDTA and heparin). Blood and tissue (e.g. brain) samples are immediately placed on melting ice.
3. Blood samples are centrifuged (1780× g for 10 minutes) for cell removal to obtain plasma. Then, plasma samples are transferred to a clean tube and stored in a −70° C. freezer until analysis.
4. Tissue (e.g. brain) samples are homogenized at a 1:3 ratio of tissue weight to ml of stilled water and transferred to a clean tube and stored in a −70° C. freezer until analysis.
5. Plasma and tissue (e.g. brain) samples are prepared using protein precipitation and analyzed by LC/MS/MS. The analytical method is calibrated by including a standard curve constructed with blank plasma or brain samples and known quantities of analyte. Quality control samples are included to monitor the accuracy and precision of the methodology.
6. Plasma and brain concentration values (ng/mL and ng/g) are introduced into an appropriate mathematical tool used for calculating the pharmacokinetic parameters. A common platform is the WinNonlin (Registered trademark) pharmacokinetic software modeling program.

Calculations
Kp; Tissue to Plasma concentration ratio

Kp ratio=Kp in KO mouse/Kp in Wild mouse

KO/Wild ratio of AUC Tissue/AUC Plasma=(AUC Tissue/AUC Plasma (KO mouse))/(AUC Tissue/AUC Plasma (Wild mouse))

Test Example 17: Anesthetized Guinea Pig Cardiovascular Study

Animal species: Guinea pig (Slc:Hartley, 4-5 weeks old, male), N=4
Study Design:
Dosage: 3, 10, and 30 mg/kg (in principle)
(The compounds of the present invention are administered cumulatively)
Formulation:
Composition of Vehicle; Dimethylacetamide (DMA): Polyethylene glycol 400 (PEG400): Distilled water (D.W.)=1:7:2 (in principle).
The compounds of the present invention are dissolved with DMA and then added PEG400 and D.W. Finally, 1.5, 5, and 15 mg/mL solutions are prepared.
Dosing Route and Schedule:
Intravenous infusion for 10 min (2 mL/kg).
0 to 10 min: 3 mg/kg, 30 to 40 min: 10 mg/kg, 60 to 70 min: 30 mg/kg
Vehicle is administered by the same schedule as the above.
Group Composition:
Vehicle group and the compound of the present invention group (4 guinea pigs per group).
Evaluation Method:
Evaluation Items:
Mean blood pressure [mmHg], Heart rate (derived from blood pressure waveform [beats/min]), QTc (ms), and Toxicokinetics.
Experimental Procedure:
Guinea pigs are anesthetized by urethane (1.4 g/kg, i.p.), and inserted polyethylene tubes into carotid artery (for measuring blood pressure and sampling blood) and jugular vein (for infusion test compounds). Electrodes are attached subcutaneously (Lead 2). Blood pressure, heart rate and electrocardiogram (ECG) are measured using PowerLab (Registered trademark) system (ADInstruments).
Toxicokinetics:
Approximately 0.3 mL of blood (approximately 120 µL as plasma) is drawn from carotid artery with a syringe containing heparin sodium and cooled with ice immediately at each evaluation point. Plasma samples are obtained by centrifugation (4C, 10000 rpm, 9300×g, 2 minutes). The procedure for separation of plasma is conducted on ice or at 4° C. The obtained plasma (TK samples) is stored in a deep freezer (set temperature: −80° C.).
Analysis methods: Mean blood pressure and heart rate are averaged a 30-second period at each evaluation time point. ECG parameters (QT interval [ms] and QTc are derived as the average waveform of a 10-second consecutive beats in the evaluation time points. QTc [Fridericia's formula; QTc=QT/(RR)$^{1/3}$] is calculated using the PowerLab (Registered trademark) system. The incidence of arrhythmia is visually evaluated for all ECG recordings (from 0.5 hours before dosing to end of experiment) for all four animals.
Evaluation Time Points:
Before (pre dosing), and 10, 25, 40, 55, 70, and 85 min after the first dosing.

Data Analysis of QTc:

Percentage changes (%) in QTc from the pre-dose value are calculated (the pre-dose value is regarded as 100%). Relative QTc is compared with vehicle value at the same evaluation point.

Test Example 18: Pharmacology in the Beagle Dog

Test compounds were tested to evaluate the effect on the beta-amyloid profile in cerebrospinal fluid (CSF) of dogs after a single dose, in combination with pharmacokinetic (PK) follow up and limited safety evaluation.

In the case of compounds shown below, two or 4 beagle dogs (1 or 2 male, 1 or 2 female) were dosed with vehicle (1 mL/kg of an aqueous solution of 20% cyclodextrin) and 4 beagle dogs (2 males and 2 females) per dose group were dosed with test compound at the doses indicated in Table 20 in an aqueous 20% cyclodextrin solution with a concentration in mg/mL identical to the dose given in mg/kg) on an empty stomach.

CSF was taken in conscious animals directly from the lateral ventricle via a cannula which was screwed in the skull and covered with subcutaneous tissue and skin, before and at 4, 8, 25 and 49 hours after dosing. Eight hours after dosing the animals got access to their regular meal for 30 minutes. Blood was taken for PK follow up (0.5, 1, 2, 4, 8, 25 and 49 hours) and serum samples for biochemistry were taken before and at 8 and 25h after dosing. The CSF samples were used for measurement of Abeta 1-37, Abeta 1-38, Abeta 1-40 and Abeta 1-42. The results are summarized in the Table below:

TABLE 21

| No. | % Decrease in Abeta 1-42 at 8 h post dosing compared to own baseline | % Decrease in Abeta 1-42 at 24 h[(a)] or 25 h[(b)] post dosing compared to own baseline | % Decrease in Abeta 1-42 at 49 h post dosing compared to own baseline | Dose (mg/kg) |
| --- | --- | --- | --- | --- |
| I-007 | −61 | −23 | NR | 0.31 |
| I-007 | −69 | −48 | NR | 0.63 |
| I-007 | −64 | −82 | −40 | 3.75 |
| I-008 | −57 | −28 | −25 | 0.31 |
| I-008 | −58 | −48 | NR | 0.63 |
| I-008 | −81 | −76 | −49 | 2.5 |
| I-065 | −49 | −52 | −20 | 0.63 |
| I-065 | −59 | −56 | −34 | 1.25 |
| I-067 | −36 | NR | NR | 0.31 |
| I-067 | −64 | NR | NR | 0.63 |
| I-076 | −68 | NR | NR | 0.31 |
| I-076 | −65 | NR | NR | 0.63 |

% decrease indicated at 8 h and at last time point at which relevant decrease (>20% decrease) was observed.

Test Example 19: Dansyl GSH Trapping Test

Dansyl glutathione (glutathione) trapping is a test of investigating reactive metabolites.

The reaction conditions were as follows: substrate, 50 μmol/L the compounds of the present invention; trapping reagent, 0.1 mmol/L dansyl GSH; protein content of pooled human liver microsomes, 1 mg/mL; pre-reaction time, 5 minutes; reaction time, 60 minutes; reaction temperature, 37° C.

Pooled human liver microsomes and a solution of the compound of the present invention in K-Pi buffer (pH 7.4) as a pre-reaction solution were added to a 96-well plate at the composition of the pre-reaction. NADPH as a cofactor was added to initiate a reaction. After a predetermined time of a reaction, a part is transferred to another 96-well plate, and a solution of acetonitrile including 5 mmol/L dithiothreitol was added to stop the reaction. After centrifuged at 3000 rpm for 15 minutes, fluorescence peak area of the dansyl GSH trapped metabolites was quantified by HPLC with fluorescence detection.

Test Example 20: [14C]—KCN Trapping Test

[$^{14}$C]-potassium cyanide (KCN) trapping is a test of investigating reactive metabolites.

The reaction conditions were as follows: substrate, 10 or 50 μmol/L the compounds of the present invention; trapping reagent, 1 mmol/L [$^{14}$C]-KCN (11.7 μCi/tube); protein content of pooled human liver microsomes, 1 mg/mL; pre-reaction time, 5 minutes; reaction time, 60 minutes; reaction temperature, 37° C.

Pooled human liver microsomes and a solution of the compound of the present invention in K-Pi buffer (pH 7.4) as a pre-reaction solution were added to a 96-well plate at the composition of the pre-reaction. NADPH as a cofactor was added to initiate a reaction. After a predetermined time, the metabolic reactions were terminated and [$^{14}$C]-KCN trapped metabolites were extracted to 100 μL methanol solutions by spin-column. Radio peak area of the [$^{14}$C]-KCN trapped metabolites is quantified by Radio-HPLC system.

FORMULATION EXAMPLES

The following Formulation Examples are only exemplified and not intended to limit the scope of the present invention.

Formulation Example 1: Tablet

| | |
| --- | --- |
| Compound of the present invention | 15 mg |
| Lactose | 15 mg |
| Calcium stearate | 3 mg |

All of the above ingredients except for calcium stearate are uniformly mixed. Then the mixture is crushed, granulated and dried to obtain a suitable size of granules. Then, calcium stearate is added to the granules. Finally, tableting is performed under a compression force.

Formulation Example 2: Capsules

| | |
| --- | --- |
| Compound of the present invention | 10 mg |
| Magnesium stearate | 10 mg |
| Lactose | 80 mg |

The above ingredients are mixed uniformly to obtain powders or fine granules, and then the obtained mixture is filled in capsules.

Formulation Example 3: Granules

| | |
|---|---|
| Compound of the present invention | 30 g |
| Lactose | 265 g |
| Magnesium stearate | 5 g |

After the above ingredients are mixed uniformly, the mixture is compressed. The compressed matters are crushed, granulated and sieved to obtain suitable size of granules.

Formulation Example 4: Orally Disintegrated Tablets

The compounds of the present invention and crystalline cellulose are mixed, granulated and tablets are made to give orally disintegrated tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injection.

Formulation Example 7: Infusions

The compounds of the present invention and phosphate buffer are mixed to give injection.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compounds of the present invention can be a medicament useful as an agent for treating or preventing a disease induced by production, secretion and/or deposition of amyloid β proteins.

The invention claimed is:

1. A compound of Formula (I):

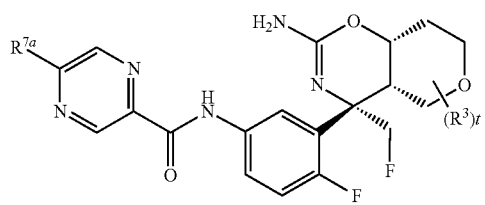

(I)

wherein $R^3$ is alkyl optionally substituted with one or more halogen;

t is 0 or 1; and $R^{7a}$ is alkyloxy optionally substituted with one or more group(s) selected from the group consisting of halogen, non-aromatic carbocyclyl, and aromatic heterocyclyl; alkyl optionally substituted with one or more halogen; or aromatic heterocyclyl optionally substituted with one or more alkyl;

or a pharmaceutically acceptable salt thereof.

2. The compound according to claim 1, wherein

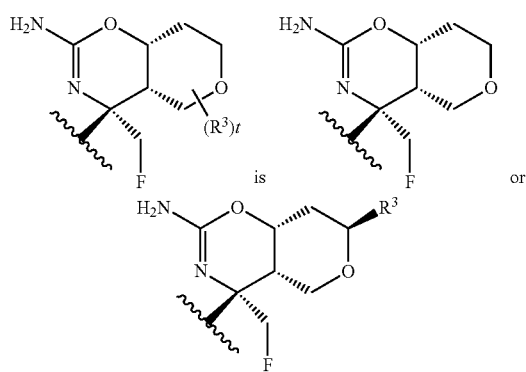

or a pharmaceutically acceptable salt thereof.

3. The compound according to claim 1, wherein

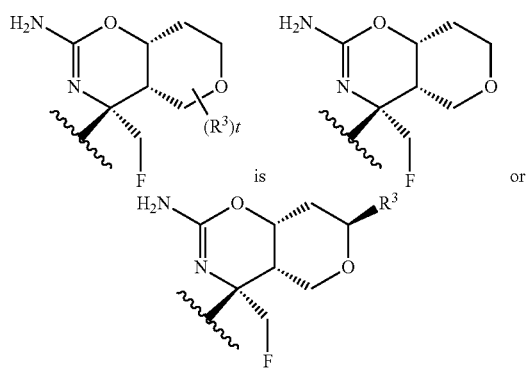

and $R^{7a}$ is alkyloxy optionally substituted with one or more halogen, or a pharmaceutically acceptable salt thereof.

4. The compound according to claim 1, selected from the group consisting of:

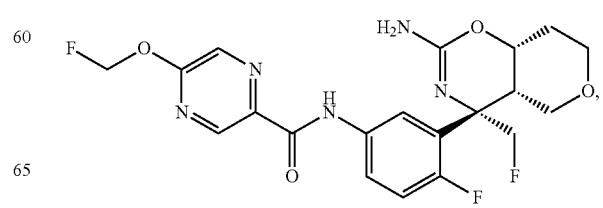

-continued
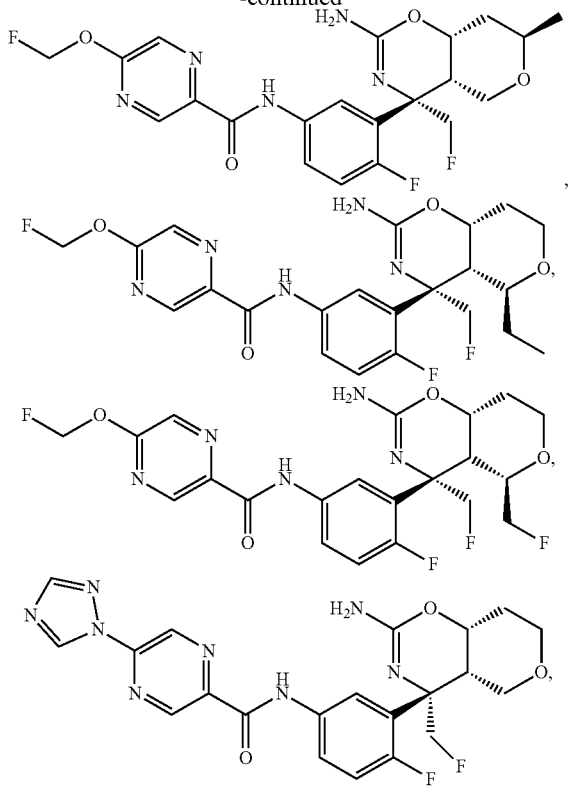
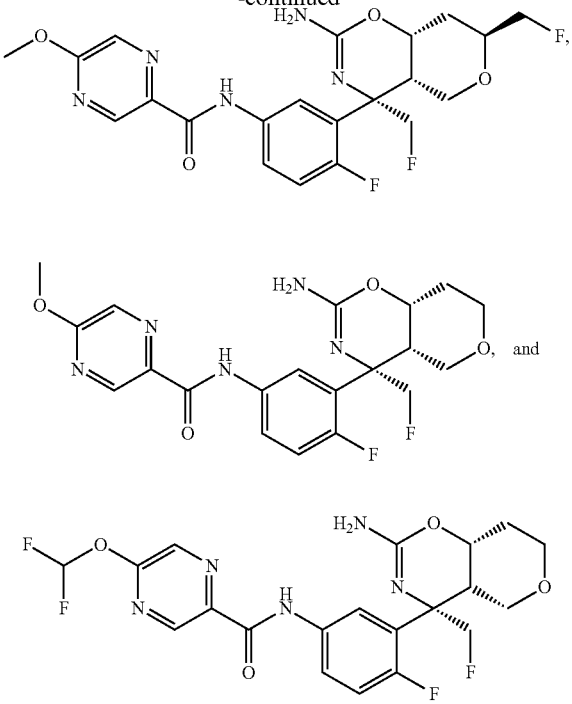
or a pharmaceutically acceptable salt thereof.
* * * * *